(12) United States Patent
Bett et al.

US007132277B1

(10) Patent No.: US 7,132,277 B1
(45) Date of Patent: Nov. 7, 2006

(54) HELPER DEPENDENT VECTOR SYSTEM FOR GENE THERAPY

(75) Inventors: Andrew Bett, Lansdale, PA (US); Volker Sandig, Berlin (DE); Rima Youil, North Wales, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/890,836

(22) PCT Filed: Jan. 31, 2000

(86) PCT No.: PCT/US00/02405

§ 371 (c)(1),
(2), (4) Date: Aug. 3, 2001

(87) PCT Pub. No.: WO00/46360

PCT Pub. Date: Aug. 10, 2000

(51) Int. Cl.
*C12N 15/00* (2006.01)
(52) U.S. Cl. .............................. 435/320.1; 435/235.1; 435/455; 435/456; 435/457; 435/173.3; 536/23.1
(58) Field of Classification Search ............... 536/23.1, 536/455, 456, 457, 173.3, 235.1, 320.1; 435/320.1, 435/235.1, 235, 173.3, 455, 456, 457
See application file for complete search history.

(56) References Cited

U.S. PATENT DOCUMENTS

| 5,464,758 A | 11/1995 | Gossen et al. |
| 5,650,298 A | 7/1997 | Bujard et al. |
| 5,654,182 A | 8/1997 | Wahl et al. |
| 5,874,534 A | 2/1999 | Vegeto et al. |
| 5,919,676 A * | 7/1999 | Graham et al. ............ 435/91.4 |

FOREIGN PATENT DOCUMENTS

| WO | WO 93/23431 | 11/1993 |
| WO | WO 96/40955 | 12/1996 |
| WO | WO 97/00326 | 1/1997 |
| WO | WO 97/32481 | 9/1997 |
| WO | WO97/32481 | * 9/1997 |
| WO | WO 97/48806 | 12/1997 |
| WO | WO 98/13510 | 4/1998 |

OTHER PUBLICATIONS

Grable et al., 1992 Journal of Virology vol. 66 (2), pp. 723-731.*
Hierholzer et al., "Adenoviruses from Patients with AIDS: A Plethora of Serotypes and a Description of Five New Serotypes of Subgenus D (Types 43-47)", The Journal of Infectious Diseases, vol. 158, No. 4, pp. 804-813 (Oct. 1998).
Hitt et al., "Human Adenovirus Vectors for Gene Transfer into Mammalian Cells", Advances in Pharmacology, vol. 40, pp. 137-206 (1997).
Mitani et al., "Rescue, propagation, and partial purification of a helper virus-dependent adenovirus vector", Proc. Natl. Acad. Sci. USA, vol. 92, pp. 3854-3858 (Apr. 1995).

Fisher et al., "Recombinant Adenovirus Deleted of AllViral Genes for Gene Therapy of Cystic Fibrosis", Virology, vol. 217, pp. 11-22 (1996).
Kochanek et al., "A new adenoviral vector: Replacement of all viral coding sequences with 28 kb of DNA independently repressing both full-length dystrophin and β-galactosidase", Proc. Natl. Acad. Sci USA, vol. 93, pp. 5731-5736 (Jun. 1996).
Parks et al., "A helper-dependent adenovirus vector system: Removal of helper virus by Cre-mediated excision of the viralpackaging signal", Applied Biological Sciences, vol. 93, pp. 13565-13570 (1996).
Parks et al., "A Helper-Dependent System for Adenovirus Vector Production Helps Define a Lower Limit for Efficient DNA Packaging", Journal of Virology, vol. 71, No. 4, pp. 3293-3298 (Apr. 1997).
Schiedner et al., "Genomic DNA transfer with a high-capacity adenovirus vector results in improved *in vivo* gene expression and decreased toxicity", Nature Genetics, vol. 18, pp. 180-183 (Feb. 1998).
Arnold et al., "The promoter of the chicken cardiac myosin light chain 2 gene shows cell-specific expression in transfected primary cultures of chicken muscle", Nucleic Acids Research, vol. 16, No. 6, pp. 2411-2429 (1988).
Johnson et al., "Muscle Creatine Kinase Sequence Elements Regulating Skeletal and Cardiac Muscle Expression in Transgenic Mice", Molecular and Cellular Biology, vol. 9, No. 8, pp. 3393-3399 (Aug. 1989).
Wang et al., "Positive and negative regulation of gene expression in eukaryotic cells with an inducible ftranscriptional regulator", Gene Therapy, vol. 4, pp. 432-441 (1997).
Schmid et al., "Bipartite Structure and Functional Independence of Adenovirus Type 5 Packaging Elements", Journal of Virology, vol. 71, No. 5, pp. 3375-3384 (May 1997).

(Continued)

*Primary Examiner*—James Housel
*Assistant Examiner*—Myron G. Hill
(74) *Attorney, Agent, or Firm*—J. M. Giesser; J. E. Switzer

(57) ABSTRACT

The present invention features helper-dependent adenoviral vector elements, and helper adenoviral elements, that enhance the production and isolation of helper-dependent adenoviral vectors. Such elements include a modified packaging signal having low homology to, and preferably less activity than, a wild-type packaging signal, an E4 non-coding segment directly joined to the 5' ITR that confers a selective advantage, and stuffer region(s) that provide a helper-dependent adenoviral vector with a GC content of about 50% to about 60%. The modified packaging signal is preferably used in a helper virus to decrease recombination and generation of the virus. The E4 non-coding segment and the stuffer region(s) are preferably used in a helper-dependent adenoviral vector to provide the vector with a growth advantage over a helper virus.

15 Claims, 8 Drawing Sheets

OTHER PUBLICATIONS

Morsy et al., "An adenoviral vector deleted for all viral coding sequences results in enhanced safety and extended expression of a leptin transgene", Proc. Natl. Acad. Sci. USA, vol. 95, pp. 7866-7871 (Jul. 1998).

Chartier et al., "Efficient Generation of Recombinant Adenovirus Vectors by Homologous Recombination in *Escherichia coli*", Journal of Virology, vol. 70, No. 7, pp. 4805-4810 (Jul. 1996).

Bett et al., "An efficient and flexible system for construction of adenovirus vectors with insertions or deletions in early regions 1 and 3", Proc. Natl. Acad. Sci. USA, vol. 91, pp. 8802-8806 (Sep. 1994).

Sandig et al., "Optimization of the helper-dependent adenovirus system for production and potency *in vivo*", PNAS, vol. 97, No. 3, pp. 1002-1007 (Feb. 2000).

Grable et al., "Adenovirus Type 5 Packaging Domain is Composed of a Repeat Element that is Functionally Redundant", Journal of Virology, vol. 64, No. 5, pp. 2047-2056 (May 1990).

Hardy et al., "Construction of Adenovirus Vectors through Cre-lox Recombination", Journal of Virology, vol. 71, No. 3, pp. 1842-1849 (Mar. 1997).

Ilan et al., "Insertion of the adenoviral E3 region into a recombinant viral vector prevents antivira humoral and cellular immune responses and permits long-term gene expression", Proc. Natl. Acad. Sci. USA, vol. 94, pp. 2587-2592 (Mar. 1997).

Mittal, et al., "Induction of Systemic and Mucosal Immune Responses in Cotton Rats Immunized with Human Adenovirus Type 5 Recombinants Rxpressing the Full and Truncated Forms of Bovine Herpesvirus Type 1 Glycoprotein gD1", Virology, vol. 222, pp. 299-309 (1996).

Grable et al., cis and trans Requirements for the Selective Packaging of Adenovirus Type 5 DNA, Journal of Virology, vol. 66, No. 2, pp. 723-731 (Feb. 1992).

\* cited by examiner

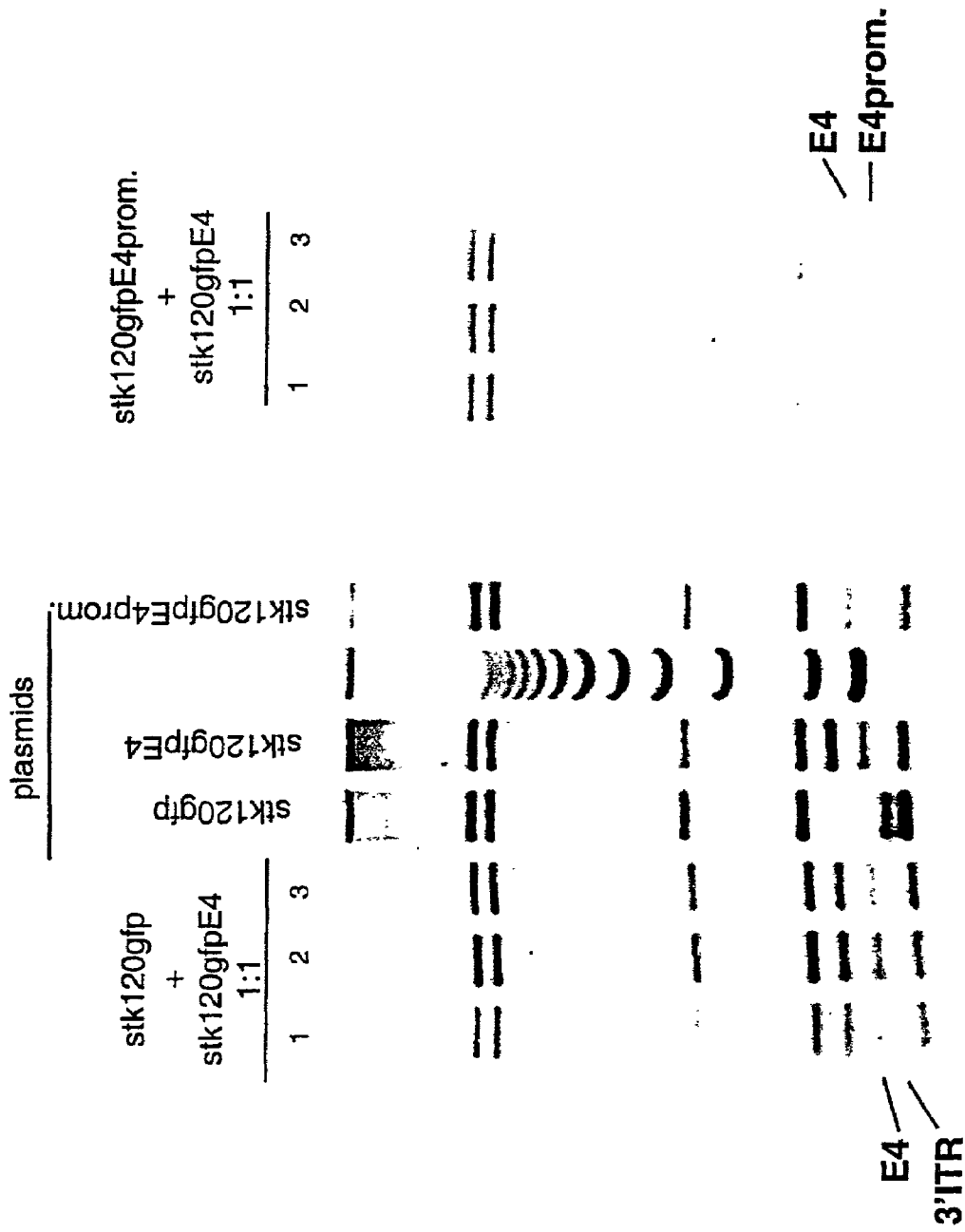

```
                         SEQUENCE LISTING

<160> NUMBER OF SEQ ID NOS: 17

<210> SEQ ID NO 1
<211> LENGTH: 15
<212> TYPE: DNA
<213> ORGANISM: Artificial Sequence
<220> FEATURE:
<223> OTHER INFORMATION: Consensus sequence
<220> FEATURE:
<221> NAME/KEY: misc_feature
<222> LOCATION: (1)...(15)
<223> OTHER INFORMATION: n = A,T,C or G

<400> SEQUENCE: 1
atttgnnnnn nnncg                                                  15

<210> SEQ ID NO 2
<211> LENGTH: 10
<212> TYPE: DNA
<213> ORGANISM: Artificial Sequence
<220> FEATURE:
<223> OTHER INFORMATION: Adenovirus 5

<400> SEQUENCE: 2
attttgtgtt                                                        10

<210> SEQ ID NO 3
<211> LENGTH: 10
<212> TYPE: DNA
<213> ORGANISM: Artificial Sequence
<220> FEATURE:
<223> OTHER INFORMATION: Consensus sequence

<400> SEQUENCE: 3
attttgttgt                                                        10

<210> SEQ ID NO 4
<211> LENGTH: 158
<212> TYPE: DNA
<213> ORGANISM: Artificial Sequence
<220> FEATURE:
<223> OTHER INFORMATION: Synthetic packaging signal

<400> SEQUENCE: 4
gtacacagga agtgactttt aacgcgcggt ttgttacgga tgttgtagta aatttgtcta    60
gggccgagta agatttgacc gtttacgcgg ggactttgaa taagagcgag tgaaatctga   120
ataattttgt tgtactcata gcgcgtaatc tctagacg                          158

<210> SEQ ID NO 5
<211> LENGTH: 158
<212> TYPE: DNA
<213> ORGANISM: Artificial Sequence
<220> FEATURE:
<223> OTHER INFORMATION: Adenovirus 5

<400> SEQUENCE: 5
gtacacagga agtgacaatt ttcgcgcggt tttaggcgga tgttgtagta aatttgggcg    60
taaccgagta agatttggcc attttcgcgg gaaaactgaa taagaggaag tgaaatctga   120
ataattttgt gttactcata gcgcgtaatc tctagacg                          158
```

```
<210> SEQ ID NO 6
<211> LENGTH: 65
<212> TYPE: DNA
<213> ORGANISM: Artificial Sequence
<220> FEATURE:
<223> OTHER INFORMATION: Linker

<400> SEQUENCE: 6
agctcggccg attattggcg cgccagatct gcggccgctt ctagaaacgc gtgaattcgg      60
cgcca                                                                 65

<210> SEQ ID NO 7
<211> LENGTH: 65
<212> TYPE: DNA
<213> ORGANISM: Artificial Sequence
<220> FEATURE:
<223> OTHER INFORMATION: Linker

<400> SEQUENCE: 7
agcttggcgc cgaattcacg cgtttctaga agcggccgca gatctggcgc gccaataatc      60
ggccg                                                                 65

<210> SEQ ID NO 8
<211> LENGTH: 40
<212> TYPE: DNA
<213> ORGANISM: Artificial Sequence
<220> FEATURE:
<223> OTHER INFORMATION: PCR Primer

<400> SEQUENCE: 8
attggcgcgc cttctttctg ggatgattca gcatcaactc                            40

<210> SEQ ID NO 9
<211> LENGTH: 41
<212> TYPE: DNA
<213> ORGANISM: Artificial Sequence
<220> FEATURE:
<223> OTHER INFORMATION: PCR Primer

<400> SEQUENCE: 9
gatcgtcggc cgcttgggtc atagacttct ttgagaacca g                         41

<210> SEQ ID NO 10
<211> LENGTH: 41
<212> TYPE: DNA
<213> ORGANISM: Artificial Sequence
<220> FEATURE:
<223> OTHER INFORMATION: PCR Primer

<400> SEQUENCE: 10
atcagttagc ggccgcacaa gctaagatca caaagctgtt t                         41

<210> SEQ ID NO 11
<211> LENGTH: 37
<212> TYPE: DNA
<213> ORGANISM: Artificial Sequence
<220> FEATURE:
<223> OTHER INFORMATION: PCR Primer

<400> SEQUENCE: 11
tatggcgcgc cgctgacacc cagcctgggt gccggtg                              37
```

```
<210> SEQ ID NO 12
<211> LENGTH: 39
<212> TYPE: DNA
<213> ORGANISM: Artificial Sequence
<220> FEATURE:
<223> OTHER INFORMATION: PCR Primer

<400> SEQUENCE: 12
tcgacgcgta gcgctgtgtg gccttggcag tttccatag                    39

<210> SEQ ID NO 13
<211> LENGTH: 45
<212> TYPE: DNA
<213> ORGANISM: Artificial Sequence
<220> FEATURE:
<223> OTHER INFORMATION: PCR Primer

<400> SEQUENCE: 13
tcagtaatgc ggccgcggga tcattcctgg actcagattg ttctg             45

<210> SEQ ID NO 14
<211> LENGTH: 41
<212> TYPE: DNA
<213> ORGANISM: Artificial Sequence
<220> FEATURE:
<223> OTHER INFORMATION: PCR Primer

<400> SEQUENCE: 14
tattaaggcg ccgggcatgg gagtgatctc accaactctg g                 41

<210> SEQ ID NO 15
<211> LENGTH: 46
<212> TYPE: DNA
<213> ORGANISM: Artificial Sequence
<220> FEATURE:
<223> OTHER INFORMATION: PCR Primer

<400> SEQUENCE: 15
tcgacgcgta tttaaatgtg ctggagtgtt gagatactgt agtggt            46

<210> SEQ ID NO 16
<211> LENGTH: 28068
<212> TYPE: DNA
<213> ORGANISM: Artificial Sequence
<220> FEATURE:
<223> OTHER INFORMATION: Modified adenovirus

<400> SEQUENCE: 16
aaacatcatc aataatatac cttattttgg attgaagcca atatgataat gagggggtgg    60
agtttgtgac gtggcgcggg gcgtgggaac ggggcgggtg acgtagtagt gtggcggaag   120
tgtgatgttg caagtgtggc ggaacacatg taagcgacgg atgtggcaaa agtgacgttt   180
ttggtgtgcg ccggtgtaca caggaagtga caattttcgc gcggttttag cggatgttg    240 tagtaaattt gggcgtaacc gagtaagatt tggccatttt cgcgggaaaa ctgaataaga    300
ggaagtgaaa tctgaataat tttgtgttac tcatagcgcg taatatttgt ctagggccgc    360
ggggactttg accgtttacg tggagactcg cccaggtgtt tttctcaggt gttttccgcg    420
ttccgggtca agttggcgt tttgattcgg ccgcttgggt catagacttc tttgagaacc     480
agttataagc tatggtttct ctccacagaa aaagcactta tggtgtctcc ccctttccag    540
cccaccaaca ttttacatct aatttggggg ggttttctgg accacttaat acccatccat    600
ggatctcatg tgaagactcc cctggcttga gaaatcactg tcttgttgaa aatgggaaca    660
```

-continued

```
aagctaagtc agatagctgg ttcatcagca atgactttga ccaagcctga tcccacccta      720 cccccacccca ccccagtgac caccccccac aatggagcac acaactctaa actggtttgt     780
aggtatgtgt gtgtgaacac gctgaggaat ctgcaaaacc aaatggtgag tgcaaaacca     840
aacagtcacg agtaaatctc acaacaacca cgtcctgagc tgcagccctt gttgaactat     900
accccactag ggccccaaga ttttaggact tgtgtgtggg tgggacctcc cctttctatc     960
atgctttaga agacagggat ttcaccagaa ttgaacatat tgaacatatg acccattttt    1020
ttcagccaaa ggcaattaaa ataacttcat acttgatatc catgtcagca aaagctgcaa    1080
aacgcaaatg ggtggctgct aagagccctg gtaccctgac gagcacacca agtgcttagc    1140
aacagtggtg tccaaggac cagctggaag cctgccttga tgagaagttg ctcttctttc     1200
tacatgaagg aacacctcta ctctcctgct tttaatacct gagctgtgag tgatcatcta    1260
tgtccattag caaacatccc agtggagaag gaaacactca tacccgaaat ctaagctaca    1320
tagttggaat cacttcaact tattgcaata aacacttact aagcacctat tgtgggcaag    1380 tcttttgcaat ggataatagt tcagtagata ttttgatgta atatttgaaa taacaataaa    1440
aattgccacc actgaattta ttgagcattt gctgtgcttt aggcactaac ccaggttctt    1500
taaatatttg gtcttattcg atctgtataa atagccatct atgagaaagg gactattatt    1560
gcccttattt tacaaatgag gccaatgagg cccagagagg ttaactaagt tgcccaaaat    1620
catacagccc actagtggca gagcaggatg caaacccagg cttgcctcgt tcccaagccc    1680
acatgtcgtt tgcattggtg tggaggtgtg catgtgttta gtcattagca tgttatatga    1740
taagcaagtt ttgaaacata gaaacttaaa atgtgccatt aagaaaagta caggcaaggt    1800
tttccaaggg gaggtgtgga cctccggaca aattttttaag aactaattat aaatacttaa    1860
aaatgggaat aagaagacaa cctaactacc tgaacagttt tagagatgac tcatgcccac    1920
cctctaaaac ccaaacaaaa acaacaaagt caagaaaacc catgaaatct tagcaagcga    1980
tttctatgta cttgtgaaaa ggatttcttt accattctaa tgggatttat gccaaccata    2040
gagggctcag tgcccctccc atggggtggt tagtgagtac agagctgagc tcaccggcca    2100
tctgcagctt catgttatca agctccagtt tgtccttgga gcaaggttat ctgggacatg    2160
agcagaggca ttgctttctg caatggacag ttctttctgc ctgcatacct agctccttga    2220
taactttaaa taccatttta tagccacact ggagttttga agacctcaat atgcaaatat    2280
tactcaggtt ctgattactt gtctgctcca tgataacaca ctctaaaagc aatgaatggg    2340
gcttatttgt agagaactga agcattttaa gcttttgctc aggaatccct ggtagcttcc    2400
tgtgacttgc aagatattag tgatgggtca agaaacagga ccccccatca gcataacata    2460
cgcagtgcct cagtagtcca tcaggcagaa aaaactgcag atggcacatg gaaatgacca    2520
gcggcggaag ataccccgac agtgtgggca gttctatttc agcagcaatc aagaggggc    2580 ctggagccac tcaatcaagt ggagcaggat gggagcaagc actgtgcaga ccaatgcaat    2640
ccccagttaa cacaaaaaat aaataaaaga gatgagattc agtctcttga ctgtgactga    2700
ctgggagctt tatagctgat gcttgtgtct tttctccatt ttatttaatt aggaaaagaa    2760
atgcttatca cacactctac gtgtgaggta caacctccac aggaaaggtt gttaggaaca    2820
tttcaacttc tagaagtttc taaacataag gtaaatccat ctttgtcctt gggatcactg    2880
cacatctcag aaaggcaaat aaatcagtaa ttggtgggca taattactag ctcatggact    2940
gacaaggtct acactatttc gaatctcaca gaagtaagcc atgggacaga tagagtctga    3000
tagtggtgcc ccgtttcctg gaggtcacac ttactcatcc ccctggaccc tgggcttctc    3060
```

-continued

| | |
|---|---|
| atgattgtca gagagtttgc tggaaccagg tcagcccagt ttcccttccc ctgaaaaatc | 3120 |
| ctccaatggc tcgcaccaag actagagatg caagtgcaag cacatccacc ctctcagcag | 3180 |
| ccaggttttg cgttccataa tgtcacgtac ccccagtcat accaatctcc ttggagctct | 3240 |
| ccagacaggc tgccatgtgt ggtcggccct ctgtgcttgt gctccttggt ttgccaagcc | 3300 |
| tggaatgccc tttctccatg attgtactct gggaattctg tgtgtctttc gagatgaagc | 3360 |
| tcctccaccc tggaaattct gcctctcttt ccaggtccag ctcctgtggc tgaatacccct | 3420 |
| tggctgactg aacattcttg ctgggccaag tcttaatcat ctctaaatcc ctctggtgcc | 3480 |
| ccgacagtat ctagcccagg caaagggctc agcaaatact tgcaaaattc aataaacttt | 3540 |
| actatgttac tagcttggca tgatgttcta ggcacttggg agattataat ctggtgagca | 3600 |
| ttgtgctagt cttttttttg ggataaacac caatgataaa ctgagccttt actctcattt | 3660 |
| tagcacatct actcatctct tttcaatgct ggtgggttta taaaacccat cagtagaaca | 3720 |
| gagagtgatc ataatcatat ggtgaaaata acatcagcta acatatttac tgaacatgct | 3780 |
| ttagtgtgct gggcactgaa ctctgtgcac atgtgaattt gagatagatt gttcctagct | 3840 |
| aataagatga ggaagtggag atgggcttac tcaagtcaca caatagcaag atggggtaca | 3900 |
| gacagaaacc aagctagaaa ccaagcaacc cctgggtttg gaaatgcatg ggctcctcct | 3960 |
| ctgcacatgg cgaggagcag tcaggtgctc ctccttctct catactgaaa taactctgca | 4020 |
| cttttggcta ttctgtgaca ctctgtgcta ttctgtagct caaatggctc tggtgcaagg | 4080 |
| agctcagatt atgactaacc cccatagata ttcagctgct ttgcaagaag tggatgaatg | 4140 |
| ctctggcttt ataaattatt gactagattg gatattggcc caatctccac tctggtgatt | 4200 |
| cggaaggagg catatgcaca tttgcaaggt tatagtagtg cactctaatt ccactggctt | 4260 |
| ctgagagctt gtaggtttct tgacttaatc attctggaat taaggtaatg gatcctcaac | 4320 |
| acctttctt tccctggcct ttactaacca tgtaacagaa atgagcagag aaaacccaag | 4380 |
| aaagcgaact ggagacttga tgagtgtgtc aaagatgctc agagtccaag gtcctctgtg | 4440 |
| gctcactgac ttcagaagcc aacctccgtt gttcaagtca cttgtgaggt tactatgcta | 4500 |
| gagcactaaa tattatccag atagcccaaa gaggtgaagg cagacatgtg gaagaacctg | 4560 |
| gattttggg caagttgatg aatgcctcct gccccatatc aaagagaggt gataggagac | 4620 |
| aactttgtga atttgaaata atgcaccggg gaaacaggaa aacgtaatgt aagtcacgct | 4680 |
| tcttggcttt tttcttgcca ttaccctact tggccaagtg caaatgggat ttcaatatat | 4740 |
| cataagtatg catctattaa taacaatgca agaaagctgt acaactgaag tctgagattt | 4800 |
| tgtaagaaac agaatctctg taagcatcac catccaacag aacttcctga gttgatgctg | 4860 |
| aatcatccca gaaagaaggc gcgccagctc tgcaggatct tcaagtctgg ggtgccacca | 4920 |
| gcaagcgacg gtcctccatg ggctcttcac cttacggcag tgtccagagg caccgccagt | 4980 |
| cctctgctcc tatgctggtc ctgctgtccc tggcaaaagg agccagagca ttctctccag | 5040 |
| gcctcccgag gaggctgctt cctttgtttt gcagatggag gctcccatcc tttgttctga | 5100 |
| atcaatgtgc tccaaagata agccccaaga aaacagttgt tgccttttga cactgacaat | 5160 |
| tagaatcgtt ggaaaatgga gaaacagga atggcaaat ggtttcagtg accaggagga | 5220 |
| aaccgtgcct gaaagttgct gcttagtgac tgggacactc gctttctgct ctcttatgaa | 5280 |
| ggacagccta ggccgtgtgg cctttataa acaaagctat gaagggtcg tcaaattttc | 5340 |
| tagggctgca actgtggcac tacgtcctgt tgtgccaggt gacactgaca agcagcactg | 5400 |
| agttctatgc aagcccaggt gtgcttctct catggtgacc cccagagaac taaggcccag | 5460 |

-continued

```
ctcttcctct gtcacacccc tcccagcccc cactgtcaga caagggacca cattcacaga    5520
cagtctcagc caagatggca accttggaag tcctggggat gcctttctag aagctttagg    5580
ctgacgccag ggagctgtaa agccccacc tgtccctggg ggttgtgtgc tgggcaggag     5640 agagggaaa gagcccaaac tccaccactg cctgctggca caactgagcc cacgccaggc    5700
actgcaccag cttcactcac cagctaccac atgctaatgt ctcctgttta cccaggtgca    5760
atcacctgag tgctgctttc tcaccactgc atgggaagaa cgatctcatt accaattcaa    5820
ccacttaagc aggcaaaagg actccaacgg gggaaaggca gaggacaaac gattcgggga    5880
ctgagacaga tgcccacaaa atgttcctgg attttagccg gattcgggct gaagttcctt    5940
gccctatgag cccttggagg agagcatcct gactcagaca agaattcaaa tgacaagact    6000
tctgggggat ggcagtgaat ggatccaaag ccttgtttta aaagaatgt ggaggaaggg     6060 aggaaggaag ggagggaagg ggagactgag agggagagag aataaagaag aggaagagaa    6120
ggaagaggag gaggaggaag gggagggag aggaaaaagg ggagggtaga ggaggaggga     6180
gaagggaaag ggaggacaga agagggagg gagcggggag attatctacc cctccatgct    6240
agggaactcc tgtctccttt tccagcagac actgctccat gagtgccccc acagagagcc    6300
agcctgccac acagcagaag gtgctcagct atctgtccca aaggttgagc actagtgtat    6360
accacaagga aaaaaccctt cttttgtact gtttggaagc cagaattaga aacaactcgt    6420
tcacccttct gactttccct ttgcaatgac aggaagatag tatactgcat gggaccacca    6480
cacattcaag atctgagttg tggggacccc caccccaca tgggtggagc cccctgagac      6540
ccgtgggctc tgactggcca tggcccatag atagtgacaa catacacact gctatctgaa    6600
gcctagttgg aggacggatg gatgctttta ggaaaaaatt cccttagtc gtccctcaga     6660 aactacaacg gcttcctaaa atgaatggca ggcaagtttt gattgtttcc taagttcccc    6720
ctaactctca gagcctgtga ctcagcttct ccagaatgcc tgcagggagg caggaccact    6780
gggagtaatg agcacgaatt gggccacttc tcccagtgga ctgttaacgc cgagatctgg    6840
ggtggaaccc actgaacacc tgccctttg cgttgcccag aatgcagcca gagggatacg     6900
ggccacagta actctggggc ccctgaacct accttcccaa gaccctgacg ggaaggtatt    6960
gcttacatga cagtccagtc agtccctctg tcactcagtt aacaaacatg gtcatgggtc    7020
tactatgggc caggctctgt tccgggcatg gggataacac cgtgtgtctc tactcttatg    7080
gacacaagta aatcaatcaa agcagataat gttctaatga ccacccagta gggtgaaggg    7140
atggagggtg ggcaggtgct ggcagaaacc taaggtcaag tcatgggacc ccaatgggga    7200
actggaaact gccacaccat tttctatgtt aggggtcttt ccttgccctt ctagagacct    7260
cacccatggt aatgatgctg ccctcaggtt tgaactggtc tgaagctgtc actggggct     7320 tcacaaaatg aatgccactg aaagcaaacg gcagagatct gtatatgaaa ttcttttac     7380 cctttgtttt ctgtcttccc acatgatcta tgactgctgc aaactctatt ctgactcctc    7440
ctcagtcttg gccggtctgg gaagaacttg gtttagatgc tgggaatgat cccgggcaaa    7500
ggaaacaaat atatttccag cttgcttttc ttcttcccct gtggtgcctg catcctctgt    7560
ctcgcactga ctcacaggct ggactgacaa agtggctgtg ttgacaggga ggatttagtg    7620
gatgccaggc ctgaccctca aaggccctca gtgggggcca atttccaagg ttcttagaga    7680
agatttgggg ccacaaatct gctctgccac ttcactgctg ggtgaaagct gttggcttga    7740
gaagagagag aataggtgag ggacaataat tctcaaggca agctagctga tatcctttca    7800
tttgtggctt ccaaagacag ggaaaggcaa ggcagaccag ggtggaaaca gcgacatcct    7860
```

```
gagggggacga cgtccgtttt gctaattctg tttccctggc agctttgtgc tggacaagat    7920
ttctctggtt tcagctgaag agtgaacagc tgaggagctc tgtgactctg agagagagag    7980
aaatcaatag cccttgaaag gaaagcactg cttgttcttc caggccaggg caggcaggat    8040
aaagagaaca aggctgtaca taccaaagcc gaatttccat taaaggccag aatcctggga    8100
ggcccttttca gcttaatgac catcttctga tcactatcac ttagaaaatg ttcatgtctc    8160
cagttttctc tgcagatagt gcagacatcc tgtgcacatt gatattttat gcaccagatg    8220
caattctctg caaaggtccc ctctggctgg tgtccatccg cttgctctca tgaccactga    8280
tgcgactctg ggggcaagtc aagccattcc ttctagactc tagaatctag aggatgatcc    8340
caactcacag gcctcttgga caagcttgct ttggattcct tctgcctgta ctacccagac    8400
tgccagtcct ccagcaggc aatccaactt cctgcctcta gggtgtggga gtcctgggcg    8460
gggtttggaa tccacagcag atggctggca ggagaggcag ttcccgagca cccactaggt    8520
gccaagcagg caggtatcag gtgcagggct cggaggtgc agaagcacag ccctgtccc    8580
cctcaggttc ccagtctggc ctcagggaca gacaggcagg taggtatgga acggggtac    8640
tggaaggcat acagctgagg gagagagcag ctgcaccctg gtcaatcccc cactcatttc    8700
cctggaggtg gggctgaggc acctggagca ctctgcttgc ttgggttgtc cctttgccaa    8760
agaatgccgg gcagaaagta gagaacaagc aggcccagga agcactagaa gtccctcatg    8820
ggtggacaga gctttacctt cggagctgtc acctcctgtg ttcctcccaa caaccctgtg    8880
aggcaggcgg gcaggctgag caggggactg tgccccgttg acagatgagg aaagcgaggc    8940
tcagggggaa gtgacttacc tgtggcgtcg cagctaggca gtagtggagc gggcacctgc    9000
ctccaggcct tcggatccca gctgccccag ggcgctgcct ctgaggtgct gtacgaggag    9060
gtgactcggg ccagctcatg agcaaaggag ctgccgggca ggaaggactc actccccagg    9120
gcctggcagg acggggggctg tcgcccgagg ctgacctggg ggtgcctggc ttccccaagc    9180
ttgcaggctt tgtctacatg agtctacaac aaccgattga acaatccatc agctgcttgg    9240
ccacaaaatg gttctgactg atcttgtcac tgccctgagt gtctagctgg gtcatctggg    9300
tgttgtggtt atacccacca actgctttgg tggaacgaaa ccgcggccgc gggatcattc    9360
ctggactcag attgttctga agaagcccag ttctgggtgg catcaagtgc ttgctagatg    9420
gggggcttgc cttgatccgg ctacacttgg aggtgacttg ttcttggacg gctacataca    9480
gaaagagaga agtggggatg agttccaaag gcatcctcga cttcggctgt ggccaccgga    9540
gggtagctcc tggcccaaca cggacttctc acctcccgcc cttggctctc tactgagctc    9600
ccccctgctc cccaattcct cgccattccc ctcatttctc tgccctcagc ctggactgca    9660
gttcttctgg gaagctgccc caactcccta ggtctgtgct caccaagagc agatcacact    9720
ggactgaaat gccagctgat ttgtctcttc aagaaaattg gaagctcctg gaggtcaggg    9780
tccatgtctg cttttacact cagtgctctg tatgcaggcc tggcactgcc cacccttga    9840
cagtggtgc atattttgta gaaggaagga aggggccagg tggggtgggc tggctggtg    9900
gcgggagcta gctcagcctc ttagattctc tacccgatgg atgtgacctg ggacagcaag    9960
tgagtgtggt gagtgagtgc agacggtgct tgttccccct cttgtctcat agcctagatg   10020
gcctctgagc ccagatctgg ggctcagaca acatttgttc aactgaacgg taatgggttt   10080
cctttctgaa ggctgaaatc tgggagctga cattctggac tccctgagtt ctgaagagcc   10140
tggggatgga gagacacgga gcagaagatg gaaggtagag tccaggtgc ctaagatggg   10200
gaatacatct cccctcattg tcatgagagt ccactctagc tgatatctac tgtggccaat   10260
```

```
atctaccggt actttttttgg ggtggacact gagtcatgca gcagtcttat ggtttaccca    10320
aggtcaggta ggggagacag tgcagtcaga gcacaagccc agtgtgtctg acccacccaa    10380
gaatccatgc tcgtatctac aaaaatgatt ttttctcttg taatggtgcc taggttcttt    10440
tattatcatg gcatgtgtat gtttttcaac taggttacaa tctggcctta taaggttaac    10500
ctcctggagg ccaccagcct tcctgaaact tgtctgtgct gtccctgcaa ctggagtgtg    10560
cctgatgtgg cactccagcc tggacaagtg ggacacagac tccgctgtta tcaggcccaa    10620
agatgtcttc cataagacca gaagagcaat ggtgtagagg tgtcatgggc tacaataaag    10680
atgctgacct cctgtctgag ggcaagcagc ctcttctggc cctcagacaa atgctgagtg    10740
ttcccaagac taccctcggc ctggtccaat ctcatcccac tggtgcgtaa gggttgctga    10800
actcatgact tcttggctag cctgcaacct ccacggagtg ggaactacat caggcatttt    10860
gctaactgct gtatcctagg ccaataaatg ttgatcacat ttatagctgc catggtaggg    10920 tggggaccccc tgctatctat ctgtggaggc tctgggagcc cctgacacaa actttctgaa    10980
gcagagcctc cccaacccct tttccattcc ctatacctga cagatggccc aggaacccat    11040
tagaaatgga aggtcactgc agcagtatgt gaatgtgcgt gtgggagaag ggcaggatca    11100
gagccctggg ggtgtggcag cccccaagtg attctaatcc agatcctagg gttgtttccc    11160
tgtcccattg aaatagctgc tttaaggggc ctgactcagg gaaatcagtc tcttgaatta    11220
agtggtgatt ttggagtcat ttagaccagg ccttcaattg ggatcctgct cttagagttg    11280
gatgaattat ttaactgatt ttcagatctc ctctttctca atgctttcag aagcacagta    11340
actgcttact ctgaaatgaa ttctcacccc acttccacat atgcacccct tgcccacccc    11400
tttgggaaca ctggccttaa ctgcttacct tcaaatggac tcatctgttg ggagatatat    11460
gcattctgcc gttcagggt cattgccata agacctgatc tctgttcctc ttgctaaaca    11520
gaagatgaaa aagacaaatt agattacagc taccaattaa taattagcct taggatcgct    11580
gcgtggggac ctaggacttg gctttggtgc agcagaaagc atgaataaac acaccagcat    11640
acactcgcat gcatgcccca ccctctcgag caaaattcca caggtataaa taagtaaga    11700 ttctgcacct gggttaaaaa cacaactgca acagcataga atggggcagg agagacagaa    11760
cttaatagca agagcacaca gaaaaaagtt ttaggcattt tggatgtcca tctgctcagg    11820
atgggtcagc agtgagatgc ggtcaccaaa agaacaaatg taacattagg ctgcattaat    11880
agaagcagag tatgtagaag gagggaggtg acagtcctat gctaactctg ccttggccag    11940 actatacccca caggagtctg ggcatgccag tctcagggag acccagacag actggctgca    12000
ttcagaggat ggtaagtaat gagagtgggg attggacttc aaactaccca gacaaagaat    12060
ggctgagcaa gccaaggatg ctgtggctgg ggcagagcag actgtgggct atgtagtggt    12120
ggatacctag cctctgcagg gctgtcatag ggaaaggaca ttgagaagag gactgaggct    12180
tgttcctggt ggtcctggca tgaacggcca gatgatcaca tggtcaggtg gacacagtct    12240
ccaacactgg gagtagccaa acacttactg ccaacctccc gcccttctcc tgactagttg    12300
cagcataggc aattgggagg agcttcctgt ctccatctga aagctggctg ggtgggcagg    12360
gggaggagcg agccaagttt caaggccgca gtttcagcac tcagtctggg atcggctcaa    12420
ggagcaaagg ggaagaacat agccaggagg gaataacatg aaggccccca gacccagaaa    12480
aggcatgact tgctctgaga ccctcagccg gttggtgtca ggttgtgact cggatccagg    12540
tctgactccc agtccagtgc ttgaagcctc accccacaca gtgaggggag cccggccatc    12600
tctgctcaac tgctgccatc tctctccct tctcaaccac caaggcagct ctgtctggga    12660
```

-continued

```
gcacaagctc caagtccact ttctggtctg tgtccccccc aagatgccag aggacttgcc   12720
tctacaacac gggctgcccg tgcagtgcct gcttttccag caaagggctt ctgggaaccc   12780
ttctctgcac tcagtggggc tggtgggagt ggggcgggt agcgacccag tgcttgggac    12840
tgtgcccagc tctcaggcct ggcagcagtt cctggccttg gttcctgcca aggcagagag   12900
gacaaacaca tggcaccggg aagactacac cagaagcgat ccaccagac tggggtttgc    12960 ttttctatcc cgcccttagc ctgcttcctg tcctggtccc tgcctccccc tccactggag   13020
ctgccgtgtg ggcagtgagg ggctgttcct cagctgccct atggagctgc cctctccctg   13080
ccaaagcatt ggcaaggcgg caaggggtgg gggtgggat gggggtggg atctgccttc     13140 tcaagctctc attatactga gcacgtctca cccattattt tatgtcatct agcaacaccc   13200
catgtggaca ctgaggagca tggggtcac atgaccactg cccaaggcca caccatccgg    13260
atctgcctga gatggtcagg gttggcagcc atttctgaag gcagtccttt cgctttggct   13320
cttcttgtac cagtctcagg acatcagggc agaagatcta cagtcccag cttactgatg    13380 tgacagcaga ggctcagaga ggttaaatga cttgcccaag gtgacacggc taagaagtac   13440
agtatctcct aactgcagac caggtgcttc tgctgcttct ggggacagat tcctgcgtgg   13500
ctggctaggt ctaaacggtc cttaactcca tccccaccgg ttgctgcatt agtttcatca   13560
aataacacag ttgtacagag gtaggggttc aggggcaggg gcagatggag ctggagagt    13620 gtgactaagg aaacagcagg ggaagtgcgg taaagtccga agggagggac ggaaagagaa   13680
agccaagccc aggggcgtgc cagacaaaag gaaaggccac gccggggcag ggcaggcttc   13740
agcgggtgct ggggcgtctt catcccggga agcacacatt ccagaggacc ccggagtcta   13800
atggaaaagc tggccagcct atcactatgg aaactgccaa ggccacacag cgctacgcgt   13860
atttaaatgt gctggagtgt tgagatactg tagtggtggg atgcttaagt gctggggtgc   13920
tgggtgttgg gatgcctagg tgctgggtg ccgagatgct ggagtactag tgtgctggga   13980
tgctgaagtg ctgggtcct gagatgctgc agtgctaggg tgctgagatt ctgggctgct    14040
ggagtgttgg ggtgctggga tgctggagtg ctgagatgct tggacaatgg ggtgctggaa   14100
tactatggtg ctggggtgct ggggtattga gatgctaggg tactgggatg ctgaagtgct   14160
gagatcctgg agtgctgggc tgctgggcca caggctcttg aatccattcg tctgcccagg   14220
ggaagaaacc agaagataaa gagctaatga aggagctttg gttgagaggg aggaagtaat   14280
ggaaggagca acatcttgtg gaggagcagg agagaatgga cctcaggttg ggagagaggg   14340
ccaggctaca ggccagagag gcagaaggat tccagcagag tgtgggctcc aggagccaag   14400
gggaaacagg tttctgggag gagagagtcc agtactgctg aagtggcaag tccgctgagg   14460
accaggaagc ttcatttggc tttatgacca ggaggaattt ggaactgtga ctagagtact   14520 taggggaag gaggcaagac tggagccaga ttgctctggg ttgagggtg agtgggaggt     14580 gaagcagggc actgtcactc ctttgaaggg tggcagagag ctggaattgg tgctggatgg   14640
gctgtggggt gacagggtca tgtggaaagc ccctgggggg cacctggaaa aggagaagct   14700
gacagtacag tgagaggaca gctaagggaa agcggaatgg cagaacacgc actgccagga   14760
ggaatgagga tagggtcagg agtgccaggg gcagtgaggc cagcctgggg tcaggtggca   14820
ggacgtgtcc aggaagctgg tctgcactgc agcccacact ggctcagcct tgaggttccc   14880
tgtgtggttg gggtaggaag ttgaaccctc tgggaatgga agatggaacc agctctgcga   14940
gccaagctca gcttttatct atgggtctct gagggctggc agagctgagt ggggacaact   15000
gtgatccgtg aggctctcag gttgaggtgg cccctccggg agggcttcat tttcccagcg   15060
```

```
ggtaggttct aagcagcagt ggctgggcag gtgggtccaa cacagagcca gagaagggtg   15120
aatgggcctc ctggcacccc accectgctg ccectgagct cagtgatgga gggggacagc   15180
acagctgagc ccaagtgctt tggtgtggcc ctgagggaaa gctgcagcct gcctggggcc   15240
tggcatggat gggacacttg aggcagaggg acaatagtgg gcgctgcagt gaggctggct   15300
cttggagagg tttcctgagg agtgctgcct gagacgggca gggagaacag agacaaagtt   15360
ggtgacaggg aatgaaagct gactgaagga ctttacccag acctatgagg atatctctct   15420
cagcaggaag caggagggga ctgtgtgagg actggccaag agctggagtg ttgggaaaat   15480
gactcttcct ccgaccectc tgtcctagct ctggcccctg actgcggag gtctgcttcc     15540 acccccattg gtcgatcgtt gtcccttgtc acagccattg agaattttgg cagggagcat   15600
gttcttagag catttttagg ctctgcggga cataacagct ctgcctcaga gcacatgcct   15660
ttctcagctc ctgaaagcca ctgatcaaat tggaacattt tgtaccttag ggatgaggat   15720
atcaactctc ccagccactt agagggataa atgtgatgat gcattcaatt gtgactacat   15780
ctgatcccaa ctgttgcttc agctgctctc ctatagcaca tggcgggagg cgtgcatccc   15840
agtagctacc tccccacttt tggggagatg tggttccatc catgaaacct gggtacccgc   15900
ctaccaggtc ctggcctatc aggtggcagg gtctggtcaa agaagggcat gtgtggtctt   15960
cagcaaggga gacaggacgg tggtgcagag cgtctagacc ctcagggcaa gtctccccca   16020
cacctgctcc cggggcagtt gtctttgtga cctcccatcc ccctctgttt catcctctat   16080
aaaatgaggg gctgagcccc aaaataacag gcttctttgc catgatgcaa aactgctgaa   16140
tctttctttc tgacacacaa ggcatcgagc agcctctgaa agaaccaaag ccactagcag   16200
gcttcctgac ttgggtttgt aggtactgaa tactcccttg aaaaataaaa acatagaggc   16260
acttttctcc tggctgtttta ttacagaacg aagaaaaaac acactggctt gaaacagacg   16320
ccagatttca aatgtagagg tgaaatacga ggtggcaatt aaaatgtgat tacagaaagt   16380
ctggacactg agaaaagttt acaggacagt gggtgtgggt tttctataac agacacttaa   16440
atatacatga cgataattgc agatagaaac catcaaagac aaaccccaaa tcaactaata   16500
atgtttacag atgttccccc ccaaaccaca gagccttaca tcaaaacaaa tactgaaagg   16560
ctttaaacca ggaacagctc gccttaaccc cacgagggtg cacacaagct gggcttttc    16620 tctcggtctg aatggtaaag ggaggaggat actctagctc ctccaggtgg attgctgaga   16680
cagggctcgg ctcacacact gtctctgcgc ctctcccaaa tctggagaac tctcccagcc   16740
tcctggtaaa gtgtctctgt ggggcactta acgataaaac agcttctgct gtaaagctca   16800
ttaggaaaga gctagcggag actgaaaggt tcgcaaaaga gattaagaat cacacaaggc   16860
aataggattt ttagtgaaca tagaaataaa tggccaagtg gttttctatt tggcatttgt   16920
caacttgcac aacaactctt ggtcatatcc acattgctca ttgcattaaa accataagcg   16980
actcagccac ctagcttaac aaggtatcac tggagcaaaa acacggtct gcatatttgt     17040 aacattgtat aataaacaca aaacaatgca tagtaaacac aactctactg aaacaaaagc   17100
cgtcgcttta tttacaaagt cacaaaatga agtataaata cttctgtcat taatgtttag   17160
gaaaaccatt tacaaaattt tcaaatatgt acacgtagct tgaaaaatca ccagctttcc   17220
attttgtcac aggtagagag agggataagc atgggctgac aacaccactc aaattgtaac   17280
gggagacaac tgcgggtatg gatcgacacc acttcctaga gtgatgtcac catgggggtt   17340
tctatgggca tcctgctcag attttaaagtg ccccagcatc ctgggtgact tgcccagaat   17400
tctgggctgt ggcattttga gcagcagcat gctgttccaa aatgtcgtcg atcagcctca   17460
```

```
agttgcacac ccagtcttca tctgggctca cacaggagcc tttcaagaga gcttcaatga   17520
aatctacctc attgcagtca ggtgacgaaa tcagatcatt tagtgggggt tggggctggc   17580
gcaaaaagtc ggcaggtggc agctcagggg gaatatccgt tctgtcgaac ggacctggga   17640
actggctggc agcaacggca gaagcagcag cagcggtggc agcagcagcc acatagcttg   17700
gtggctcgat gccctgtatg gggctcaggg gactaaagct ggccatacccc tgctggagga   17760 acttggtggt gtttgctaca ggcaccgggc cctgtaccgg gctctgcctg aggctctggc   17820
tgcccagcag gctgaagctg gggttgttgg ccagggcac ttgtgttccc atcgcagcgg   17880
gcacttgtgc ctcccaatca gatggcctct gaaggcaggc ctggccagaa ggtgagtgct   17940
gctgaacgct attatccact tggctgaggg gtgttttccc cgaaactgct gtggtcacag   18000
ctgctgccgc tgtgacccat gcagcattgt tgaacgcagt gggcattctt ggcacactag   18060
gccgtctgag ctggtgggga ctcaaggact gggtgcccag ggagctggga cagaacccag   18120
gcaggggcac ttctggtggg gtggccttgg ggctctgcat atgctggcag acagagtcaa   18180
gtctgcccag gggagtctgg cctgagtgtg agaggatggg acactggggg ctggaggtga   18240
aaattccttg ccgcttcccc agagttggtg agatcactcc catgcccggc gcgcgcgtcg   18300
acacgacagg gacatactgg gaatgcgccc ttgccgtgga ggcggggacc cggcagcgct   18360
acgtatccga catcaacctg tatccagcat caacccgcca agttcactaa cttggtaggg   18420
gtgaggttag ggatccttag gagcccaggc agccagactt tctggggagc ccattcccat   18480
ttgtgttgcc aaagtacccc cagcaggttg tgggaatgtt gcctgtgaag agagtctgtt   18540
ggggtgagat cttgtgtgtg tgcacagggt gacagttgtg tcccatttcc cgggaagctg   18600
tgatggcagc agaacctaga ggagcctgag agagtgtggg agagtgggcc tctggaagag   18660
tagaggctgc ggagccaggt gcagggctgt ctgtcaccca aaggaagagg gactgatgac   18720
tcactgagcg tgtgtgtccc ctggtggcag caggccccat agtgaacata ccatacccttt   18780 tctgtcctga gcgatgctcc cagcagtcct gggagatgga acggtcctta ttcggctcac   18840
aggaaggacc gccttaactg gacagacaca gcaaggtgct aaagatgcct tccatcagag   18900
gccaggttgg aagctctaaa gagacttctc ttgctgttct ctcacccacc cccaggttgt   18960
gtgtgtcccg ctgtggattc tcatgtcctt tctgtgcctg gtggtcctct actacattgt   19020
gtggtccgtc ttgttcttgc gctctatgga tgtgattgcg gacagcgcag gacacacata   19080
accatggccc tgagctggat gaccatcgtc gtgccccttc ttacatttga ggtaagcgtt   19140
ccacgggaag cctcttcagc ccctgaagct tgcgcttccc ctgacaggat tctgcacccc   19200
tagaaaggca gcctctgtcc ctcgagctca cagtgagccc actccaggag aggggagaga   19260
acacagccat ctccgagagg gagcttcggt gaaaggagag catccttcct ttctcttggg   19320
ggcagcacgt ggggctggca gggagaagag tgcaccttt tagccatggt gcctctgtat   19380
ggctccagtt tccactctgg ggaaagcaga gtgggatgtc agatttgtgt attggagtca   19440
cgtggagaat tctagaatgg gagctgttga ctccttagaa caaacacccg gaggagtttg   19500
ccataaaact gctggcactg ggaacttttc aagtggatag gctattgccg agctctgaag   19560
agggacataa aagctcattt cgagcttttcc ccagggatag gtggtttcct gcctttttct   19620
ggcggtgctg atgttccctc ttgtgggagc tcacgcgggg gtggggtggt ggggaggaac   19680
tgcctaatga agtctggctt ccgcctctgc ccatttttcgg tgctggcatc aaccgggact   19740
atgtctcttt ctttagattc tgctggttca caaactggat ggccacaacg ccttctcctg   19800
catcccgatc tttgtccccc tttggctctc gttgatcacg ctgatggcaa ccacatttgg   19860
```

```
acagaaggga ggaaaccact gtatgtactc agcatttcag aagtccttgg tgtgtgtctg   19920
gggggggacc aggggtggg gggtggcgga tagaagtcta ggaagggatg agtccccgag   19980
ggccccaatt tagaagcttg tgtgggaaag tgagggctga ggaaattctg ggaccttcta   20040
agggaagggc atgccgtaac tctggtgttc tgctggcctg caccgggact tttctcgcag   20100
tgcacgctgc catttgaggt agaaccagac acggcaggca acctctcaga gatcccgttc   20160
cctcctctgc aaaatgggga tcaagacaga ttcttcccag gcccgggagg gtttgatgga   20220
aaatccacat ctcccaccca aacctgggat tcatcctagg tccctgttgg ccgctctgcc   20280 tccccatat ccttgctgcc atcacccgag tcttgcctgt cttgccttgc taacactcta   20340
ttcccctcca cctgcttgct gaggcagaca cttccaaaac gatctctgca gagggtgcct   20400
tcctggcaag gctgtgggct ccatggcacg gaagcccaga gcattgccct tcggaaagcc   20460
agtgggtttg ggggcagggc ctcactgcag cccagcagcc cgggctgtgc ttgctgtttg   20520
tgcctctgcc ccctaccccg cacccgggag caggagggg ttgcaccgag ctgacactcc   20580
agtagcctac agagaggagt agtgggactg ggaaagtggc tttaaggtgg ctccatgagt   20640
tcaggccccc tcctggccaa cccgtgcatg actaccgccc tcacggattc cagagggtga   20700
cagaaatctt gttcttgggt ggcactgtca tccatgagtt tatcctggct ggagaagatt   20760
agcggaagac accgtagtct gcgcaccaca gatattttga gactcactgg agcagtagtt   20820
ctcaaatttg ggcatccagc agaatcccaa aagggccagg aaaagggac cgctggagcc   20880 cacccctagcc cgactcagtt tctggaggtc tgggctgggg cccgagaatg gcatccctaa   20940
ctaggccccg tggacgctgt ccctgccggt ccgggaaccc cactccaagc accacagagc   21000
tagcatttgc acttcttccc catttgggt actcaagccc tgttcaggct ttgtgactca   21060
ggagtctgga taaagtatgt tatgacattg taggagtgaa acttcttgtt acggaaagaa   21120
agttaacagg aaggtcagtt gagcctcgtg tgtgaaataa aaaattctta tttttcaggg   21180
tggtttggta tccgcaaaga tttctgtcag tttctgcttg aaatcttccc atttctacga   21240
gaatatggaa acatttccta tgatctccat cacgaagata atgaagaaac cgaagagacc   21300
ccagttccgg agcccctaa aatcgcaccc atgtttcgaa agaaggccag ggtggtcatt   21360
acccagagcc ctgggaagta tgtgctccca cctcccaaat taaatatcga aatgccagat   21420
tagatgccac ttccggggac agagcttaag tggactggga cgcactctct ccgccttcct   21480
ctgccccctc gttcaccccg cagaccagaa ccagtactgg agctgggtct ccaggtacgt   21540
ccatctcatg ccttgtttgc atccagcgcc tatcagccac tcaccacgac gggacgcgga   21600
agtggcaggt gacgggggtg tgtgccagca gatgcggatg ccaggaagag tgtgagaaca   21660
ggggtgggat taccgtctgt ctgggagggg ctccaggtac ccctcttccc cgtcagaccc   21720
actgggagat ggctgcttgc caggccccca gaaggaacat ctgtctatac ggtgctgaaa   21780
tcccaatcaa aagtattgtt tagaaatgta tttctccaca gggctgacct cctgcagctc   21840
gctgagcact cccaggtcct cagcactccc aggtcgtggc tggggcagtc agtaggaact   21900
gtaactatgt ctctgatgca ccacgtgttt agacacagca cagtcctttt ttctgttcct   21960
actgtggaag tagtttctct ttgggcatgc tgacagcagt ttttcatagc ctcacggatg   22020
agccctttct acgggagtga ctccatgctt gtatacagag tatttataca aatgttttag   22080
catcttcata tgcggtgtta acccctagtt ctgtacagca tattctgttc aagtatttt   22140 ttacaagctt gtgctgtagg cacatgcctt ctgctgcaga agtggacgcc cgtggcacac   22200
tccccccccc ccccgtggg gtgccacgcc ttcatgggac attgccactt ctgccctgga   22260
```

```
actcgtgcag gtacgtagta gctgctactg ccacaacggc aacaccaagc aagagatggt    22320
ccatgctttt ctgacgttct cagaatagtg gctagcttca aacctgacaa gcgctgcttg    22380
aagccggaac actagagaat gttgctgaga gcagaaacgg ccacgcgggt cacgactatg    22440
cgtgggaaag tctcaagctt ccctcctgcc agcaacaaga aggctttgga gtaggcatga    22500
tgttttcacg tgtgcgtgcc gtttctccaa gcactgcagg ttccaccgtg tgtcagaggc    22560
tgcaagttta acatcctcct gcctgaaaac aaataggtcc tttgctgaaa agagggtaaa    22620
aaaagagctt tgatcttctc agccaggaga agagggtggt gttttcacgc gggcaactgc    22680
tcgccggcct acatggggtt aattcaagtc tgctgcgagc acgactccgc ccttggcact    22740
ggcctccagc aagccctgtt ctctttgggg tacaggggaa cgggatggtt tagactttcc    22800
tgctcagtgt gtaaaaaatg tagctaaagc cactattttt gctctcctta agctgttcaa    22860
taaaccggtt cctcatttta cacgtgcatg atgtgtatct tctttgctgg atgggccagg    22920
aaactggagt ggtcctctca gccagcctca gaggaaagaa atctctagct ggcacaggca    22980
gccagtgagt gaggctggcg gctgcagggg cacagccttt agaatgagtc cttcagtgca    23040
caggtcccag ggtatacggg gtagtgggag gaaggagggg acgcctcgca gatgccactg    23100
ttggctgggc tacaccttgc cacacttgtt actgcttagg aggctttctg gagtgttcct    23160
tgggtgctac gacaatctgc agcagacact gtcctttcac cgctcctggt cctcgtttgc    23220
tccccagtga tgtcaacagc tgaggactgc tcacgctgca acaaaaggct ctgcagtcgc    23280
tgtctagctt gccctagtcg tctctagagt tctgcctgaa ctgaaactca agtggggttc    23340
agctcatgac ttgtggcaat tgaccaggaa attcaccagt tgctgtggct ggaaggattt    23400
tcagtcctgt gggttgtaac cagaggccac aggtggattc tgccttaggc tcatgagatt    23460
tccgacttgc tgttgaagaa aatgccttgt gaagtgacaa cagtagctct gacccaactg    23520
ccggtgcctc gctagttcct atacgtccca ctggatcctc acagcccggg gaagcaggtg    23580
ctactactct tatccccggg aggagacaga ggccgagaga ggttaagtga cgtgcccaag    23640
tcacacagct cggcagcggc cgggttgagc atcagcagtc tgtttgcaga cccctcactg    23700
tcaccccctg agccagtgcg ccttgggccc tgcggtcagg atgtctcaag cgtggaggca    23760
tcaccggttc gtggcagtct ctggaaggtc actgagctct gtgcccagaa tcgagtcggg    23820
ggagtctgtg cagaggtggc cctgtgtgtg gggacagtgt gtgacacaga cactgctttg    23880
gatggacacc tctcccgtga cctcctagca tccaatccca aaggaacaac tgttgcagag    23940
atggaccgct ggacacaaac ccacgtgcgt ttctctggag acactggcca aggaaaacaa    24000
aacatgctcg aaggccaaca gctgcatgcc ccaccgcgat gtgaccgcag acacccgggg    24060
tgtagaaggg tctctgcctg gtgggggac acgtgcaggc cgaggagagg caggaaggag    24120
gctgcctccg actccccact ggactgcatg gcgacggcgt gtggtggggc agtcagctaa    24180
gccatttgcc taaggggctg tcgggcatct gcgtgctggg gaccgacagt gtgggtgtgt    24240
taggaggatc tgtatggagc acattgctgc ctctggctag gacagggtgg aaagggtggc    24300
gtggctacag cctgacccat gggcaccgtc ctacccttttg ttctgtgctt ccgagtgtca    24360
gtcatgtgct ggggtctgtg ggcccatgac tcagacggtg agctctgacc ttcctgagcc    24420
agggctttgc tgtagttgtg cctggctcag gagctctagg acaaggggac cgctccaggt    24480
ctgcatctac ggtgtggcag ggcccctcgg cactcttgtg cactagtgtc atctttccca    24540
ttgaaatgac tgtgaggacc agaatgtgca catgcagatg ggcagctact tgtctgcctt    24600
ggccctttat tacacaactt gctggggtg gagatgccac cccccggcag tcagagcccc    24660
```

```
tttatgatgt catggggctg gttacatgac tgccaagggg tgctgctggc cacactgcac    24720
tagcaagttt gccagatgga ggacaagcga tcattgagta tggctcgctg tgaagaaaga    24780
aattcgagag gacaggatca tggcttggaa agggtgcctt tccctcccca gttgcagtca    24840
gagacctacc ttcacccagc agatccttcc cctgcctggg acgacccggg gtccactggg    24900
agccctaact tgaggctgct gacagaagaa atcgctttcc aacctctggc cgaggaagct    24960
tcgttcagaa ggccgcaccc tgacggtgac gtcccgcccc agggagaaga taatctcctc    25020
tccctcccct ttccacagaa actgtggaga ctggtcagca gcaaccagtt ttcgtccatc    25080
tggtgggatg acagtggggc ttgtagagtg atcaatcaaa aactctttga aaaggagatt    25140
ctcaaaaggg acgtcgcaca caaagtgttt gccacaactt cgataaagag cttcttccgc    25200
cagctaaact tgtatggctt ccgaaaacgg cgtcaatgca ctttcaggac cttcacccgc    25260
attttctccg caaaaaggct ggtctccatc ttgaataagg taatgaacga caagcctctg    25320
gaggggttaa gtcggtgggc tctggggcct ggtcgggtgg aagtcccagg actgcctcct    25380
gggaagtggg cgacctcagg cagggtgtgg ggccatcgct gtgggcctgt gtccccctct    25440
gggtggaggt gacatgaact aagagtgaat gtggggagag ggctgaggat ggtgcgggcc    25500
cctctcgagt gtgtaaaata tcacaggtgc caagtagccg tatctgcgtg tcgtcctccc    25560
cggggccagc catgtcatct ggtggttgct gtgtccccct gactccacag cacattaccc    25620
tgtgaggtga gcaggccagg ggagtctggt atttgtacca ctgtcaccct agctggtgtc    25680
tggagaggtg ctcaagtgga agcactgaag ggcgcctggc gcaggaggtg cagatgctcc    25740
tgctgccctt ggtaggtggg cccctggtgt ggaagagcca gtacccaggg cctccaaccc    25800
agccggggtg cattctgttg ccagctgaca ctgcatgggg gaggcccaga atcttcttcc    25860
ctcctggtct gcaacttcaa agacccttc cgccggccat ggacaccta atctgccatt    25920
ttgaggcttt ttccaagacg gaaaggcccg ccacaacttg gtaaacctTg acgatgtgaa    25980
cgcgagtccc cagcttcctt tggggactgg gacctttcc agaaaggcct cctgggccag    26040
tagagttctc ttgcacaggg gcgtagatgg ttggtagttg tagtccatcc ttgtgacttg    26100
cagtttcctt ttgtttattt aaactttgac ttatagttag agttctactg ccatccttac    26160
tttcaaagag actcccctca cctcctcgtg aggatgaaga gaagagtggg tgtcaagtct    26220
gcaccaagac atcaggagga ggacaagcca gaagctgctg gatcctgtct ggcaccagca    26280
gacactgagc aacaagatca cacgtctccg aatgagaatg accaggtcac accgcaacac    26340
cgggaaccgg ccggtcccaa cacccaaatc aggagtggct ctgctccacc agcaactcct    26400
gtgatggtgc ctgattccgc cgtggcgagt gacaacagtc cagtgaccca gccggccggc    26460
gagtggtcag agggcagcca ggctcacgtc actccggtgg ccgctgtccc tgggcctgca    26520
gcgctgccct tcctctatgt ccctggatct cccactcaga tgaattctta cgggcctgtg    26580
gtggcccttc ccacagcgtc ccgtagtacc cttgccatgg acaccacagg acttcctgca    26640
cctggcatgc tgccctttg ccatctctgg gtaccggtga ccctagtggc tgctggggct    26700
gcacagcctg ctgcctccat ggtcatgttc ccccatctcc cagctctgca ccaccattgc    26760
ccccacagcc accgcacgtc acagtacatg ccagctagcg atgggcccca ggcgtaccca    26820
gactacgcag accagagcac atagagggca gcatttgggc agaatatgtg ctggtcaata    26880
aatgtgtcag aaaatgagta attttctgac tgcacaaaaa agtcttcatg gtctccatcc    26940
ttttctttc tttgcagtcc agtaccccc tccgacatct ttggcttgca tgatagagac    27000
ttcagcctaa cacgcctccc tggaaaagtg cccaggagat actcgagcag gtgctgggtt    27060
```

-continued

| | |
|---|---|
| ttaggaagcc cctcagacat cccgcctcta ctcattaaaa attacctgga gctggccggg | 27120 |
| cgcagtggct catgcctgta atcccagcac tttgggaggc cgaggcgggt ggatcacgag | 27180 |
| ctcgggagat cgagactgtc ctggctaaca cggtgaaacc ccgtctgtac taaaaataca | 27240 |
| aaaaattagc cgggcgtggt ggcgggcacc tgtagtccca gctactcggg aggctgaggc | 27300 |
| aggagaatgg catgaacccg ggaggcggac gtgcagcaag ccgagatcgc gccactgcac | 27360 |
| tccagcctgg gcgacagagc aggactccgt ctaaaaaaaa aaaaaaaaa aaaaaattac | 27420 |
| ctggagttgc tcgctgagtg ctaattgtgc tgctagcatt gccggcctag ggttcacaat | 27480 |
| gactctgtgt tactggccat tccttgtcat ggcggtgcct ttatataaca ggatcttcac | 27540 |
| tttacataca gatgagatca cgtctggctt tgtcattggg ttaaaaagtg cccttgatag | 27600 |
| ttgtggaggt gacacatact accgtcgact cgaatagatc tgctaggcgc caagcttgtc | 27660 |
| agccttacca gtaaaaaaga aaacctatta aaaaacacc actcgacacg gcaccagctc | 27720 |
| aatcagtcac agtgtaaaaa agggccaagt gcagagcgag tatatatagg actaaaaaat | 27780 |
| gacgtaacgg ttaaagtcca caaaaaacac ccagaaaacc gcacgcgaac ctacgcccag | 27840 |
| aaacgaaagc caaaaaaccc acaacttcct caaatcgtca cttccgtttt cccacgttac | 27900 |
| gtaacttccc attttaagaa aactacaatt cccaacacat acaagttact ccgccctaaa | 27960 |
| acctacgtca cccgcccgt tcccacgccc cgcgccacgt cacaaactcc ccccctcat | 28020 |
| tatcatattg gcttcaatcc aaaataaggt atattattga tgatgttt | 28068 |

<210> SEQ ID NO 17
<211> LENGTH: 30115
<212> TYPE: DNA
<213> ORGANISM: Artificial Sequence
<220> FEATURE:
<223> OTHER INFORMATION: Modified adenovirus

<400> SEQUENCE: 17

| | |
|---|---|
| aaacatcatc aataatatac cttattttgg attgaagcca atatgataat gaggggtgg | 60 |
| agtttgtgac gtggcgcggg gcgtgggaac ggggcgggtg acgtagtagt gtggcggaag | 120 |
| tgtgatgttg caagtgtggc ggaacacatg taagcgacga atgtggcaaa agtgacgttt | 180 |
| ttggtgtgcg ccggtgtaca caggaagtga caattttcgc gcggttttag gcggatgttg | 240 |
| tagtaaattt gggcgtaacc gagtaagatt tggccatttt cgcgggaaaa ctgaataaga | 300 |
| ggaagtgaaa tctgaataat tttgtgttac tcatagcgcg taatatttgt ctagggccgc | 360 |
| ggggactttg accgtttacg tggagactcg cccagtgtgt tttctcaggt gttttccgcg | 420 |
| ttccgggtca aagttggcgt tttgattcgg ccgcttgggt catagacttc tttgagaacc | 480 |
| agttataagc tatggtttct ctccacagaa aaagcactta tggtgtctcc ccctttccag | 540 |
| cccaccaaca ttttacatct aatttggggg ggttttctgg accacttaat acccatccat | 600 |
| ggatctcatg tgaagactcc cctggcttga gaaatcactg tcttgttgaa aatgggaaca | 660 |
| aagctaagtc agatagctgg ttcatcagca atgactttga ccaagcctga tcccacccta | 720 |
| cccccacccca ccccagtgac cacccccac aatggagcac acaactctaa actggtttgt | 780 |
| aggtatgtgt gtgtgaacac gctgaggaat ctgcaaaacc aaatggtgag tgcaaaacca | 840 |
| aacagtcacg agtaaatctc acaacaacca cgtcctgagc tgcagccctt gttgaactat | 900 |
| accccactag ggccccaaga tttaggact tgtgtgtggg tgggacctcc cctttctatc | 960 |
| atgctttaga agacagggat ttcaccagaa ttgaacatat tgaacatatg acccattttt | 1020 |
| ttcagccaaa ggcaattaaa ataacttcat acttgatatc catgtcagca aaagctgcaa | 1080 |

```
aacgcaaatg ggtggctgct aagagccctg gtaccctgac gagcacacca agtgcttagc    1140
aacagtggtg tccaaaggac cagctggaag cctgccttga tgagaagttg ctcttctttc    1200
tacatgaagg aacacctcta ctctcctgct tttaatacct gagctgtgag tgatcatcta    1260
tgtccattag caaacatccc agtggagaag gaaacactca tacccgaaat ctaagctaca    1320
tagttggaat cacttcaact tattgcaata aacacttact aagcacctat tgtgggcaag    1380
tctttgcaat ggataatagt tcagtagata ttttgatgta atatttgaaa taacaataaa    1440
aattgccacc actgaattta ttgagcattt gctgtgcttt aggcactaac ccaggttctt    1500
taaatatttg gtcttattcg atctgtataa atagccatct atgagaaagg gactattatt    1560
gcccttattt tacaaatgag gccaatgagg cccagagagg ttaactaagt tgcccaaaat    1620
catacagccc actagtggca gagcaggatg caaacccagg cttgcctcgt tcccaagccc    1680
acatgtcgtt tgcattggtg tggaggtgtg catgtgttta gtcattagca tgttatatga    1740
taagcaagtt ttgaaacata gaaacttaaa atgtgccatt aagaaaagta caggcaaggt    1800
tttccaaggg gaggtgtgga cctccggaca aattttttaag aactaattat aaatacttaa    1860
aaatgggaat aagaagacaa cctaactacc tgaacagttt tagagatgac tcatgcccac    1920
cctctaaaac ccaaacaaaa acaacaaagt caagaaaacc catgaaatct tagcaagcga    1980
tttctatgta cttgtgaaaa ggatttcttt accattctaa tgggatttat gccaaccata    2040
gagggctcag tgcccctccc atgggtggt tagtgagtac agagctgagc tcaccggcca    2100
tctgcagctt catgttatca agctccagtt tgtccttgga gcaaggttat ctgggacatg    2160
agcagaggca ttgctttctg caatggacag ttctttctgc ctgcatacct agctccttga    2220
taactttaaa taccatttta tagccacact ggagttttga agacctcaat atgcaaatat    2280
tactcaggtt ctgattactt gtctgctcca tgataacaca ctctaaaagc aatgaatggg    2340
gcttatttgt agagaactga agcattttaa gcttttgctc aggaatccct ggtagcttcc    2400
tgtgacttgc aagatattag tgatgggtca agaaacagga ccccccatca gcataacata    2460
cgcagtgcct cagtagtcca tcaggcagaa aaaactgcag atggcacatg gaaatgacca    2520
gcggcggaag atacccgac agtgtgggca gttctatttc agcagcaatc aagaggggc    2580 ctggagccac tcaatcaagt ggagcaggat gggagcaagc actgtgcaga ccaatgcaat    2640
ccccagttaa cacaaaaaat aaataaaaga gatgagattc agtctcttga ctgtgactga    2700
ctgggagctt tatagctgat gcttgtgtct tttctccatt ttatttaatt aggaaaagaa    2760
atgcttatca cacactctac gtgtgaggta caacctccac aggaaaggtt gttaggaaca    2820
tttcaacttc tagaagtttc taaacataag gtaaatccat ctttgtcctt gggatcactg    2880
cacatctcag aaaggcaaat aaatcagtaa ttggtgggca taattactag ctcatggact    2940
gacaaggtct acactatttc gaatctcaca gaagtaagcc atgggacaga tagagtctga    3000
tagtggtgcc ccgtttcctg gaggtcacac ttactcatcc ccctggaccc tgggcttctc    3060
atgattgtca gagagtttgc tggaaccagg tcagcccagt ttcccttccc ctgaaaaatc    3120
ctccaatggc tcgcaccaag actagagatg caagtgcaag cacatccacc ctctcagcag    3180
ccaggttttg cgttccataa tgtcacgtac ccccagtcat accaatctcc ttggagctct    3240
ccagacaggc tgccatgtgt ggtcggccct ctgtgcttgt gctccttggt ttgccaagcc    3300
tggaatgccc tttctccatg attgtactct gggaattctg tgtgtctttc gagatgaagc    3360
tcctccaccc tggaaattct gcctctcttt ccaggtccag ctcctgtggc tgaataccct    3420
tggctgactg aacattcttg ctgggccaag tcttaatcat ctctaaatcc ctctggtgcc    3480
```

```
ccgacagtat ctagcccagg caaagggctc agcaaatact tgcaaaattc aataaacttt    3540
actatgttac tagcttggca tgatgttcta ggcacttggg agattataat ctggtgagca    3600
ttgtgctagt cttttttttg ggataaacac caatgataaa ctgagccttt actctcattt    3660
tagcacatct actcatctct tttcaatgct ggtgggttta taaaacccat cagtagaaca    3720
gagagtgatc ataatcatat ggtgaaaata acatcagcta acatatttac tgaacatgct    3780
ttagtgtgct gggcactgaa ctctgtgcac atgtgaattt gagatagatt gttcctagct    3840
aataagatga ggaagtggag atgggcttac tcaagtcaca caatagcaag atggggtaca    3900
gacagaaacc aagctagaaa ccaagcaacc cctgggtttg gaaatgcatg ggctcctcct    3960
ctgcacatgg cgaggagcag tcaggtgctc ctccttctct catactgaaa taactctgca    4020
cttttggcta ttctgtgaca ctctgtgcta ttctgtagct caaatggctc tggtgcaagg    4080
agctcagatt atgactaacc cccatagata ttcagctgct ttgcaagaag tggatgaatg    4140
ctctggcttt ataaattatt gactagattg gatattggcc caatctccac tctggtgatt    4200
cggaaggagg catatgcaca tttgcaaggt tatagtagtg cactctaatt ccactggctt    4260
ctgagagctt gtaggtttct tgacttaatc attctggaat taaggtaatg gatcctcaac    4320
accttttctt tccctggcct ttactaacca tgtaacagaa atgagcagag aaaacccaag    4380
aaagcgaact ggagacttga tgagtgtgtc aaagatgctc agagtccaag gtcctctgtg    4440
gctcactgac ttcagaagcc aacctccgtt gttcaagtca cttgtgaggt tactatgcta    4500
gagcactaaa tattatccag atagcccaaa gaggtgaagg cagacatgtg gaagaacctg    4560
gattttgggg caagttgatg aatgcctcct gccccatatc aaagagaggt gataggagac    4620
aactttgtga atttgaaata atgcaccggg gaaacaggaa aacgtaatgt aagtcacgct    4680
tcttggcttt tttcttgcca ttaccctact tggccaagtg caaatgggat ttcaatatat    4740
cataagtatg catctattaa taacaatgca agaaagctgt acaactgaag tctgagattt    4800
tgtaagaaac agaatctctg taagcatcac catccaacag aacttcctga gttgatgctg    4860
aatcatccca gaaagaaggc gcgccagctc tgcaggatct tcaagtctgg ggtgccacca    4920
gcaagcgacg gtcctccatg ggctcttcac cttacggcag tgtccagagg caccgccagt    4980
cctctgctcc tatgctggtc ctgctgtccc tggcaaaagg agccagagca ttctctccag    5040
gcctcccgag gaggctgctt cctttgtttt gcagatggag gctcccatcc tttgttctga    5100
atcaatgtgc tccaaagata agccccaaga aaacagttgt tgccttttga cactgacaat    5160
tagaatcgtt ggaaaatgga gaaaacagga atggcaaat ggtttcagtg accaggagga    5220
aaccgtgcct gaaagttgct gcttagtgac tgggacactc gctttctgct ctcttatgaa    5280
ggacagccta ggccgtgtgg cctttttataa acaaagctat gaaggggtcg tcaaattttc    5340
tagggctgca actgtggcac tacgtcctgt tgtgccaggt gacactgaca agcagcactg    5400
agttctatgc aagcccaggt gtgcttctct catggtgacc cccagagaac taaggcccag    5460
ctcttcctct gtcacacccc tcccagcccc cactgtcaga caagggacca cattcacaga    5520
cagtctcagc caagatggca accttggaag tcctggggat gcctttctag aagctttagg    5580
ctgacgccag ggagctgtaa agccccacc tgtccctggg ggttgtgtgc tgggcaggag    5640
agagggaaa gagcccaaac tccaccactg cctgctggca caactgagcc cacgccaggc    5700
actgcaccag cttcactcac cagctaccac atgctaatgt ctcctgttta cccaggtgca    5760
atcacctgag tgctgctttc tcaccactgc atgggaagaa cgatctcatt accaattcaa    5820
ccacttaagc aggcaaaagg actccaacgg gggaaaggca gaggacaaac gattcgggga    5880
```

```
ctgagacaga tgcccacaaa atgttcctgg attttagccg gattcgggct gaagttcctt     5940
gccctatgag cccttggagg agagcatcct gactcagaca agaattcaaa tgacaagact     6000
tctgggggat ggcagtgaat ggatccaaag ccttgtttta taaagaatgt ggaggaaggg     6060
aggaaggaag ggagggaagg ggagactgag agggagagag aataaagaag aggaagagaa     6120
ggaagaggag gaggaggaag gggaggggag aggaaaaagg ggagggtaga ggaggaggga     6180
gaagggaagg ggaggacaga agaggggagg gagcggggag attatctacc cctccatgct     6240
agggaactcc tgtctccttt tccagcagac actgctccat gagtgccccc acagagagcc     6300
agcctgccac acagcagaag gtgctcagct atctgtccca aaggttgagc actagtgtat     6360
accacaagga aaaaaacctt cttttgtact gtttggaagc cagaattaga acaactcgt     6420 tcacccttct gactttccct ttgcaatgac aggaagatag tatactgcat gggaccacca     6480
cacattcaag atctgagttg tggggacccc caccccacac tgggtggagc cccctgagac     6540
ccgtgggctc tgactggcca tggcccatag atagtgacaa catacacact gctatctgaa     6600
gcctagttgg aggacggatg gatgctttta ggaaaaaatt ccctttagtc gtccctcaga     6660
aactacaacg gcttcctaaa atgaatggca ggcaagtttt gattgtttcc taagttcccc     6720
ctaactctca gagcctgtga ctcagcttct ccagaatgcc tgcagggagg caggaccact     6780
gggagtaatg agcacgaatt gggccacttc tcccagtgga ctgttaacgc cgagatctgg     6840
ggtggaaccc actgaacacc tgcccttttg cgttgcccag aatgcagcca gagggatacg     6900
ggccacagta actctggggc ccctgaacct accttcccaa gaccctgacg ggaaggtatt     6960
gcttacatga cagtccagtc agtccctctg tcactcagtt aacaaacatg gtcatgggtc     7020
tactatgggc caggctctgt tccgggcatg gggataacac cgtgtgtctc tactcttatg     7080
gacacaagta aatcaatcaa agcagataat gttctaatga ccacccagta gggtgaaggg     7140
atggagggtg ggcaggtgct ggcagaaacc taaggtcaag tcatgggacc ccaatgggga     7200
actgaaaact gccacaccat tttctatgtt aggggtcttt ccttgccctt ctagagacct     7260
cacccatggt aatgatgctg ccctcaggtt tgaactggtc tgaagctgtc actgggggct     7320
tcacaaaatg aatgccactg aaagcaaacg gcagagatct gtatatgaaa ttcttttac     7380 cctttgtttt ctgtcttccc acatgatcta tgactgctgc aaactctatt ctgactcctc     7440
ctcagtcttg gccggtctgg gaagaacttg gtttagatgc tgggaatgat cccgggcaaa     7500
ggaaacaaat atatttccag cttgcttttc ttcttcccct gtggtgcctg catcctctgt     7560
ctcgcactga ctcacaggct ggactgacaa agtggctgtg ttgacaggga ggatttagtg     7620
gatgccaggc ctgaccctca aaggccctca ggtggggcca atttccaagg ttcttagaga     7680
agatttgggg ccacaaatct gctctgccac ttcactgctg ggtgaaagct gttggcttga     7740
gaagagagag aataggtgag ggacaataat tctcaaggca agctagctga tatcctttca     7800
tttgtggctt ccaaagacag ggaaaggcaa ggcagaccag ggtggaaaca gcgacatcct     7860
gaggggacga cgtccgtttt gctaattctg tttccctggc agctttgtgc tggacaagat     7920
ttctctggtt tcagctgaag agtgaacagc tgaggagctc tgtgactctg agagagagag     7980
aaatcaatag cccttgaaag gaaagcactg cttgttcttc caggccaggg caggcaggat     8040
aaagagaaca aggctgtaca taccaaagcc gaatttccat taaaggccag aatcctggga     8100 ggcccttca gcttaatgac catcttctga tcactatcac ttagaaaatg ttcatgtctc     8160
cagttttctc tgcagatagt gcagacatcc tgtgcacatt gatatttat gcaccagatg     8220 caattctctg caaaggtccc ctctggctgg tgtccatccg cttgctctca tgaccactga     8280
```

-continued

```
tgcgactctg ggggcaagtc aagccattcc ttctagactc tagaatctag aggatgatcc   8340
caactcacag gcctcttgga caagcttgct ttggattcct tctgcctgta ctacccagac   8400
tgccagtcct ccagcagggc aatccaactt cctgcctcta gggtgtggga gtcctgggcg   8460
gggtttggaa tccacagcag atggctggca ggagaggcag ttcccgagca cccactaggt   8520
gccaagcagg caggtatcag gtgcagggct tcggaggtgc agaagcacag ccctgtccc    8580
cctcaggttc ccagtctggc ctcagggaca gacaggcagg taggtatgga aacggggtac   8640
tggaaggcat acagctgagg gagagagcag ctgcaccctg tcaatcccc cactcatttc    8700
cctggaggtg gggctgaggc acctggagca ctctgcttgc ttgggttgtc cctttgccaa   8760
agaatgccgg gcagaaagta gagaacaagc aggcccagga agcactagaa gtccctcatg   8820
ggtggacaga gctttacctt cggagctgtc acctcctgtg ttcctcccaa caaccctgtg   8880
aggcaggcgg gcaggctgag caggggactg tgccccgttg acagatgagg aaagcgaggc   8940
tcaggggaa gtgacttacc tgtggcgtcg cagctaggca gtagtggagc gggcacctgc    9000
ctccaggcct tcggatccca gctgccccag ggcgctgcct ctgaggtgct gtacgaggag   9060
gtgactcggg ccagctcatg agcaaaggag ctgccgggca ggaaggactc actccccagg   9120
gcctggcagg acggggctg tcgcccgagg ctgacctggg ggtgcctggc ttccccaagc    9180
ttgcaggctt tgtctacatg agtctacaac aaccgattga acaatccatc agctgcttgg   9240
ccacaaaatg gttctgactg atcttgtcac tgccctgagt gtctagctgg gtcatctggg   9300
tgttgtggtt atacccacca actgcttttgg tggaacgaaa ccgcggccga tctgaattca   9360
gatcggccgc gggatcattc ctggactcag attgttctga agaagcccag ttctgggtgg   9420
catcaagtgc ttgctagatg gggggcttgc cttgatccgg ctacacttgg aggtgacttg   9480
ttcttggacg gctacataca gaaagagaga agtggggatg agttccaaag gcatcctcga   9540
cttcggctgt ggccaccgga gggtagctcc tggcccaaca cggacttctc acctcccgcc   9600
cttggctctc tactgagctc ccccctgctc cccaattcct cgccattccc ctcatttctc   9660
tgccctcagc ctggactgca gttcttctgg gaagctgccc caactcccta ggtctgtgct   9720
caccaagagc agatcacact ggactgaaat gccagctgat ttgtctcttc aagaaaattg   9780
gaagctcctg gaggtcaggg tccatgtctg ctttttacact cagtgctctg tatgcaggcc   9840
tggcactgcc caccctttga caggtggtgc atattttgta gaaggaagga aggggccagg   9900
tggggtgggc tgggctggtg gcgggagcta gctcagcctc ttagattctc tacccgatgg   9960
atgtgacctg ggacagcaag tgagtgtggt gagtgagtgc agacggtgct tgttcccct  10020
cttgtctcat agcctagatg gcctctgagc ccagatctgg ggctcagaca acatttgttc  10080
aactgaacgg taatgggttt cctttctgaa ggctgaaatc tgggagctga cattctggac  10140
tccctgagtt ctgaagagcc tggggatgga gagacacgga gcagaagatg aaggtagag   10200
tcccaggtgc ctaagatggg gaatacatct cccctcattg tcatgagagt ccactctagc  10260
tgatatctac tgtggccaat atctaccggt actttttgg ggtggacact gagtcatgca   10320
gcagtcttat ggtttaccca aggtcaggta ggggagacag tgcagtcaga gcacaagccc  10380
agtgtgtctg acccacccaa gaatccatgc tcgtatctac aaaaatgatt ttttctcttg  10440
taatggtgcc taggttcttt tattatcatg gcatgtgtat gtttttcaac taggttacaa  10500
tctggcctta taaggttaac ctcctggagg ccaccagcct tcctgaaact tgtctgtgct  10560
gtccctgcaa ctggagtgtg cctgatgtgg cactccagcc tggacaagtg ggacacagac  10620
tccgctgtta tcaggcccaa agatgtcttc cataagacca gaagagcaat ggtgtagagg  10680
```

-continued

```
tgtcatgggc tacaataaag atgctgacct cctgtctgag ggcaagcagc ctcttctggc   10740
cctcagacaa atgctgagtg ttcccaagac taccctcggc ctggtccaat ctcatcccac   10800
tggtgcgtaa gggttgctga actcatgact tcttggctag cctgcaacct ccacggagtg   10860
ggaactacat caggcatttt gctaactgct gtatcctagg ccaataaatg ttgatcacat   10920
ttatagctgc catggtaggg tggggacccc tgctatctat ctgtggaggc tctgggagcc   10980
cctgacacaa actttctgaa gcagagcctc cccaacccct tttccattcc ctatacctga   11040
cagatggccc aggaacccat tagaaatgga aggtcactgc agcagtatgt gaatgtgcgt   11100
gtgggagaag ggcaggatca gagccctggg ggtgtggcag cccccaagtg attctaatcc   11160
agatcctagg gttgtttccc tgtcccattg aaatagctgc tttaaggggc ctgactcagg   11220
gaaatcagtc tcttgaatta agtggtgatt ttggagtcat ttagaccagg ccttcaattg   11280
ggatcctgct cttagagttg gatgaattat ttaactgatt tcagatctc ctctttctca    11340
atgctttcag aagcacagta actgcttact ctgaaatgaa ttctcacccc acttccacat   11400
atgcacccct tgcccacccc tttgggaaca ctggccttaa ctgcttacct tcaaatggac   11460
tcatctgttg ggagatatat gcattctgcc gttcagggt cattgccata agacctgatc    11520
tctgttcctc ttgctaaaca gaagatgaaa aagacaaatt agattacagc taccaattaa   11580
taattagcct taggatcgct gcgtggggac ctaggacttg gctttggtgc agcagaaagc   11640
atgaataaac acaccagcat acactcgcat gcatgcccca ccctctcgag caaaattcca   11700
caggtataaa taaagtaaga ttctgcacct gggttaaaaa cacaactgca acagcataga   11760
atggggcagg agagacagaa cttaatagca agagcacaca gaaaaaagtt ttaggcattt   11820
tggatgtcca tctgctcagg atgggtcagc agtgagatgc ggtcaccaaa agaacaaatg   11880
taacattagg ctgcattaat agaagcagag tatgtagaag gagggaggtg acagtcctat   11940
gctaactctg ccttggccag actatacca caggagtctg ggcatgccag tctcagggag    12000
acccagacag actggctgca ttcagaggat ggtaagtaat gagagtgggg attggacttc   12060
aaactaccca gacaaagaat ggctgagcaa gccaaggatg ctgtggctgg ggcagagcag   12120
actgtgggct atgtagtggt ggatacctag cctctgcagg gctgtcatag ggaaaggaca   12180
ttgagaagag gactgaggct tgttcctggt ggtcctggca tgaacggcca gatgatcaca   12240
tggtcaggtg gacacagtct ccaacactgg gagtagccaa acacttactg ccaacctccc   12300
gcccttctcc tgactagttg cagcataggc aattgggagg agcttcctgt ctccatctga   12360
aagctggctg ggtgggcagg gggaggagcg agccaagttt caaggccgca gtttcagcac   12420
tcagtctggg atcggctcaa ggagcaaagg ggaagaacat agccaggagg gaataacatg   12480
aaggccccca gacccagaaa aggcatgact tgctctgaga ccctcagccg gttggtgtca   12540
ggttgtgact cggatccagg tctgactccc agtccagtgc ttgaagcctc accccacaca   12600
gtgaggggag cccggccatc tctgctcaac tgctgccatc tctctcccct tctcaaccac   12660
caaggcagct ctgtctggga gcacaagctc caagtccact ttctggtctg tgtcccccc    12720
aagatgccag aggacttgcc tctacaacac gggctgcccg tgcagtgcct gcttttccag   12780
caaagggctt ctgggaaccc ttctctgcac tcagtgggc tggtgggagt ggggcggggt    12840
agcgacccag tgcttgggac tgtgcccagc tctcaggcct ggcagcagtt cctgccttg    12900
gttcctgcca aggcagagag gacaaacaca tggcaccggg aagactacac cagaagcgat   12960
tccaccagac tggggtttgc ttttctatcc cgcccttagc ctgcttcctg tcctggtccc   13020
tgcctccccc tccactggag ctgccgtgtg ggcagtgagg ggctgttttct cagctgccct   13080
```

```
atggagctgc cctctccctg ccaaagcatt ggcaaggcgg caaggggtgg gggtggggat   13140
gggggtgggg atctgccttc tcaagctctc attatactga gcacgtctca cccattattt   13200
tatgtcatct agcaacaccc catgtggaca ctgaggagca tggggtcac atgaccactg    13260 cccaaggcca caccatccgg atctgcctga gatggtcagg gttggcagcc atttctgaag   13320
gcagtccttt cgctttggct cttcttgtac cagtctcagg acatcagggc agaagatcta   13380
cagtccccag cttactgatg tgacagcaga ggctcagaga ggttaaatga cttgcccaag   13440
gtgacacggc taagaagtac agtatctcct aactgcagac caggtgcttc tgctgcttct   13500
ggggacagat tcctgcgtgg ctggctaggt ctaaacggtc cttaactcca tccccaccgg   13560
ttgctgcatt agtttcatca ataacacag ttgtacagag gtaggggttc aggggcaggg    13620
gcagatggag gctggagagt gtgactaagg aaacagcagg ggaagtgcgg taaagtccga   13680
agggagggac ggaaagagaa agccaagccc aggggcgtgc cagacaaaag gaaaggccac   13740
gccggggcag ggcaggcttc agcgggtgct ggggcgtctt catcccggga agcacacatt   13800
ccagaggacc ccggagtcta atggaaaagc tggccagcct atcactatgg aaactgccaa   13860
ggccacacag cgctacgcgt atttaaatgt gctggagtgt tgagatactg tagtggtggg   13920
atgcttaagt gctggggtgc tgggtgttgg gatgcctagg tgctggggtg ccgagatgct   13980
ggagtactag tgtgctggga tgctgaagtg ctggggtcct gagatgctgc agtgctaggg   14040
tgctgagatt ctgggctgct ggagtgttgg ggtgctggga tgctggagtg ctgagatgct   14100
tggacaatgg ggtgctggaa tactatggtg ctggggtgct ggggtattga gatgctaggg   14160
tactgggatg ctgaagtgct gagatcctgg agtgctgggc tgctgggcca caggctcttg   14220
aatccattcg tctgcccagg ggaagaaacc agaagataaa gagctaatga aggagctttg   14280
gttgagaggg aggaagtaat ggaaggagca acatcttgtg gaggagcagg agagaatgga   14340
cctcaggttg ggagagaggg ccaggctaca ggccagagag gcagaaggat tccagcagag   14400
tgtgggctcc aggagccaag gggaaacagg tttctgggag gagagagtcc agtactgctg   14460
aagtggcaag tccgctgagg accaggaagc ttcatttggc tttatgacca ggaggaattt   14520
ggaactgtga ctagagtact taggggggaag gaggcaagac tggagccaga ttgctctggg   14580 ttgagggggtg agtgggaggt gaagcagggc actgtcactc ctttgaaggg tggcagagag   14640
ctggaattgg tgctggatgg gctgtggggt gacagggtca tgtggaaagc ccctgggggg   14700
cacctggaaa aggagaagct gacagtacag tgagaggaca gctaagggaa agcggaatgg   14760
cagaacacgc actgccagga ggaatgagga tagggtcagg agtgccaggg gcagtgaggc   14820
cagcctgggg tcaggtggca ggacgtgtcc aggaagctgg tctgcactgc agcccacact   14880
ggctcagcct tgaggttccc tgtgtggttg gggtaggaag ttgaaccctc tgggaatgga   14940
agatggaacc agctctgcga gccaagctca gcttttatct atgggtctct gagggctggc   15000
agagctgagt ggggacaact gtgatccgtg aggctctcag gttgaggtgg ccctccgggg   15060
agggcttcat tttcccagcg ggtaggttct aagcagcagt ggctgggcag gtgggtccaa   15120
cacagagcca gagaagggtg aatgggcctc ctggcacccc accctgctg ccctgagct    15180 cagtgatgga gggggacagc acagctgagc ccaagtgctt tggtgtggcc ctgagggaaa   15240
gctgcagcct gcctggggcc tggcatggat gggacacttg aggcagaggg acaatagtgg   15300
gcgctgcagt gaggctggct cttggagagg tttcctgagg agtgctgcct gagacgggca   15360
gggagaacag agacaaagtt ggtgacaggg aatgaaagct gactgaagga ctttacccag   15420
acctatgagg atatctctct cagcaggaag caggagggga ctgtgtgagg actggccaag   15480
```

```
agctggagtg ttgggaaaat gactctttct ccgacccctc tgtcctagct ctggcccctg   15540
gactgcggag gtctgcttcc accccccattg gtcgatcgtt gtcccttgtc acagccattg   15600
agaattttgg cagggagcat gttcttagag catttttagg ctctgcggga cataacagct   15660
ctgcctcaga gcacatgcct ttctcagctc ctgaaagcca ctgatcaaat tggaacattt   15720
tgtaccttag ggatgaggat atcaactctc ccagccactt agagggataa atgtgatgat   15780
gcattcaatt gtgactacat ctgatcccaa ctgttgcttc agctgctctc ctatagcaca   15840
tggcgggagg cgtgcatccc agtagctacc tccccacttt tggggagatg tggttccatc   15900
catgaaacct gggtacccgc ctaccaggtc ctggcctatc aggtggcagg gtctggtcaa   15960
agaagggcat gtgtggtctt cagcaaggga gacaggacgg tggtgcagag cgtctagacc   16020
ctcagggcaa gtctccccca cacctgctcc cggggcagtt gtctttgtga cctcccatcc   16080
ccctctgttt catcctctat aaaatgaggg gctgagcccc aaaataacag gcttctttgc   16140
catgatgcaa aactgctgaa tctttctttc tgacacacaa ggcatcgagc agcctctgaa   16200
agaaccaaag ccactagcag gcttcctgac ttgggtttgt aggtactgaa tactcccttg   16260
aaaaataaaa acatagaggc acttttctcc tggctgttta ttacagaacg aagaaaaaac   16320
acactggctt gaaacagacg ccagatttca aatgtagagg tgaaatacga ggtggcaatt   16380
aaaatgtgat tacagaaagt ctggacactg agaaaagttt acaggacagt gggtgtgggt   16440
tttctataac agacacttaa atatacatga cgataattgc agatagaaac catcaaagac   16500 aaacccaaa tcaactaata atgtttacag atgttccccc ccaaaccaca gagccttaca   16560
tcaaaacaaa tactgaaagg ctttaaacca ggaacagctc gccttaaccc cacgagggtg   16620
cacacaagct gggcttttc tctcggtctg aatggtaaag ggaggaggat actctagctc   16680
ctccaggtgg attgctgaga cagggctcgg ctcacacact gtctctgcgc ctctcccaaa   16740
tctggagaac tctcccagcc tcctggtaaa gtgtctctgt ggggcactta acgataaaac   16800
agcttctgct gtaaagctca ttaggaaaga gctagcggag actgaaaggt tcgcaaaaga   16860
gattaagaat cacacaaggc aataggattt ttagtgaaca tagaaataaa tggccaagtg   16920
gttttctatt tggcatttgt caacttgcac aacaactctt ggtcatatcc acattgctca   16980
ttgcattaaa accataagcg actcagccac ctagcttaac aaggtatcac tggagcaaac   17040
aacacggtct gcatatttgt aacattgtat aataaacaca aaacaatgca tagtaaacac   17100
aactctactg aaacaaaagc cgtcgcttta tttacaaagt cacaaaatga agtataaata   17160
cttctgtcat taatgtttag gaaaaccatt tacaaaatt tcaaatatgt acacgtagct   17220
tgaaaaatca ccagctttcc attttgtcac aggtagagag agggataagc atgggctgac   17280
aacaccactc aaattgtaac gggagacaac tgcgggtatg gatcgacacc acttcctaga   17340
gtgatgtcac catgggggtt tctatgggca tcctgctcag atttaaagtg ccccagcatc   17400
ctgggtgact tgcccagaat tctgggctgt ggcattttga gcagcagcat gctgttccaa   17460
aatgtcgtcg atcagcctca agttgcacac ccagtcttca tctgggctca cacaggagcc   17520
tttcaagaga gcttcaatga aatctacctc attgcagtca ggtgacgaaa tcagatcatt   17580
tagtgggggt tggggctggc gcaaaaagtc ggcaggtggc agctcagggg gaatatccgt   17640
tctgtcgaac ggacctggga actggctggc agcaacggca gaagcagcag cagcggtggc   17700
agcagcagcc acatagcttg gtggctcgat gccctgtatg gggctcaggg gactaaagct   17760
ggccataccc tgctgaagga acttggtggt gtttgctaca ggcaccgggc cctgtaccgg   17820
gctctgcctg aggctctggc tgcccagcag gctgaagctg gggttgttgg ccaggggcac   17880
```

```
ttgtgttccc atcgcagcgg gcacttgtgc ctcccaatca gatggcctct gaaggcaggc   17940
ctggccagaa ggtgagtgct gctgaacgct attatccact tggctgaggg gtgttttccc   18000
cgaaactgct gtggtcacag ctgctgccgc tgtgacccat gcagcattgt tgaacgcagt   18060
gggcattctt ggcacactag gccgtctgag ctggtgggga ctcaaggact gggtgcccag   18120
ggagctggga cagaacccag gcaggggcac ttctggtggg gtggccttgg ggctctgcat   18180
atgctggcag acagagtcaa gtctgcccag gggagtctgg cctgagtgtg agaggatggg   18240
acactggggg ctggaggtga aaattccttg ccgcttcccc agagttggtg agatcactcc   18300
catgcccggc gcgcgcgtcg acgtgagcaa gtggaatgga gtggcaggga atgagtgagg   18360
gagacaacag ctcagtagga ccttgtgggc tactggaaag actttggctt tgactctcag   18420
tgagataagg aggtatttga aggagtttta gcagagaagg aacaattctg tttatttttta  18480 ggagctcttt atatatttag gaaattactt ctttgttagt catatatttt ggaatttgtt   18540
gttccccgtt tgtcatttct gtttctacat tttgcttata atatttgtct atgtaaacct   18600
taatatgtac ttggttaaat tgataaattc tttgcataat taatagctag ctattgttgg   18660
cctacctata attaattttt gctttatcta gtaataggcc tgaattttca tttgggatcc   18720
agccctctcc ctgacactat gcagggcctg ggagactaaa gcctgctgga ataactcca   18780 gcttggccct gccaaacatt acaacaccta gcacctgctc tccccaccat agtgactgat   18840
ttgggcagga atgagaccac agccactcca agagcccagc tgttggctac cagtaacatc   18900
ttctcctcta aacaggagat ccagctatat tgaaggcttc caaaattacc ctatgtctac   18960
ctgtcacagg aatgttcaga ggactaagcc tctgcctttc tccacccccat acttacttca   19020 tatgaactga tgaatgggca acttcacaat ttattattta cgtcacctag atgcaagtca   19080
gagggagaag caacaaatca gcagtaccta agaagttctc aagtcctcaa ggtgaacttt   19140
acctatatat acaaaatata tttgcctctt tcctttaacc cttttttctta ctcccaccac   19200 tttccaccca atgtgtaata atattagtca cttcatagag ttcttatgag aagttaaatg   19260
aggaaatcat gtaaaccact gagggctggc aacaagttct taataagtgc tattgagtta   19320
tgagtattat tatctcccttt gggctggatt cacagtgtca cctcttctgg gaccatagta   19380
agccaatggt tccagctcct tctattatgt catttaatt tggggaatag cttaacatat   19440
tagatgatcc tttacatgcc tgagcggtct ttctttgatg gtatttctat gatcttatga   19500
agagctagat gttgccgctc cattttatct tgctggtggc agctggtgtt tagccaactt   19560
gtcttttttt ttctgtctct tatattttttgg ttttgttttt tggcagaagc ctgtgttttt  19620
cagattactt tttgcttgtg tctacttttt cccaaaacaa tattacatat taaacttatt   19680
gtatatttaa gtttatttta tgcatcaaaa gtcgcattga atttctgtgc tattgtgggg   19740
caaattgaca tcaatgtaat ttaactcatt ttatcccaaa ttaggctatg tctttccata   19800
tactcaaatc ttcttttatg tccctcaaca gtttccttca tataaatatt gcatatttct   19860
aattaagttt attttttctaa tctccatttt ggatgtctta aatatagtct tttctcccctt  19920 tgctctttat caaagatctg caaactatgg cctgttttg taaataaagt tttgtaataa   19980
agtttaaatg gccactccca tttgtttaca tgttgagtat ggctgctttc agactgaaat   20040
ggcgaatgaa gtggtcataa caagaccata tggcctggaa agcaaatata tttattatct   20100
ggcaatttac aaaaaaagtt tgccaacctc tgctttatat ttttgatcta gttgttatttt  20160 gaaaataaag ctattgatat ttgtatatta attttttacc cagctacctt attgttttta   20220
ttacttaata gtttacagta tttctttttag ttttttccagg tgtaacatct gtaaatatta  20280
```

```
ataaatctat tagctaatat ttcatttagc atttttatat ctatactcac atgagaagtt    20340
ttctttaatt ttcttttgtg tttatcaacc tgtgttcact caggaaaatg aagccactta    20400
agtataccag gagtggaggg tttcatatag aaatgagggc ttatttgaat tttgggaaag    20460
ctgatgaaac aggtcagcag agttactgca gaagaccagg aaagttacat ctggaaggtt    20520
agggaagcag acactaaaga cttaagcctg aagcatagaa gtaaggatcc gtcaatactt    20580
attgagaaac ttctggaatt ctcaagaacc tctgagaaat ctcccattct gtggcaataa    20640
agtggtggta ctcaagccat caccaacatg gctcatatgt ctcattgcac tatgtccaaa    20700
gacaaatggc ctctgcttct cttctgtctc ctaaatctct taagatttcc tcttatttgt    20760
ttaagtctaa cccagaagac ttacatggca ggtaattctg ggaaatgtat tcccttgttt    20820
ctccaaaggg gtgggataa taccaagttg acaacagaaa atctagcacc cttttttaagg   20880 ttttggcatc agtgatttct tggtgctcta aatagttctt atgattattc catgggtgct    20940
taaaaagaat atgtattctc tgatttaaga atatgtaatt gatttaacta ttgattagat    21000
attaataaaa tagatttta aattacctta ttaatttggt taagtcctcc atgactactt     21060
attttttgac tatttgttat ggaaaggtgt agctaaataa atatagaact actctatatg    21120
tgtttctagt tctctatgta ttctctacat tttgctttat aattgttttc tttcttagag    21180 acagggtct tgctgtgttg cccaggccag agtgcagtgg catgatcata actcactgta     21240
gccttaaact cctgggctca agcaatcctc ctgcctcagc ttctcaagta gatgggacta    21300
cagaagtgca tcaccacacc ctgctaattt ttttcttatt tttattttta gtgatggagt    21360
catgctatga tgctcagagt ggtcttgagc tcctggcctc aagcaatcct cccacctcag    21420 cccctgagt agctgggatt ataggtgaga ggcaccatgc ctggatttgc tttataaatt     21480
ttgatatgtt acttggtgca tagatattca ttgctgttag accttcatta tgtgttgtac    21540
cctgcccttc tttggttcac ttttccttga attcagtctt gtctgatatt aattttcagc    21600
tgtctgcttt cttcttattt ccattttct aatatgcttt tgcctactca tttgctttca     21660
attttttctg agtcatttca ttctagatga gtatattaca gtcagtactt aattgggttt    21720
ttctttgtca ctgaatatga gtgtctcttt tcctgtgtat tgatagggta gatatgtgta    21780
gtatgagtgt tacaatttt taaaaaactt tgatttctct cctttgtttt atttggggtc     21840
tccggttatt ttttaaggtg tatagtgtca ttttattttt aatgtttgcc tctgtaaaaa    21900
taattttata ggctgtactt aatcttctat ttatttagct agtttatatt gactcttcaa    21960
taacagtagt aaatgtccct acttctaact ccccttgccc tccaccttt aattttgtgg     22020 ggtatactac tggccttagt ttttctagtg gttaatttta tacatttaaa taggtttata    22080
ccttttaaac ttcaatggcc accttaaaa atattttgac cccacccact ataaaaaata     22140
aacatgccat cttacacgca caatctcact ttctctcccc ttacattccc taattttac     22200 tgggtatttt aatatttctt catcatcgtg gttgattaca tttacatgta tattgcagtg    22260
gtagttccca taattgttat aacctttaac catagttcta catttatttt tgccaccgtt    22320
tttcccattc accttttggt tcaactttat cttctagtag tgtcttcaaa aaagtgttct    22380
tggaaactac agcccatgaa acattattgc atatttgaaa atatttatct gtcaccatta    22440
cacctgaatg acaatttagc tagctcaaat ttactggctc acatcatctt ttttttggta    22500
attttttaag tacttctcta ctgtcatgta atgttgtatg taggatagcc taaagccaac    22560
ttgtgttttt ttattttgct gttatagtag tttgatcatt tttgcctaga tgccccatag    22620
gattattttt ctttgtcttt atttcaggaa accttactag actatggttc agtgctgact    22680
```

```
agacattttt ttccttaaga aacaccatgc cctttagatc cttagattca aatctttttt   22740
aatatcagta aagtttttaa atttacatat ttggatattt tatacttctc tagttttcc    22800 tcttaaagaa gaaaacatta attctgtctt tgcctgtctt ccatatctac aatttcttc    22860 taatcacttt ttataatttc catttcattt tgctcaattg cctcaaagct gctatctatt   22920
tttctgttgt caacaatctg tactcttaca tcagctacta tgataatatt gtgtcaccat   22980
ttactactat ttacaagcta accataattt ctctgatgat tttagttttc tcttctactt   23040
tgtgtcctag atacaggcag ctcaatttta attttgttg cttttcttga ttccttatac    23100
ctctgcatta agctcttaat tcacaaatta cttccattgt taagttattg agttcttaaa   23160
caaatatttg gtcatgattt tcatctactc cacatcaaaa tgttcatact gtgtaggctg   23220 tttgccttt ttgtcctgct attttccacc attttgtgac attttgtat ggatctcctt     23280 gttcgtttt tattattagt catccttgag tgagcagaaa tcttcctaga gcaggtattt    23340
gaaagaagta gtgtggaaga ggggctgggg ctgtgttctg cgttagtaga aaatcccta    23400 attcttagaa aaatccttta tgattcatgg tcttgtggga aaggttgtg aagcgggttt    23460 tgtgaatgtg cttcatgtgc aatagagagt gactgagagg tggtttaacc tttcttctta   23520
gctcacaaag aatggctgct acagagctgc ttaacaccca cagttttct tctacatgct    23580 gcacatttac aaagatggag tatccgtgag ttttctcact cattcctacc tcccctgcca   23640
ttttaaagta tccaaggaag ttggggagat tccctcagct aaacagccac ccagatctta   23700
ttgttccaaa caaaaatta ttagatttgc cctctgagca ggtcacctac tttggagaat    23760
tttgtgctct gccagctctc ctcaagattt ggaaaagcag ttatttcta ttggagcccc    23820 catcactcca gtccaaagtt cactgcatgt gacatcccat cttatttgtc tggttcctga   23880
ttataggagt ttcccagttt caacaaaaat actgtctttg tttttgttc tcattcattt    23940 ttccccaatt ttgtttcaaa gcgaaaagta aaaacattct tactctaaca tcttaaaatt   24000
aatgtctggg aggaacctaa actgctcatt aatatatgcc atgctatatg tgatatggca   24060
gagactgcta cctgtccacc agaatctatt tattttcttt ggatgcacaa taagactaca   24120
tttcctagtc tcccttgcaa ttacatgtga ccatgtcatt aagatttagt ggatgaaatt   24180
taagcagaag caaggtgtgt aaattctagg gctggcccat tacaaacttt aacatgggca   24240
cctgtgtgtt tttccttttc tgcttaattg ggttggagat aatcacagtg atgctgaaag   24300
ccatgtgcta aagaaggcag agcctccttc tgcttgggct cctgaatgac tgtgtggaac   24360
agaggccctt gccactcttg ggccattctg gattattaca tgcacaaaga gtaaagttct   24420
tttctgttaa gccattagat gtatgggttt atttgctgtt acagcctagt cgaacccaaa   24480
tgatgtagtg agggaggcag gacaaggaag aaacctattc agtatggagt tatccttagg   24540
gacaagttac aaaaattata aggatcagac accactgctg gttgatccat tatagaccag   24600
aataagcagg tggtatgatt ccagaaggag atgccatggt tgtgtgagag agagattaac   24660
cattcctata aacagaaggg tcaaagaaag tagccagtca ccagaatgct tatattaagg   24720
aggattgtga ctacctgtat ataaagtata ggaagaaaat ggggcagggc aattaagatg   24780
aattgcagac acaactattt gtgcatatta atttgaattt aaatttaaac ttaatttaag   24840
gataatttaa aggaaaatct tcccttacct atttcatgct gaagggtct ttcaagttgt    24900 caaactctct ctatataaat aagactgcat aatccagacc ctccggaatc cagagatgaa   24960
ttgcatgtgg tagctgatgt gtgggaagcc cacagagcag cacttctggt cattgccatc   25020
cagctagctg gtgctctcag aagaatgaga tgaagaggca tgactttcaa gcttcctctg   25080
```

```
ccatacaagg tgagtttggg ttccaggctt cttcctagcc cctgtttctg cttcctctga    25140
tttaataccc agtcactgag tacctactaa acactcggca ttaaactgaa agaacaggg    25200 aagtcaaaaa ccttttacca atgcctgatg ggataaagac atgacccatc cctcaaagag    25260
cttgtggtct tcccatggca atgcccttcc tccctaggcc agatggactg tgaagaacag    25320
cagtctcaag tggatttatt gggaagctca tgaagactca gctcaatggg ccatgtttgc    25380
aggggcccct tacaaggctc tgcacttgat tttgtaattt tgaattattt ttctcaaaaa    25440
ggcctcccaa attatgtaag cttcaggcct ttaaacttg gatctgttcc cttgaagcca    25500
cataatctga tcagaaataa ttttcagggc tcattgggtg ctggagaatt catgqttaga    25560 tatttaaata aaaatgcaga gaatctatag gactttccaa ctgagaccaa ggctttttt    25620 ttctggtagc ttgactgcca ggaaacagaa agcggggcat ctccacctgc tggcagaaga    25680
ccaaaactac accatattgc attgaccgca gacatcaggc tttgtttcct tttaagtgaa    25740
taggtgaaat caatcaagca aactggaatt aggaaacaga aggaccactc acaaccgtac    25800
ctccacagca aagctaacac tttcattttg aataacccct ttccagcccc tgtttacatc    25860
agtcacattt tttgcatgga cataatagtg tttcaggcag tcctgctcta cagaaggcat    25920
ttgtttcgct gaccataagc atcttatgtg cttctacatt gtctttatag ccagctgtct    25980
gaagttctac atcatccgtc agtgatgggt cctgagtaaa ctcagcagtc tcctctaagt    26040
aacttgtata tatccctttt ataaagaatg ctgcagtggc cacccttaag tatagaactt    26100
tgtctttccc aggcattact tacaggaaac tggggaccaa atgccactcc atagcatagc    26160
ttaggagaag tgagattcca aaggacagag tgggctggca catatgtagt agaagactgg    26220
acaaatgaga gtgaatgagc gagtctgttg tgagtggatg acacgcaatg caaccccaag    26280
ggccggctcc aatttgcaca gtccctaaaa catcccaggg atccagtctt atcgcagtct    26340
catcaacatt gacaataatc atttagaaa ttttcaccat gagactttg acactctgct    26400 ctgggatttt ggagttccaa ctgctttaac aatttataca gtcactcaaa tgtagaatcc    26460
agtgaattat taatgacaat tttgctccgc atattgaaag gcattctat attaatcaat    26520 tataaatcat gataaattgc tttctaaaaa ttatacactt gaaacccaga aatgttcaag    26580
cccctcacca gtttacatac atccttaacc gtgtcttgtt aactgggtga ccaggaaaca    26640
gagaaaggag gatgtactta atgaataact ggccagaagt cggaagacct agattttctt    26700
cccatccctt ccatagattt gctctgtgac cctagacaat tcatatgccc cctctgttac    26760 catacttttta agctgaaggg gttatagtgc atactttctg aggtccttct aacactggag    26820
atctatgagt tcataagatc acatagagtc ttggactttt cagagatcac taggcataag    26880
aaagccctcg aggacatcct cttcctagat caaccactcc aagctaagac cttaatgggt    26940
ctacactgtc atccatttat ataggagaga ggatggtaca agctaagtga aagtctgttg    27000
tcaactcagg aactagggta cagttccagc aatcaatctc catggagggt tagcagaggt    27060
ctggcctagc caattagggt ttggcactgc catatgctac tagaaaacac atgctttcat    27120
gccaggcaac agggtgggaa gtgcaatgcc attaaggacc ataccttagc ctacttaaac    27180
tagcctggga ttgagttact gagctcaaaa tacaattcag cacactttcc tgcccactgc    27240
aagtcaggcc agcccctgga gaactccagg gacaaggcaa gtctggagtt tgtccccaag    27300
gaactcccag tctagtggag gagatgggcc catagcagag ttacaaatgt ccaaaataag    27360
agcacaaatt cctgggttct taagagagt tcaagcacac acacacagag agagagagag    27420
agagagagag agagagaaat taatttagat aaggaaggga ggtagggaga gatggtgcca    27480
```

-continued

```
gcaatggctt cctgaggaaa tgtcacttgt gatgggtctt ttaggtgagt tggacattga    27540
gagaaagtaa tcaaaagggc acaagatagg gtagctgtca ggtaaacaaa acaaaactgt    27600
atgcacaaag gtctagaggc aagaaagcat gggtgtgctt gcatagcaat gaagaatgtg    27660
gtttggccaa agcataggat tcacagaagg acctccccag gccatcagta gtctctcctt    27720
cgcaggagtc cactgtggct ggacgaggaa cagatcaaaa caggtcttgt ttgaggcttg    27780
gcccaacaac agggccagct gttgaccagg gcttccttca cccttagctt tctctccccc    27840
tagtgtagtc agagactcca aaggcagtcc cagagtgttg tgccaaaaca aatgcacatc    27900
aggctattgt catcaggagc ccttgtcttg ttctgtttgt tttaagaaga cataagtgaa    27960
ataaccaggt ttccgaagag agggcagaat tgggtttgtc cccagggaaa atgaggtttc    28020
tccaccatgg ctgttctccc catgcagcag cggccagggg tccccagcag ctctttgctc    28080
agtgcccctg atgctaggcc tgatgcttcc tatgtggtca gctcagatgt gcaacccttc    28140
tccattttta ttatttgagc aatataatca ttattgcttt tgttacccaa aatcttataa    28200
tcacccattt aagagtaatg taggaatcat ttttctcttt tatttgatga actaatcttt    28260
ctggttggct cttgaggtgg gagggtggg caatggggac cagcctgctt catctcactc    28320
tttcctaggc ctgctcctta ggcacgtgcc ccacaaatcc cacctccgca ggttggaaaa    28380
ggggcccaca gaggatctca ggtatctgag gaagggccag aggctatttg cctgacatc    28440 ctggaacatc accagccagg agccataact cctttaggct agcctgcctg caactggatc    28500
aggtatagca aaaacgattg atctcacctt ctaattttca atgagtggga gtggctgcct    28560
tgagtgctgt gttgggaagg agtctgaggc agcatctgga ccctgtgtaa atatgcgttt    28620
cctgttattg atgaagcttt caagacaaga ttttagaaag cttttggctca agttgtaggt    28680 tgtgggagga aggaattagt aagagccatc ataaactcaa catctattgt gttccaggag    28740
ctgtgaccac tcccttcttt ttagtcggga aggtcaggat ctcactatgt cacctaggct    28800
agagtgcaat ggtgtgatta ttgctcattg tagtcttgaa tttgaattcc tgggctcaag    28860
taatcctcct gcctcagcct tctgagtagg tgggactact ggtgtgtgcc accacactcg    28920
gcttactcct ccctttgtat cctgctgcat cgttagtgca tgatacccac cacccctca    28980 gaggcccagc ctagtgctgt ctctcagaaa acacccttt gagtcaacag agacaaactt    29040 aggggtgcc tgactccaaa gtccaggcct tcctcctttg aggaacagca tggcttcccc    29100
agggaatatc attccatgga gacaaggcct gcagacagat ctcattttca tctgttcttt    29160
tactagccct tggaggattt gctccaaaaa cctgaggcac tgatgtttac tccagcttta    29220
cttcccccat acctggtgaa caactctggc ccagcttcca cacaccaagg cccatggctc    29280
taatagagcc agagaggcag tctcagctaa gaagagctgt atcctccagg gaccagcagg    29340
aacttccaga gatatcctac aagctccaac tgctgggaaa agcagactgg ggtcttcctc    29400
aggctccacc aaagatagcc aagtggcagc aatgacatga gcacctcatt cctgtcctag    29460
accctggcaa ttccatgaga gggaggctct gaattcacct ctgttcccag gatgtgtgac    29520
atcaatgcac attgtcatac cagatacacc tgccaaactt cagaacccct gggaagtgac    29580
cagaatgcca ctgaattcaa caccttagac caatgaacat gacctgggtc ctgtaggata    29640
ggaggcagca gcagtgtata cccagacctg gtcgactcga atagatctgc taggcgccaa    29700
gcttgtcagc cttaccagta aaaagaaaa cctattaaaa aaacaccact cgacacggca    29760
ccagctcaat cagtcacagt gtaaaaaagg gccaagtgca gagcgagtat atataggact    29820
aaaaaatgac gtaacggtta aagtccacaa aaaacaccca gaaaaccgca cgcgaaccta    29880
```

```
cgcccagaaa cgaaagccaa aaaacccaca acttcctcaa atcgtcactt ccgttttccc    29940
acgttacgta acttcccatt ttaagaaaac tacaattccc aacacataca agttactccg    30000
ccctaaaacc tacgtcaccc gccccgttcc cacgcccgc gccacgtcac aaactccacc     30060
ccctcattat catattggct tcaatccaaa ataaggtata ttattgatga tgttt         30115
```

HELPER DEPENDENT VECTOR SYSTEM FOR GENE THERAPY

FIELD OF THE INVENTION

This invention relates to adenoviral vectors which are useful for nucleic acid delivery into a cell such as in gene delivery and nucleotide vaccine applications. It also relates to host cells and methods using these vectors.

BACKGROUND OF THE INVENTION

The references cited herein are not admitted to be prior art to the claimed invention.

Adenoviral vectors provide a vehicle for introducing nucleic acids into a cell in vitro and in vivo. Over 100 different serotypes, of which 47 are of human origin, have been reported. (Hierholzer, et al., *J. infect. Dis.* 159:804–813, 1988.) Adenoviruses type 2 and 5 used to produce adenoviral vectors are well characterized.

A human adenovirus contains a 5' inverted terminal repeat (ITR); a packaging signal; region E1 made up of the early regions E1A and E1B; region E2; region E3, region E4; the late regions L1–L5; and a 3' ITR. Regions E1 and E4 contain regulatory proteins, region E2 encodes proteins required for replication, and the L region encodes for the structural proteins of the virus. The E3 region is dispensable for virus growth in vitro. (Hitt, et al., *Advances in Pharmacology* 40:137–206, 1996.)

A replicating viral vector based on the adenovirus must contain adenovirus cis elements needed for replication. Packaging also requires cis elements on the vector whereas the necessary proteins can be supplied in trans. In trans supplementation can be brought about by specialized cells and/or additional viruses producing the needed proteins. (Hitt, et al., *Advances in Pharmacology* 40:137–206, 1996.)

Different types of adenoviral vectors have been developed including those lacking one or more components of the adenoviral genome. An adenoviral vector produced without components of the adenoviral genome provides advantages such as in increasing the amount of foreign nucleic acid that can be included with the adenoviral vector and removing adenoviral genes whose expression can have detrimental effects. (Hitt, et al., *Advances in Pharmacology* 40:137–206, 1996.)

Adenoviral vectors lacking all viral protein-coding sequences have been developed. These vectors require supplementation of viral regulatory and structural proteins supplied in trans for packaging and rescue. A second adenovirus carrying genes necessary for virus growth can be used to provide in trans the required supplementation of proteins. (Mitani, et al., *Proc. Natl. Acad. Sci. USA* 92:3854–3858, 1995; Fisher, et al., *Virology* 217:11–22, 1996; Kochanek, et al., *Proc. Natl. Acad. Sci. USA* 93:5731–5736, 1996; Parks, et al., *Proc. Natl. Acad. Sci. USA* 93:13565–13570, 1996; Parks, et al., *J. Virology* 71(4):3293–3298, 1997; and Schiedner, et al., *Nature Genetics* 18:180–183, 1998.)

SUMMARY OF THE INVENTION

The present invention features helper-dependent adenoviral vector elements, and helper adenoviral elements, that enhance the production and isolation of helper-dependent adenoviral vectors. Such elements include a modified packaging signal having low homology to, and preferably less activity than, a wild-type packaging signal, an E4 non-coding segment directly joined to the 5' ITR that confers a selective advantage, and stuffer region(s) that provide a helper-dependent adenoviral vector with a GC content of about 50% to about 60%. The modified packaging signal is preferably used in a helper virus to decrease recombination and generation of the virus. The E4 non-coding segment and the stuffer region(s) are preferably used in a helper-dependent adenoviral vector to provide the vector with a growth advantage over a helper virus.

A "helper-dependent adenoviral vector" refers to a viral vector containing the cis elements needed for adenovirus replication and packaging (also referred to herein as viral generation), but lacking the necessary trans elements for adenovirus replication and packaging. The cis elements needed for viral generation is an adenovirus 3' ITR, a packaging signal, and an adenovirus 5' IRT. Trans elements needed for viral generation are the proteins encoded by the E1, E2, and E4 and L adenovirus regions. Preferably, the helper-dependent adenoviral vector lacks nucleic acid encoding for any adenovirus proteins. A helper-dependent adenoviral vector is particularly useful as a vector for delivering genes into cells in vivo.

A "helper virus" refers to a virus expressing one or more proteins needed for viral generation of a helper-dependent adenovirus. Preferably, the helper virus contains the adenovirus 3' IRT, an adenovirus packaging signal, an adenovirus 5' IRT, and encodes for the proteins of the Adenovirus E2 and E4 and L regions. Trans elements not provided for by a helper virus may be provided for by other means such as by a cell. For example, a 293 cell can be employed to supply in trans needed E1 proteins in conjunction with a helper virus not expressing such proteins.

Helper-dependent adenoviral vectors can be produced by co-cultivating with helper viruses in cell lines, wherein the helper virus alone or in combination with the cell line provide the trans functions needed for adenovirus generation. During co-cultivation of a helper-dependent adenoviral vector and a helper virus the two compete for packaging, producing a mixed viral population.

Often, during co-cultivation the helper virus has a selection advantage, such that the mixed population of helper virus and helper-dependent adenoviral vector becomes predominantly helper virus, rather than the desired helper-dependent adenoviral vector. Even when this phenomenon does not occur, the presence of lesser, but significant, amounts of helper viruses still contaminates the helper-dependent adenoviral vector preparation. Therefore, the viral populations may have to be separated physically and/or production of helper particles suppressed for the helper-dependent adenoviral vector to be used. Preferably, the percentage of helper virus in a purified helper-dependent adenoviral vector stock is below about 0.5%.

Thus, a first aspect of the present invention describes a nucleic acid molecule comprising an excisable low homology packaging signal cassette. The packaging cassette comprises a low homology packaging signal cassette flanked by a recombinase recognition sequence. The modified packaging signal has low homology to a wild-type adenovirus packaging signal.

"Flanked by a recombinase recognition sequence" indicates the presence of a recombinase recognition sequence 3' and 5' of the packaging signal allowing for excision of the flanked nucleic acid containing the packaging signal by a recombinase recognizing the recognition sequence. The recombinase recognition sequence does not need to be immediately 3' or 5' of the modified packaging signal. Preferably, the 3' and 5' recognition sequence are about 200 bp to about 2,000 bp apart.

The modified packaging signal has low homology to a wild-type adenovirus packaging signal and still allows for packaging of the helper virus during its separate production. Preferably, the modified packaging signal is less efficient than a wild-type adenovirus packaging signal.

"Low homology" refers to a maximum of about 25 bp of contiguous sequence homology (100% sequence identity) between the modified packaging signal and a wild type packaging signal present in an adenovirus, preferably human adenovirus serotype 5. Low homology is determined by aligning the modified packaging signal with wild type packaging signal to obtain a stretch of maximum contiguous homology with sequences present in both the modified and wild type packaging signals. Preferably, contiguous sequence homology is at most 23 bp.

"Less efficient" than a wild-type adenovirus packaging signal indicates that the helper virus has a lower level of packaging when it contains the modified packaging signal than it has when it contains a wild-type packaging signal present in an adenovirus, preferably from a human adenovirus group C serotype, more preferably serotype 5. Preferably, the helper virus can still be produced at yields of at least 300 PFU/cell in cells lacking a compatible recombinase. Efficiency is preferably determined using titration by end point dilution assay described in the Examples below.

Reference to "modified" is not a limitation as to how the packaging signal sequence is produced. Instead, "modified" indicates that the sequence is not a wild-type sequence.

Another aspect of the present invention describes an adenoviral helper virus for production of helper-dependent vectors comprising:

(a) an adenovirus genome having an E1 region deletion;
(b) an excisable packaging signal cassette replacing a wild-type packaging signal, the excisable packaging signal cassette comprising a 5' loxP site, a modified packaging signal and a 3' loxP site, wherein the modified packaging signal has low homology to and is less efficient than the wild-type packaging signal; and
(c) an optional insertion element comprising at least about 2900 base pairs of non-adenoviral DNA inserted in the E3 region without deleting any part of the E3 region.

Another aspect of the present invention describes a helper-dependent adenovirus vector comprising the following elements (in 5' to 3' order): (a) a 5'-inverted terminal repeat sequence; (b) a packaging signal; (c) one or more heterologous gene expression cassettes; (d) an optionally present E4 non-coding segment conferring a selective advantage; and (e) a 3' ITR; wherein (d) and (e) are located in the distal 400 bp of the adenovirus genome, and wherein the only adenoviral sequences present in the vector are said 5'-inverted terminal repeat, said 3'-inverted terminal repeat, said packaging signal, and said nonexpressed segment of the E4 region.

The "E4 non-coding segment" refers to the nonexpressed segment of the E4 region co-localized with the E4 promoter. The segment is adjacent to the 3' ITR and, in human adenovirus serotype 5, is about 300 bp in length.

Another aspect of the present invention describes a helper-dependent adenovirus vector having a GC content between about 50% and about 60%. The vector comprises in a 5' to 3' direction: (a) a 5' ITR; (b) a packaging signal cassette directly joined to the 3' of the 5' ITR; (c) a first stuffer DNA at least about 1 kb; (d) at least one heterologous expression cassette; (e) a second stuffer DNA at least about 1 kb; (f) an optionally present non-coding E4 segment; and (g) a 3' ITR. Element (f) if present is directly joined to element (g). The virus does not encode one or more adenovirus proteins needed for adenovirus generation and is about 28 kb to about 36 kb. Preferably, the virus does not encode any adenovirus proteins.

"Directly joined" indicates the absence of significant intervening sequences (e.g., less than about 150 bp) that interfere with the function of "joined" groups.

"Stuffer sequences" refer to nucleic acid regions that do not express protein when present in a helper-dependent adenoviral vector. Preferably, such regions are mammalian non-gene regions or introns.

Another aspect of the present invention describes a cell line infected with a helper virus, a helper-dependent viral vector, or both the virus and the vector. Preferably, the cell line expresses E1 proteins and a recombinase, and is infected with a helper virus that (1) contains an excisable low homology signal packaging cassette, and (2) does not express E1 proteins needed for viral generation.

Another aspect of this invention is a method of generating helper-dependent adenoviral gene vectors in a cell line expressing E1 proteins and Cre recombinase comprising:

a) infecting the cell line with a helper-dependent vector comprising: a 5'ITR, a packaging signal, at least one heterologous expression cassette, human genomic stuffer DNA and a 3' ITR, wherein the overall size of the helper-dependent vector is between about 28 kb and 36 kb, and wherein no functional adenoviral coding sequences and no bacterial origin of replication or bacterial marker genes are present;

b) infecting the cell line with a helper virus comprising: an adenovirus genome having an E1 region deletion; an excisable packaging signal cassette replacing a wild-type packaging signal, the excisable packaging signal cassette comprising a 5'loxP site, a modified packaging signal and a 3'loxP site, wherein the modified packaging signal has low homology to and is less efficient than the wild-type packaging signal; and an optional insertion element comprising at least about 2900 base pairs of non-adenoviral DNA inserted in the E3 region without deleting any part of the E3 region; and c) obtaining the generated helper-dependent viral vectors.

Another aspect of the present invention describes a method of generating helper-dependent adenoviral vectors. The method involves producing a cell comprising: (i) trans functions needed for adenovirus generation and (ii) a helper-dependent adenoviral vector comprising the necessary cis functions needed for adenovirus generation and at least one heterologous expression cassette, wherein the helper-dependent adenoviral vector does not encode for any adenovirus proteins, is about 28 kb to about 36 kb, and has a GC content between about 50% and about 60%. The cell is used to generate the helper-dependent vector.

Reference to a cell comprising the trans functions needed for adenovirus generation indicates such functions are present in the cell, but need not be part of the cellular genome. The trans functions can be provided, for example, by a helper virus, the cellular genome, or a combination of both. Another example of a source of trans functions is a plasmid.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

DETAILED DESCRIPTION OF THE INVENTION

Figure 1:
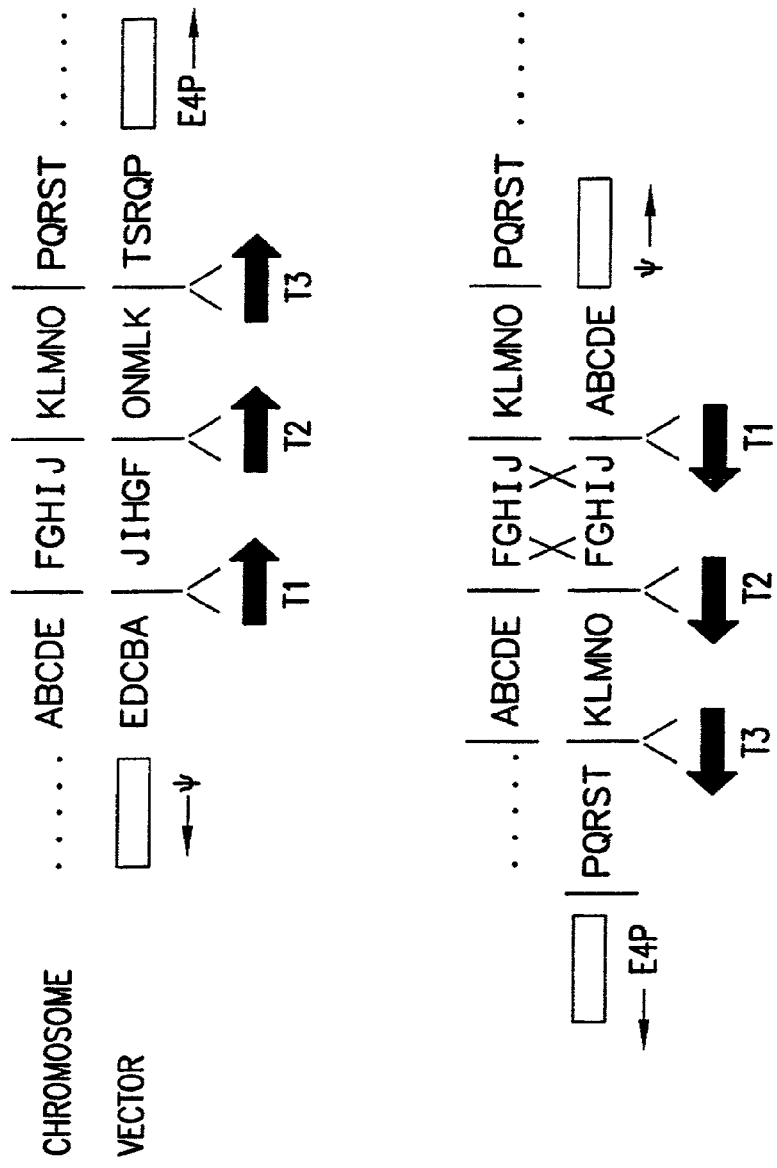
FIG. 1 shows the shuffling of fragments of a stuffer to prevent genomic integration of the expression units.

The present invention is particularly useful for obtaining and isolating helper-dependent adenoviral vectors produced using a helper virus. Co-cultivation of a helper-dependent adenoviral vector and a helper virus produces two different particles competing for packaging and results in a mixed viral population. The production of the helper virus in the mixed viral population reduces the amount of helper-dependent adenoviral vector produced, provides a viral contaminant that interferes with applications of the helper-dependent adenoviral vector, and produces a source of nucleic acid that can be recombined with helper-dependent adenoviral vectors As described herein, production and isolation of helper-dependent adenoviral vectors can be facilitated in different ways. One way is to employ helper-dependent adenoviral vectors containing elements favoring viral generation of the helper-dependent adenoviral vector over a co-cultured helper virus. Another way is to employ helper viruses containing elements that can be employed to reduce the ability of the helper virus to grow, and/or recombine with the helper-dependent adenoviral vector.

The term "vector" employed herein is used in its broadest sense, and is meant to encompass a linear virus which can carry a heterologous gene, and or a plasmid which can contain one or more regions of a virus genome. The term encompasses a helper-dependent adenoviral vector and a helper virus.

Adenovirus components present in a helper or a helper-dependent vector may in general be provided from any adenovirus. Preferably, a human adenovirus serotype is used; more preferably, human adenovirus serotype 1-47; and more preferably, a group C serotype (e.g., serotypes 1, 2, 5, and 6). Preferred group C serotypes are human adenovirus serotype 2 or 5, and more preferably serotype 5.

A helper-dependent adenoviral vector preferably contains a heterologous expression cassette. Such a cassette is made up of a heterologous gene functional coupled to a promoter and regulator elements needed for gene expression, and is particularly useful for introducing nucleic acid into a cell. The introduced nucleic acid preferably encodes for a gene or is able to regulate gene expression. Nucleic acid able to regulate gene expression include ribozymes and antisense nucleic acids.

The ability to introduce nucleic acid into a cell using the present invention has different applications such as in gene therapy, in antibody production (e.g., a vaccine) and research to examine the regulation of a gene in vivo or in vitro. Different genes can be introduced into a cell such as Factor VIII, Factor VIX, CFTR, OTC, LDL, VEGF, FGF, EPO, HSV-TK, IL-2, IL-12, p53, HLA-B7, α-interferon, and cytosine deaminase.

A promoter is a DNA sequence directing the synthesis of RNA through an RNA polymerase. Suitable promoters depend upon the gene and intended use, and may include promoters such as EF1α, CMV, chicken α-actin (Arnold, et al., *Nucleic Acids Res* 1988 Mar. 25; 16(6):2411–29), and muscle creatine kinase (Johnson, et al., *Mol Cell Biol* 1989 August; 9(8):3393–9).

Generally, the regulatory elements that are present include a ribosome binding site, a terminator, and an optionally present operator. Another preferred element is a polyadenylation signal. Regulatory systems are available to control gene expression, such as GENE-SWITCH™ (Wang, et al., *Gene Ther.* 1997 May;4(5):432–41, U.S. Pat. No. 5,874,534 and International Publication WO 93/23431, each of which are hereby incorporated by reference herein) and those involving the tetracycline operator (U.S. Pat. Nos. 5,464,758 and 5,650,298, both of which are hereby incorporated by reference herein).

A helper-dependent adenoviral vector is preferably from about 28 kb to about 36 kb to provide for efficient packaging. An adenovirus can accommodate up to about 105% of the wild-type genome and has a lower packaging limit of about 75% of the wild-type genome. (See, Parks, et al., *J. Virology* 71(4):3293–3298, 1997, hereby incorporated by reference herein.) In a preferred embodiment, there are no bacterial plasmid-based sequences (such as an origin of replication or bacterial marker genes) present in the helper-dependent adenoviral vector.

Construction of helper viruses and helper-dependent viruses can be achieved based on the guidance provided herein using techniques well known in the art, such as those described by Ausubel, *Current Protocols in Molecular Biology*, John Wiley, 1987–1998, and Sambrook, et al., in *Molecular Cloning, A laboratory Manual*, $2^{nd}$ Edition, Cold Spring Harbor Laboratory Press, 1989, both of which are hereby incorporated by reference herein. Additional descriptions of useful techniques are provided, for example, in the Example section provided below and references such as Mitani, et al., *Proc. Natl. Acad. Sci. USA* 92:3854–3858, 1995; Fisher, et al., *Virology* 217:11–22, 1996; Kochanek, et al., *Proc. Natl. Acad. Sci. USA* 93: 5731–5736, 1996; Parks, et al., *Proc. Natl. Acad. Sci. USA* 93:13565–13570, 1996; Parks, et al., *J. Virology* 71(4):3293–3298, 1997; and Schiedner, et al., *Nature Genetics* 18:180–183, 1998; each of which are hereby incorporated by reference herein.

The helper-dependent adenoviral vector and the helper virus can be generated in a wide range of host cells able to be infected by adenovirus. Examples of host cells include 293 cells, 911 cells and PERC.6 cells (WO 97/00326 hereby incorporated by reference herein). The employed cell can be constructed to provide for useful proteins such as viral proteins or a recombinase.

Helper Virus

Helper virus elements useful for facilitating the production and isolation of helper-dependent viruses include a low homology excisable packaging signal cassette and a substituted E3 region. Preferred helper viruses contain both a low homology excisable packaging signal and a substituted E3 gene.

Low Homology Excisable Packaging Signal Cassette

The low homology excisable packaging signal cassette contains a modified packaging sequence which fulfills the role of an adenovirus packaging signal, has a low homology to the Adenovirus packaging signal, and is flanked by a 3' and 5' recombinase recognition sequence. Preferably, the modified packaging signal is less efficient than a wild type packaging signal. Advantages of such low homology excisable packaging signals include: (1) less recombination between the helper virus and helper-dependent adenoviral vector; and (2) when a less efficient packaging signal is used, less packaging of those helper viruses which escaped excision of the packaging signal.

Recombinase recognition sequences recombine when acted on by a recombinase that recognizes the sequences, resulting in the excision and circularisation of intervening nucleic acid. The recognition sequences should be sufficiently far apart, at least about 180 bp, to allow for the proper positioning of nucleic acid segments being recombined. Preferably, the recombinase recognition sequence is loxP or frt.

The loxP recognition sites can be positioned 3' and 5' of the packaging signal to allow for excision by Cre recombinase. Cells, such as 293 cre cells, stably expressing Cre recombinase can efficiently remove nucleic acid located between loxP recognition sites. (See, Parks, et al., *Proc. Natl. Acad. Sci.* 93:13565–13570, 1996 and Parks, et al., *J. Virology* 71(4):3293–3298, 1997, both hereby incorporated by reference herein).

The frt recognition sites can be positioned 3' and 5' of the packaging signal to allow for excision by Flp recombinase. Cells stably expressing Flp recombinase can efficiently remove nucleic acid located between frt recognition sites. Flp-mediated gene modifications are described in U.S. Pat. No. 5,564,182, hereby incorporated by reference herein.

Homology between a helper and the helper-dependent adenoviral vector encourages recombination events between the two, resulting in unwanted changes in the structure of the helper-dependent adenoviral vector or the helper virus, and leading to an increased contamination by helper virus. For example, if the first of a loxP site flanking the packaging signal is removed by homologous recombination within the packaging signal, the resulting helper virus escapes selection in 293cre cells because the Cre recombinase is no longer able to excise the packaging signal.

Sequences for different low homology excisable packaging signal cassettes can readily be designed taking into account recombinase recognition sequences and adenovirus wild-type packaging signal sequences using the guidance provided herein. The provided guidance focuses on the adenovirus serotype 5 packaging signal to illustrate the production of a modified packaging signal. Such guidance is applicable to producing other modified packaging signals taking into account other adenovirus serotypes.

The wild-type packaging signal of adenovirus serotype 5 is formed by at least seven functional units called A repeats, which are located between nt 230 and nt 380 of the genome. The A elements have the consensus sequence ATTTGN$_8$CG (Schmid et al, 1977 *J. Virol.* 71:3375–3384, which is hereby incorporated by reference). The modified packaging signal of this invention preferably comprises less packaging elements than the wild-type (which has seven elements), preferably from about two to six elements, and more preferably from three to five elements. In a preferred embodiment, the modified packaging signal contains only four out of the seven original packaging elements (elements AI to AIV). The four elements are preferably in a modified form with two strong elements (AI and AII) present. The position of the elements relative to each other may be changed, but in preferred embodiments, it is maintained.

In order to reduce the contiguous sequence homology, the eight ambiguous nucleotides of the consensus sequence (ATTTGN$_8$CG; SEQ ID NO:1) within each A element are preferably replaced by sequences taken from a different A element. For example, the eight nucleotides within A1 were replaced by those from AV; and the eight nucleotides within AII were replaced by those from AVI. In addition, a new element was created between AII and AIII starting 21 bp after AII, by changing the existing nucleotides to the consensus sequence. Two more nucleotides were exchanged within AIV: ATTTTGTGTT (SEQ ID NO:2) was changed to ATTTTGTTGT (SEQ ID NO:3). One embodiment of a synthetic packaging signal is given in SEQ ID NO:4.

Desired nucleic acid sequences can be produced using different techniques including those involving the creation of nucleic acid mutations and nucleic acid synthesis techniques. Examples of such techniques are provided in Ausubel, *Current Protocols in Molecular Biology*, John Wiley, 1987–1998, and Sambrook, et al., in *Molecular Cloning, A laboratory Manual*, 2$^{nd}$ Edition, Cold Spring Harbor Laboratory Press, 1989, both of which are hereby incorporated by reference herein.

E3 Insertion

Homologous recombination between viral sequences (E1) present in the cell lines used for propagation of either helper virus (lacking E1) or helper-dependent adenoviral vector, and the helper virus itself, has resulted in the generation of wild-type viruses. Homologous recombination results in the insertion of the E1 region into an E1-deleted virus genome. To avoid this problem, in preferred embodiments of this inventions, the helper virus also contains an insertion element. Preferably, the insertion element does not contain a promoter or encode for a protein when present in the helper virus. More preferably, the insertion element is non-coding repeat-free human DNA devoid of splice signals.

Parks, et al., *Proc. Natl. Acad. Sci. USA* 93:13565–13570, 1996, describe the use of an E3 region containing an insert encoding for the ampicillin gene, the bacterial origin of replication, a CMV promoter and the luciferase gene (AdLC8BHG10luc). The insert protected against the production of viable viruses having a wild type E1 produced by homologous recombination. However, the insert impairs virus generation, most likely by interference with fiber gene expression. The resulting level of viral generation is disfavored for the production of viral stock.

The use of non-coding sequences as an E3 insertion element, preferably human non-gene sequences, provides for more efficient viral generation than that observed with E3 insertional elements encoding for bacterial protein described by Parks, et al., *Proc. Natl. Acad. Sci. USA* 93:13565–13570, 1996 (see Table 1, infra.) The use of intron sequences are preferred because such sequences do not contain hidden splice signals that could interfere with correct splicing of the fiber message.

The size of the insertion element (preferably between about 2800 and 3500 bp, more preferably about 2900 bp) is chosen to avoid the generation of potentially harmful wild-type viruses while maintaining a virus size close to wild-type size. Starting with a helper virus having a deleted E1, if homologous recombination occurs resulting in insertion of the E1 region, the recombined adenoviral vector which also contains the E3 insertion element would have a genome size of approximately 38350 bp (108.1% of wild-type size). Because this size exceeds the packaging limit of Adenovirus 5, no viable virus would be produced.

The insertion element may be from virtually any source. In a preferred embodiment, a 2900 bp insert was taken from human chromosome 11q13, starting 13340 bp upstream of STS marker 11S1337 (available from Genethon) and inserted into the Xba I site at position (nt) 28593 (referring to Ad5 wild-type).

The insertion element and its insertion point in E3 should be chosen to avoid any reduction in synthesis of the fiber protein. Such a reduction is likely to occur if the E3 region is modified because synthesis of fiber protein is dependent on correct splicing of RNA from signals located in this region. We demonstrate that viruses containing the insert grow to titers similar to those obtained with viruses containing an unchanged E3 region.

Helper-Dependent Adenoviral Vector

Helper-dependent adenoviral vector elements useful for facilitating the production and stability of helper-dependent adenoviral vectors include an E4 non-coding segment that confers a selective advantage to a virus and stuffer region(s) that provide a helper-dependent adenoviral vector with a GC content of about 50% to about 60%. Preferably, the helper-dependent adenoviral vector contains an E4 non-coding segment conferring a selective advantage to the vector; and stuffer region(s) providing the vector with a GC content of about 50% to about 60% and an overall size of about 28 kb to about 36 kb. In a preferred embodiment, there are no bacterial plasmid-based sequences (such as an origin of replication or bacterial marker genes) present in the helper-dependent adenoviral vector.

Stuffer DNA

Stuffer sequences are used to provide a helper-dependent adenoviral vector with an overall size of about 28 kb to about 36 kb. A helper-dependent adenoviral vector containing only a heterologous expression cassette, adenoviral ITR's and a packaging signal may be quite small, in general about 5–10 kb, depending on the size of the heterologous expression cassette. Because such a small virus does not package efficiently stuffer sequences are added to provide a final size of about 28 kb to about 36 kb. Preferably, the stuffer provides the vector with a GC content of about 50% to about 60%.

Stuffer sequences used in gene therapy applications should not contain active genes or be recognized as foreign in a human cell. A preferred stuffer sequence replicates as well as the adenovirus itself, is not recognized by the host as foreign DNA and does not lead to chromosomal integration of the transgene.

Genomic DNA of mammalian origin, or even more preferably of human origin, are preferred stuffer sequences for gene therapy applications to avoid eliciting an immune response. However, stuffer based on human genomic DNA is identical to chromosomal sequences in a human target cell and could allow for insertion of the heterologous expression cassette into the host genome by homologous recombination. This phenomenon could have a potentially dangerous effect and should be prevented.

To prevent integration of the heterologous expression cassette into the host genome, the contiguous stuffer sequence can be interrupted, the individual fragments reversed and the expression units inserted at the specific breakpoints. (See for example, FIG. 1.) Using this strategy, the transgene is not flanked by regions which would support homologous recombination. Additionally, potentially unstable genetic elements such as retrovirus LTR as well as genomic repeats (e.g., MIR, and ALU) should avoided or removed to prevent rearrangements during amplification.

Another consideration is the GC content of the virus. The GC content that stuffer sequences provide to a helper-dependent adenoviral vector has a major impact on yield and purity of the virus. Competition experiments between different viruses as well as individual analysis revealed a correlation between the GC content of a virus and growth properties. The GC content is preferably between about 50% and about 60% and even more preferably between 52% and 57% which is close to the GC of wild-type adenovirus. Without being limited to any particular theory, advantageous growth properties are believed to be based on more efficient generation of a virus with a higher GC content.

Preferably, stuffer sequences are provided such that the heterologous gene cassette(s) that are present are at least about 1.0 kb from the helper-dependent viral vector 3' end and 5' end, more preferably at least about 2.0 kb, and more preferably at least about 4.0 kb. Additionally, high AT rich segments such as those provided in the hprt fragment (59% AT) may be unfavorable even with a viral vector having an overall high GC content. A "high" AT is above about 55% AT.

E4 Non-Coding Segment

The E4 region of adenovirus type 5 occupies about 3000 bp at the right end of the genome. Transcription from the E4 promoter is directed from the right end toward the center. Seven polypeptides are produced from open reading frames (ORFs) located within the region with the first ORF starting at nucleotide (nt) 406 from the right end of the virus.

It was observed that the E4 region is sometimes transferred from a helper to a helper-dependent adenoviral vector as a result of homologous recombination. This recombined helper-dependent adenoviral vector generally is favored in co-cultivation with the non-recombined helper-dependent adenoviral vector and dominates in vector preparations. Despite its strength, this recombined helper-dependent adenoviral vector cannot be used as a helper-dependent vector for gene therapy because it contains functional E4 genes. Expression of those E4 genes in a host cause an immune rejection of vector infected cells by the host.

In accordance with this invention, it has been determined that a noncoding segment of the E4 region confers a selective advantage when a virus is co-cultivated with a virus lacking the same element. The entire E4 region is not needed.

From adenovirus serotype 5, the part of E4 between the 3' ITR (starting 102 nt from the right end) and nt 405 which does not contain coding sequence is the segment that should be preferably included into the helper-dependent vector and is a non-coding E4 segment. E4 sequences located left of this element have no additional impact on virus strength. This is of importance because all genes (open reading frames, orfs) are located in the left part of the E4 region. Thus, another aspect of this invention is a cis-acting sequence located next to the 3' ITR (right virus end) which is preferably incorporated into the helper-dependent adenoviral vector because it supports amplification of the helper-dependent adenoviral vector.

Competition experiments were designed to determine the location of the beneficial element. Helper-dependent adenoviral vectors based on the vector stk120 (which contains only a 5'ITR, a 3' ITR and packaging signal as its viral-based nucleotides, as described in Morsy et al., 1998, *Proc. Natl. Acad. Sci. USA* 95:7866–7871, which is hereby incorporated by reference) were constructed containing either the 3'ITR only (stk120gfp), the 3'ITR and noncoding sequence of the E4 region until nt 400 from the right end (stk120gfp-E4promoter) or the 3' ITR and the complete E4 region to nt 3115 from the right end (stk120gfp-E4). Pairs of these vectors were cotransfected at a 1:1 ratio to originate rescues of two competing helper-dependent adenoviral vectors.

After passage seven, viruses from at least three independent rescue procedures were purified, and DNA was extracted and analyzed by radioactively labeled restriction digests. The two competing helper-dependent adenoviral vectors have an almost identical restriction pattern. The only difference is in the size of one fragment, called the discriminating fragment. The discriminating fragment was found 5–10 fold stronger for stk120gfp-E4-promoter than for stk120gfp, and at least 4 fold stronger for stk120gfp-E4 than for stk120gfp (see FIGS. 2a and 2b). However, the discriminating fragments are of equal strength for stk120gfp-E4-promoter and stk120gfp-E4 in each rescue (see FIG. 2c). Therefore an E4 element supporting helper-dependent adenoviral vector growth is present in stk120gfp-E4 promoter and stk120gfp-E4 and must be entirely located in the right part of the E4 region (between nucleotide −400 from the right end and the 3'ITR).

While not wishing to be bound by theory, it appears that there are two possible explanations for the selective advantage to the E4 segment-containing adenoviral vector: the E4 element allows for more effective replication of the virus or it confers improved packaging and stability. Our results indicate that the E4 segment does not effect replication. If infection is started with equal amounts of helper and helper-dependent adenoviral vectors, the ratio between helper and helper-dependent genomes inside the cell at the end of the production cycle (48 hours) is identical. However, 3-fold more helper-dependent adenoviral vectors were packaged for the genome containing the E4 segment compared to contaminating helper genomes. Thus, it appears that the E4 segment supports effective packaging.

EXAMPLES

Examples are provided below to further illustrate different features and advantages of the present invention. The examples also illustrate useful methodology for practicing the invention. These examples do not limit the claimed invention.

Example 1

General Materials and Methods

Construction of Plasmids

Cloning techniques described in J Sambrook, E. F. Fritsch and T. Maniatis, 1989 *Molecular Cloning*, Cold Spring Harbor Laboratory Press, which is hereby incorporated by reference, were used.

To generate plasmids containing the entire Ad5 genome, homologous recombination in *E. coli* based on the recF pathway was used. Competent cells of *E. coli* strain BJ 5183 were transformed with a plasmid vector containing the adenovirus genome and a fragment from the shuttle vector. This fragment contains the sequence to be inserted flanked on both sides by sequences homologous to the vector. In order to select against re-transformation of the vector without modification, it was linearized close to the insertion point. DNA isolated from individual colonies of BJ5183 was retransformed into the strain XL2 (Stratagene) and high yield plasmid preparations were obtained. Correct clones were determined by restriction analysis and sequencing.

Virus Rescue

10 μg helper plasmid was digested with PacI and transfected by calcium phosphate coprecipitation into a 6 cm dish of subconfluent 293 cells. Directly after transfection cells were overlaid with αMEM/10% FCS/0.8% Seaplaque agarose. 20–100 plaques appeared after 7–9 days. Plaques were taken 12 days after transfection and used to reinfect cells. After two intermediate passages the cell lysate was used to infect NUNC-cell factories (NUNC). Cells were harvested 48 hours after infection and virus was released by three freeze/thaw steps steps (−70° C./37° C.). After treatment of the cleared lysate with BENZONASE nuclease, viruses were purified by ultracentrifugation on a CsCl gradient. After one step gradient (q=1.5/1.35 1.25 g/cm$^3$) the viruses were loaded on a continuous gradient formed from a CsCl solution of q=1.35 g/cm$^3$. Viruses were dialyzed against 10 mM Tris pH 8.0, 10 mM MgCl$_2$ and 10% glycerol and stored in aliquots at −70° C. Helper-dependent adenoviral vectors were purified using substantially the same procedure. For analytical purposes virus obtained from two 15 cm dishes was purified. Virus DNA was cut with Hind III or other restriction endonucleases, restriction fragments were labeled using αP$^{33}$dATP or dCTP and Klenow polymerase and separated in 0.7% agarose gels. The gel was dried and exposed to film.

Determination of Particle Titer

10 μl of virus suspension was added to 90 μl PBS/0.1% SDS and incubated at 50° C. for 20 minutes. OD$_{260}$ is determined spectrophotometrically and the concentration of virus particles was calculated based on the equation 1 OD$^{260}$=1.1×10$^{12}$ particles.

Extraction of Viral DNA and Restriction Digest

100 μl of virus suspension were added to 100 μl lysis solution (10 mM Tris-HCl pH 7.5, 10 mM EDTA, 0.5% SDS, 0.05% pronase) under constant vortex. After an incubation at 37° C. for at least 2 hours followed by addition of 100 μl TE the lysate was extracted 1× with Tris-HCl saturated phenol. Virus DNA was precipitated with two volumes of ethanol, washed extensively with 70% ethanol and resuspended in TE. Virus DNA was cut with Hind III or other restriction endonucleases, restriction fragments were labeled using αP³³dATP or dCTP and Klenow polymerase and separated in 0.7% agarose gels. The gel was dried and exposed to film.

Extraction of Cellular DNA from Infected Cells $10^6$ cells are lysed in 10 mM Tris-HCl pH 7.5, 10 mM EDTA, 0.5% SDS and treated with 100 μg/ml Proteinase K overnight at 58° C. The lysate was extracted with Tris saturated phenol, phenol/chloroform/isoamylalcohol (24:24:1) and chloroform, precipitated with two volumes of ethanol, washed extensively with 70% ethanol and resuspended in TE.

End Point Dilution Assay 96 well plates were seeded with $1\times10^4$ 293 cells in 100 μl per well 24 hours before the assay. Each virus stock was diluted $10^3$ to $10^8$-fold. Dilutions were used to infect 24 wells each (50 μl/well). Positive wells were scored by cytopatic effect after 14 days and the virus titer was calculated based on two dilutions with intermediate numbers of positive wells taking the dilution factor into account.

Quantitative PCR

Real time quantitative PCR (ABI PRISM 7700) was used to determine the relative amounts of helper and helper-dependent adenoviral vector. Two specific target sequences were selected present either in all helper viruses (Ad5 sequences from 11358–11456) or in all helper-dependent adenoviral vectors based on stk120 (bp 12037–12176) (Morsy et al., 1998, *Proc. Natl. Acad. Sci. USA* 95:7866–7871). A plasmid containing both target sequences was constructed and used as one standard for both amplifications. Within each target sequence, a set of forward primer, reverse primer and probe (which is located between the primers and contains a fluorogenic reporter and a quencher) have been selected. Separation of quencher and reporter generated a fluorogenic signal during the logarithmic phase of PCR amplification which was plotted versus cycle number. The plot was used to calculate template concentration based on the software of the 7700 system (ABI).

Example 2

Construction of Helper Viruses

Helper viruses for the helper-dependent system were made based on Ad5. In order to obtain specific helper functions, the plasmid pAdE1–E3+ (containing the entire Ad5 genome with a complete deletion of the E1 region) was modified in two regions: i) between the left ITR and the promoter of protein IX; and ii) in the E3 region.

To introduce changes at the left end of the genome a shuttle vector "ploxΔpack" was constructed. It is based on pUC (Boehringer Mannheim) and contains the following elements:

A) nt 1-195 of Ad 5 linked to a unique Pac I site immediately before nt 1;

B) a loxP site starting directly after nt 195 of Ad5;

C) a synthetic packaging signal contained in the following sequence:

(SEQ. ID. NO: 4)
5'- GTACACAGGA AGTGACTTTT AACGCGCGGT TTGTTACGGA

TGTTGTAGTA AATTTGTCTA GGGCCGAGTA AGATTTGACC

GTTTACGCGG GGACTTTGAA TAAGAGCGAG TGAAATCTGA

ATAATTTTGT TGTACTCATA GCGCGTAATC TCTAGACG-3'.

D) a second lox P site;

E) a linker containing cloning sites; and

F) 2247 nucleotides of Ad5 sequence starting from nt 3534 (according to wild-type adenovirus numbering).

For comparison, a second shuttle vector, "ploxpack", containing the wild type packaging signal instead of the synthetic one was constructed. It contained:

A) nt 1-195 of Ad 5 linked to a unique Pac I site immediately before nt 1;

B) a loxP site starting directly after nt 195 of Ad5;

C) Elements AI-AIV of the wild-type packaging signal contained in the following sequence:

(SEQ. ID. NO. 5)
5'-GTACA CAGGAAGTGA CAATTTTCGC GCGGTTTTAG

GCGGATGTTGTAGT AAATTT GGGCGTAACC GAGTAAGATT

TGGCCATTTT CGCGGGAAAACTGAA TAAGA GGAAGTGAAA

TCTGAATAAT TTTGTGTTAC TCATAGCGCGTAATCTC TAGACG-3'

D) a second lox P site;

E) a linker containing cloning sites; and

F) 2247 nucleotides of Ad5 sequence starting from nt 3534 (according to wild-type adenovirus numbering).

The second shuttle vector was generated by cloning the 4.9 kb XhoI fragment from Ad5 wild-type (Ad5 wt) DNA (nt 24797–29791) into pUC. A 2900 bp fragment of human DNA located on chromosome 11q13 starting 13340 bp upstream of STS marker 11S1337 (Genethon) was obtained by PCR and inserted into the XbaI site at nt 28593 (Ad5 wt) in either orientation. This fragment contains part of intron 2 of the human LRP5 gene.

A strategy based on homologous recombination between plasmids in *E. coli* (Chartier, et al., 1996 *J. Virol* 70: 4805–4810, which is hereby incorporated by reference) was used to introduce those sequence elements into plasmid pAd5E1–E3+ containing a complete Ad5 genome with a deletion of E1. The procedure allowed for insertion of those elements at exactly the positions described for the shuttle vectors. The flanking Ad5 derived sequences were completely maintained. The following plasmids for new helper viruses were constructed:

pAdlspLI1=Helper 14—has synthetic packaging signal, intron of LRP5 in E3;

pAdlpLI1=Helper 1—has wild type packaging signal, intron of LRP5 in E3;

pAdlpE3=Helper 11—has wild type packaging signal, wild type E3.

Plasmids containing the Ad 5 genome with the described modifications were digested with PacI to release the virus genome from the plasmid and transfected into 293 cells by calcium phosphate coprecipitation. Resulting virus plaques were used to reinfect cells. Amplified virus stocks were characterized by restriction and sequence analysis.

1. Growth of Helper Viruses in 293 and 293cre Cells

Different helper viruses as well as a E1 deficient adenovirus (dl70-3) (Bett et al. *Proc. Natl. Acad. Sci. USA* 91:8902–8906 which is hereby incorporated by reference) taken as control, were grown in 10 layer NUNC cell factories, purified in CsCl Gradients and dialyzed. The virus concentration (particle concentration) was determined by spectro-photometric analysis ($OD_{260}$). $1.5\times10^6$ cells (293 or 293 cre) were infected in a 6 cm plate with 100 particles per cell. CPE was apparent in all plates after 48 hours. Cells and medium were harvested, frozen and thawed 3× and the titer was determined in an end point dilution assay. The number of infectious viruses produced per cell was calculated and the results are shown in Table 1.

TABLE 1

|  | d170-3 Ad without lox | AdLC8BHG10luc | AdlpLI1 Helper 1 Wt. Ψ | AdlpLI1 Helper 14 Synth. Ψ |
|---|---|---|---|---|
| 293 cells | 1200* | 27 | 840 | 610 |
| 293cre4 cells | 1400 | 1.2 | 1.3 | 0.8 |

*infectious units per cell

The amplification rate for all new helper viruses exceeds that of AdLC8BHG10luc (Parks et al., 1996, *Proc. Natl. Acad. Sci. USA* 93:13565–13570, which is hereby incorporated by reference) by at least 20 fold. The growth of the helper viruses in contrast to dl70-3 is well controlled in 293cre4 cells. These cells release only 1–2 infectious particles/cell. The rate of suppression is therefore dramatically increased for the new helper viruses. Viruses without or with the insert in E3 in either orientation do not differ much in virus yields; thus, the chosen E3 insert did not have a major impact on virus growth.

2. Amplification of Helper-Dependent Adenoviral Vectors Over a Single Passage

Figure 3:
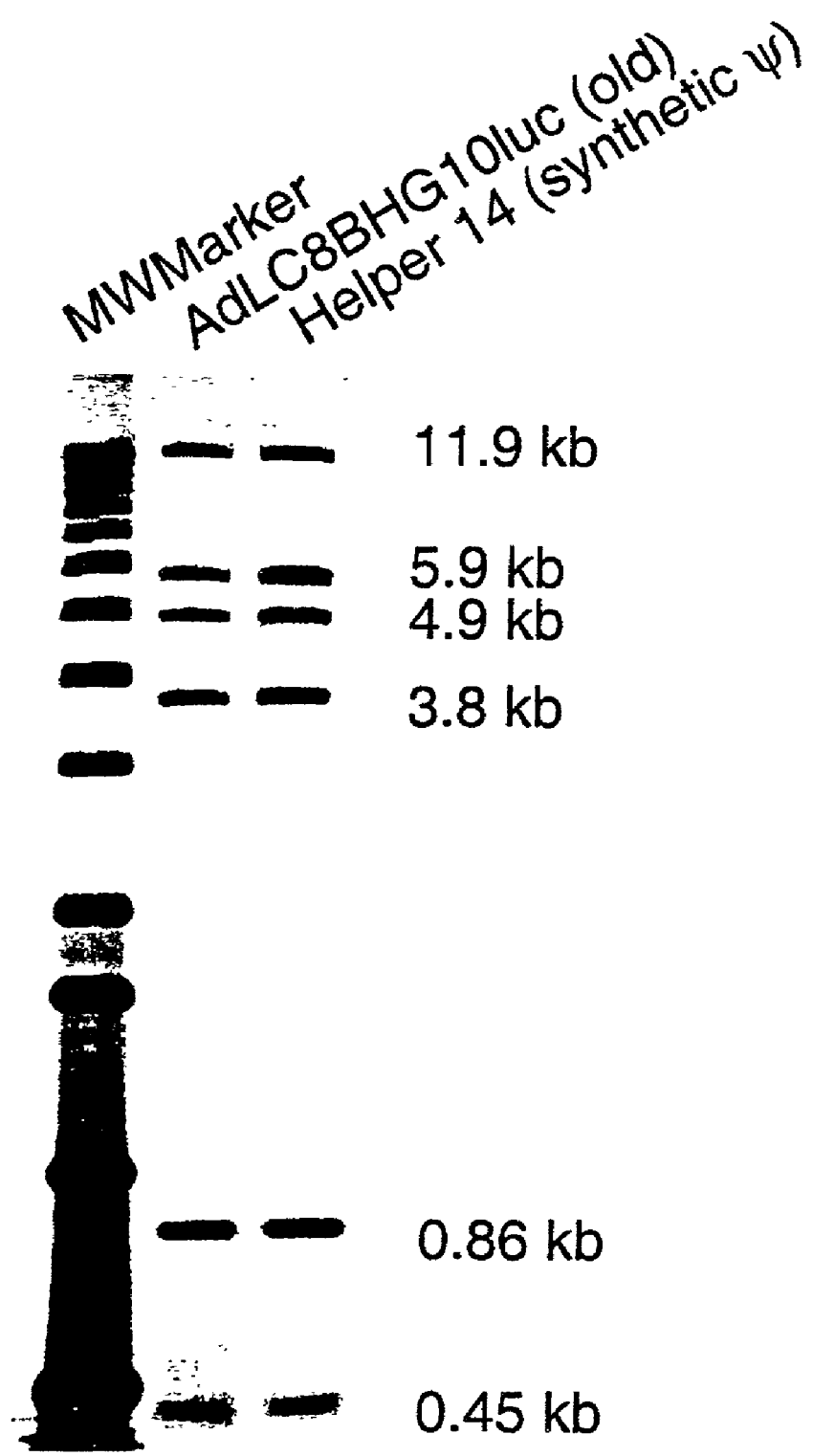
FIG. 3 is a gel showing restriction digests of helper-dependent adenoviral vectors grown with the helper AdLC8BHG and a helper of this invention.

A characterized stock (known particle titer and helper contamination) of a helper-dependent adenoviral vector containing the human OTC gene was used to infect 293cre cells. Cells were infected with 700 particles of the helper-dependent adenoviral vector and 100 particles of one of the helper viruses per cell. After 48 hours cells were collected, virus was released through 3 freeze/thaw steps and purified by Cs banding. Particle titers were determined by spectrophotometric analysis ($OD_{260}$). Virus DNA was extracted and analyzed by restriction digests (FIG. 3). Overall virus yield was slightly increased for the new helper virus over helper AdLC8BHG10luc. However, the ratio between DNA-containing particles and empty particles is increased for the new helper. Since helper DNA is undetectable in the gel, helper virus does not contribute significantly to the overall output.

To determine helper contamination more accurately, quantitative PCR based on Taqman™ technology was used. Contamination was similar between the helper AdLC8BHG10luc and the helper LPLI1 containing the original packaging signal, whereas the amplification supported by helper LSPLI1 containing the modified packaging signal resulted in a lower contamination (0.29%) (Table 2). This is expected because yields of virus grown in 293 cells are lower than those of an identical virus containing the normal packaging signal. Therefore helper virus which would escape cre-selection should still have a selective disadvantage.

TABLE 2

|  | HD Virus | Helper Contamination | | |
|---|---|---|---|---|
|  | Productivity | % cont. | St. Dev. | % RSD |
| AdLC8BHG10luc | 4800 | 0.52% | 0.1% | 22% |
| Helper 1 (Wt. Ψ) | 5300 | 0.42% | 0.12% | 28% |
| Helper 14 (Synth. Ψ) | 8100 | 0.29% | 0.06% | 21% |

3. Construction of Modified Backbones

Constructions are based on plasmid stk120 (Morsy et al., 1998, supra) containing a CMV promoter driven gfp (green florescent protein) gene within the stuffer sequences at a unique SwaI site (stk120gfp). In order to incorporate the additional elements into the helper-dependent adenoviral vector, the 3' ITR (130 bp) was extended to 400 bp from the right end of the Ad5 genome. This fragment contains the complete E4 promoter region. However, no adenovirus coding sequences are present. The resulting adenoviral vector is stk120gfp-E4-promoter.

In a second construct, a 1353 bp fragment from the right end of stk120gfp containing part of the stuffer sequence and the 3' ITR was replaced by a 3115 bp fragment of Ad5 from a MunI site to the end of the genome (stk120gfp-E4). This fragment contains the complete functional E4 region.

4. Competition Between Helper-Dependent Adenoviral Vectors

Genomes for stk120gfp and stk120gfp-E4-promoter were released from the respective plasmids and cotransfected with a circular plasmid containing the entire helper genome into 293 cre cells at a 1:1:2 ratio followed by infection with helper virus at moi 1.

Figure 2A:
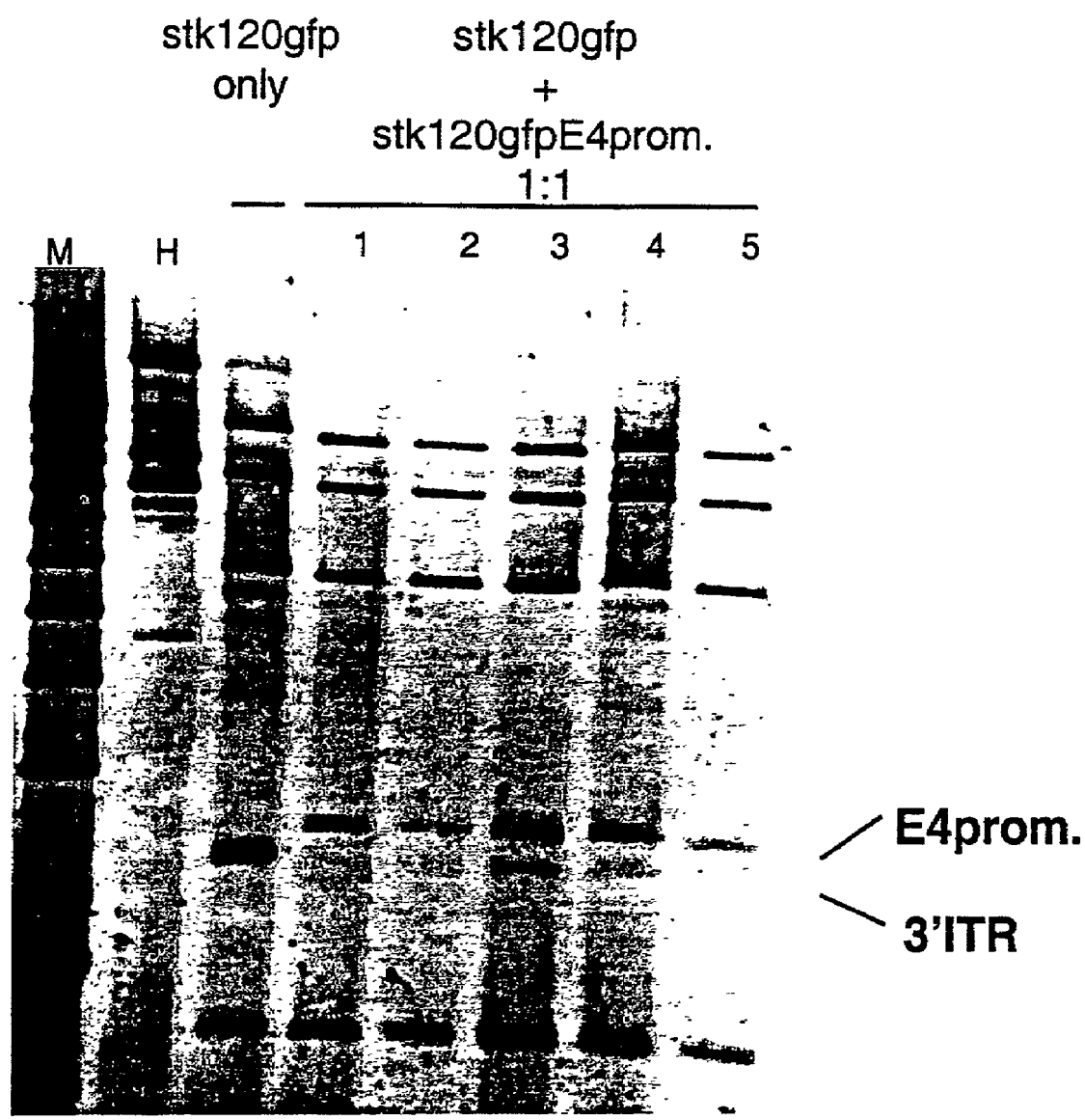
FIG. 2 is a gel showing restriction digests of helper-dependent adenoviral vector DNA after competitive rescues of: a) stk120gfp-E4-promoter and stk120gfp; b) stk120gfp-E4 and stk120gfp; and c) stk120gfp-E4-promoter and stk120gfp-E4.

The mixture of viruses was amplified up to passage 7 where the viruses were Cs-purified. Five independent experiments were carried out. Virus DNA was extracted and analyzed for presence of the two virus types. In all experiments a 5–10 fold excess of stk120gfp-E4-promoter was found (FIG. 2a). This indicates the presence of a cis-acting sequence located next to the 3' ITR (right virus end) which supports helper-dependent adenoviral vector growth.

An identical experiment was carried out to determine whether the complete element is located within 400 bp from the right virus end or sequences further upstream contribute to this feature. stk120gfp-E4-promoter and stk120gfp-E4 were cotransfected with the circular plasmid containing the entire helper genome (Helper 14) into 293 cre cells at a 1:1:2 ratio followed by infection with helper virus 36 hours after transfection at moi 1. After passage 7, viruses from three independent rescue procedures were purified, DNA was extracted, digested with BsrG1 and labeled. The discriminating fragments have equal strength for each rescue (FIG. 2c). Therefore, the cis-acting sequence supporting helper-dependent adenoviral vector growth is located between nucleotide −400 from the right end and the 3' ITR.

Example 3

Construction of Helper-Dependent Adenoviral

Backbone Containing Alternative Stuffer Sequences

The construction of the new helper-dependent adenoviral vectors (group A) began with the ligation of a 3498 bp from fragment from pSTK120 (which comprised of the bacterial sequences origin of replication and ampicillin resistance gene, the right and left ITRs and the packaging signal) ligated with a multiple cloning site linker (SEQ. ID. NOs. 6 and 7) containing HindIII sticky ends and cloning sites EagI, AscI, BglII, NotI, Xba1, Mlu1, EcoR1 and Kas1. This clone is named "pITRF".

DNA from the region encompassed within HUMDXS455A (Genebank Accession # L31948) used as stuffer DNA was amplified from human genomic DNA in four segments of about 4.5 kb each using the following pairs of primers:

| | |
|---|---|
| SEQ. ID NOs. 8 and 9 | (PCR1) |
| SEQ. ID NOs. 10 and 11 | (PCR2) |
| SEQ. ID NOs. 12 and 13 | (PCR3) |
| SEQ. ID NOs. 14 and 15 | (PCR4) |

PCR1 product was Klenow filled in and then digested with Asc1. It was ligated directly into the Asc1/EcoRV of pITRF to produce "Construct 1".

PCR2 product was digested with Not1/Asc1 and cloned into the Not1/Asc1 site of Construct 1 to produce "Construct 2". PCR3 product and Construct 2 were digested with Mlu1/Not1 (double digest) and ligated to produce "Construct 3". The PCR4 product was first cloned into a TA cloning vector.

To avoid inefficient direct cloning for very large plasmids homologous recombination in *E. coli* BJ 5183 was used to insert PCR4 and additional genomic fragments. The technique requires a small shuttle vector containing the region which overlaps with the insertion point in the large plasmid. This shuttle vector was constructed as follows: 2 kb of the junction over PCR3 and vector sequence was amplified using Construct 3 DNA. The PCR fragment was Klenow filled in and then digested with Sap1 enzyme and ligated into PABS helper-dependent-3.0, a small plasmid vector (KanR) cut with EcoRI followed by a fill in reaction using Klenow and a digestion with Sap1. Homologous recombination between Construct 3 and the shuttle resulted in Construct 4 (C4).

The helper-dependent adenoviral vector part of C4 is 20 kb in length and has 3 unique restriction enzyme sites to incorporate 3 different transgenes (Asc1, Not1 and Swa1).

As a next step, a CMV promoter driven gfp gene was inserted into the NotI site of C4 by homologous recombination. For this purpose, a shuttle vector was built containing 2 kb of C4 overlapping the NotI site (pNot). The gfp expression unit was inserted by blunt end cloning into NotI and a fragment of this vector was used for homologous recombination with C4. Because a single NotI site is also present in the gfp expression unit, the gene can later be replaced by other genes using this restriction site. The gfp gene is located at a junction between 2 inverted genomic fragments which prevents insertion into the host genome by homologous recombination which would be likely, if the gene was inserted within a contiguous sequence.

To incorporate additional stuffer sequences and extend the 3' ITR to include the E4 promoter, a second shuttle based on pABSHD-3 was constructed containing 2 kb of C4 including the 3' ITR and unique KasI, SalI, BglII and HindIII sites for insertion. The E4 promoter was directly cloned as a Hind III/SalI fragment into this shuttle vector.

Figure 4:
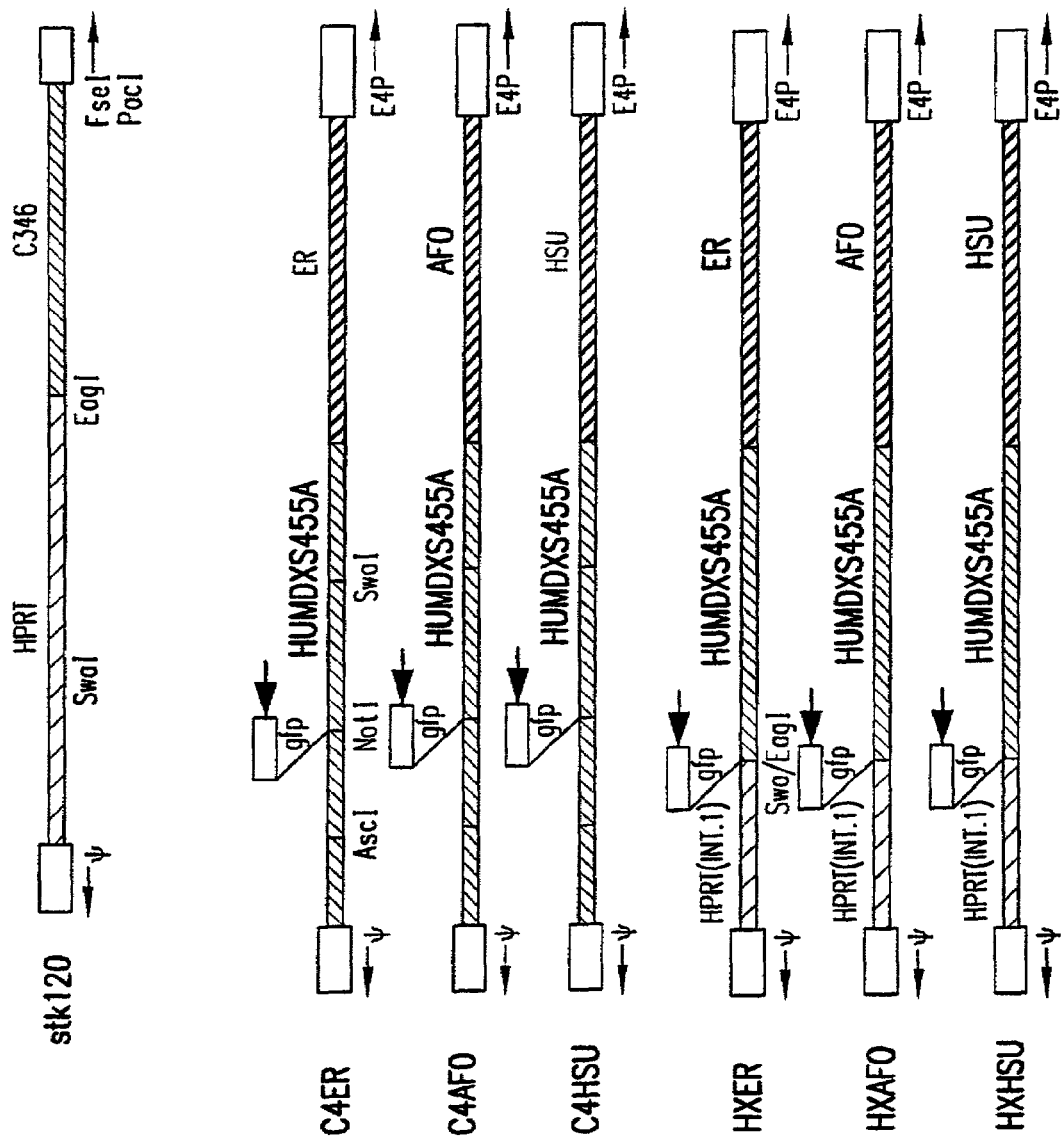
FIG. 4 shows the structure of different helper-dependent adenoviral vectors.

Stuffer DNA fragments AFO, HSU, ER1, and ER2 (FIG. 4), were amplified from human genomic DNA by PCR Expand Kit (Boehringer) and cloned into the Topo-blunt vector (Invitrogene). AFO and HSU were inserted individually as SalI fragments, the ER1 and ER2 fragments were inserted sequentially after KasI/BglII and BglII/Sal digests. Recombination in *E. coli* BJ 5183 lead to the final backbones C4HSU (SEQ. ID. NO. 16), C4AFO (SEQ. ID. NO. 17), and C4ER (FIG. 4).

Construction of the new helper-dependent backbones (group B) was started by replacement of a 8181 bp fragment from stk120 by the gfp expression unit. For this purpose a shuttle vector was built based on pUC 18 containing 1 kb 5' to the unique SwaI site and 1 kb 3' to the unique EagI site in stk 120. The gfp expression unit was inserted into the Bam HI site of this shuttle as a BglII fragment. The replacement was carried out by homologous recombination in *E. coli* BJ 5183 between STK 120 linearized with EagI and a fragment of the shuttle vector. This step removes a part of the hprt region from the vector which was most frequently lost during adenoviral vector propagation. This vector "STK-SEgfp" is 19.4 kb in length and misses about 10 kb of genomic sequence required for propagation as a helper-dependent adenoviral vector.

Fragments AFO and HSU were cloned after SalI digestion into the SalI site of shuttle vector pSH1-3ITR which contains part of the HUMDXS455A-fragment in STK120 and the 3' end of Ad5 starting from nt −400 containing the E4 promoter and the 3' ITR. The fragments ER1 and ER2 were inserted step by step into the same vector as SalI/BamH1 and BamH1/BglII fragments. The 3 resulting different shuttle vectors were recombined with STKSEgfp linearized with PacI to generate HXAFO, HXHSU and HXER (FIG. 4).

Example 4

Generation of Helper-Dependent Adenoviral Vectors

Cells from subconfluent plates were washed with PBS, trypsinized and seeded to 6 well plates (Costar) at $3 \times 10^5$ cells per well in 1.5 ml medium. Genomes for helper-dependent adenoviral vector were released from the respective plasmids by Pme I digestion and 2 µg of DNA were cotransfected with a 2 µg circular plasmid containing the entire helper genome per well. A 24 hour transfection was followed by infection with helper virus at 1 moi. Forty-eight hours later cells were lysed by 3 freeze/thaw cycles and the lysate was used to infect $10^6$ 293cre cells together with Helper virus at MOI 5. Cells were lysed 48 hours later.

The same procedure was repeated with increasing the number of cells until passage 6 at which two 15 cm plates are infected. At this stage helper-dependent adenoviral vector is isolated by CsCl banding and analyzed by restriction digestion. Passage 6 is also used to infect a large scale preparation (1×10 layer Nunc cell factory).

Example 5

Competition Between Helper-Dependent Adenoviral Vectors

Virus rescue in a competition experiment was performed using the procedures described above and, instead of DNA from a single vector plasmid, a equimolar mixture of 3 vectors was used. Three mixed rescues were carried out: one with HXAFO, HXHSU and HXER; one with C4AFO, C4HSU and C4ER; and the third with HXHSU and C4HSU. No rearrangements were observed in either the individual or the mixed rescues.

Figure 5:
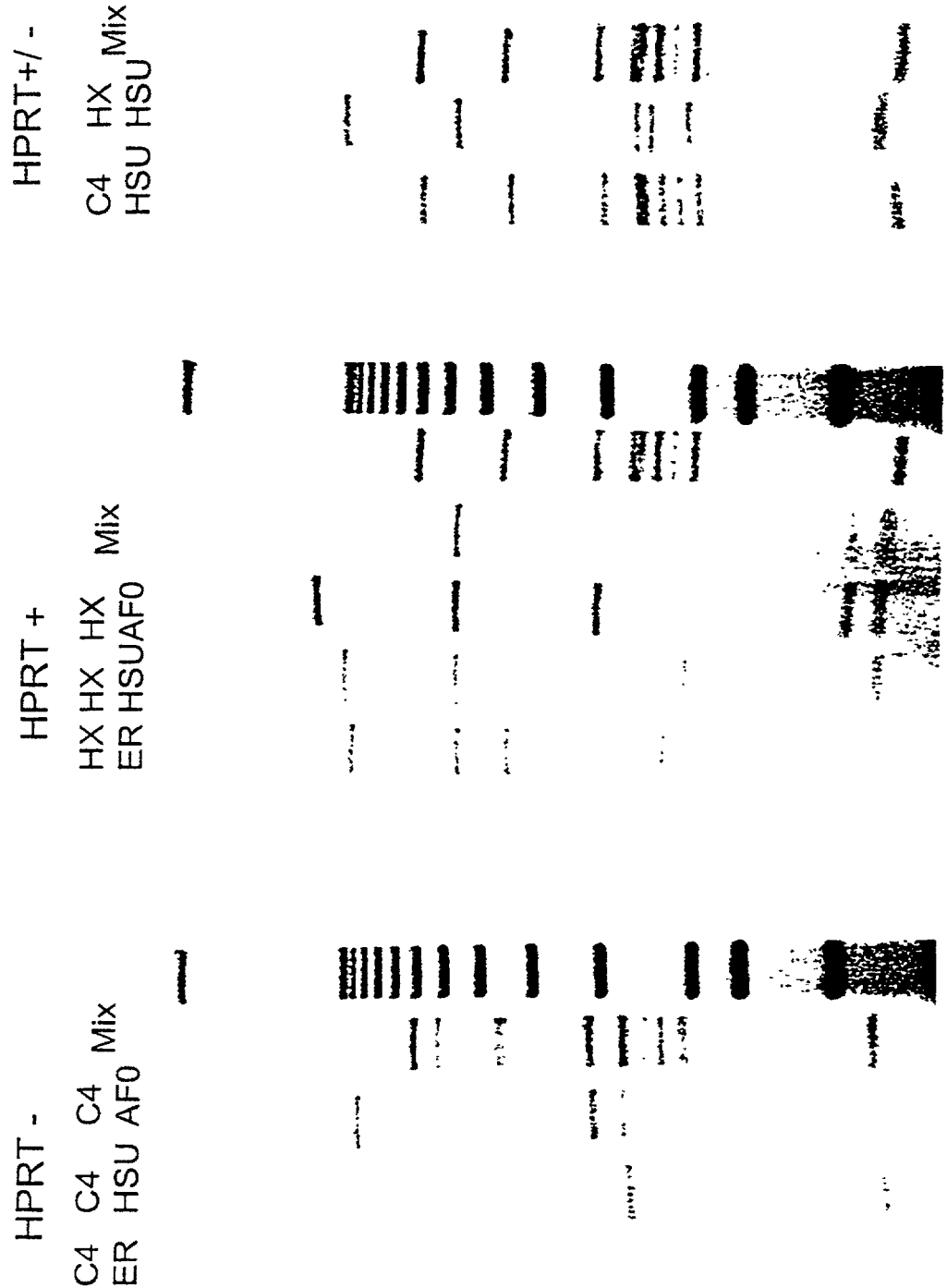
FIG. 5 shows autoradiographs of labeled restriction fragments from helper-dependent adenoviral vectors. The figure illustrates the results of competition experiments involving groups of helper-dependent adenoviral vectors from transfection to passage 6. "A" is a competition of backbones containing the shuffled fragments of cosmid HUMDXS455A (C4). "B" is a competition of backbones containing part of the HPRT (hypoxanthine guanine phosphoribosyltransferase) genomic gene. "C" is a competition between 2 backbones one containing part of the HPRT genomic gene the other containing the shuffled fragments of HUMDXS455A (C4).

As shown in FIG. 5 there are only moderate differences between backbones within the first 2 groups with a slight dominance of the C4HSU construct. However, in a competition experiment between HXHSU and C4HSU the latter clearly dominated. Thus, the remaining hprt sequences in HXHSU have an adverse effect on adenoviral vector propagation.

Example 6

Analysis of Large Scale Preparations of Helper-Dependent Adenoviral Vectors

STK120-EF1amEPO, C4AFO-EF1amEPO and C4HSU-EF1amEPO

To investigate the behavior of the new helper-dependent adenoviral vector in vivo, the gfp gene was replaced in STK120, C4AFO and C4HSU by the in mice immunologically inert mEPO gene. Replacement was carried out using the shuttle pNot by homologous recombination. Viruses were rescued as described above. Large scale amplifications were carried out in Nunc cell factories and the virus was purified as described above.

Since the size of the helper-dependent adenoviral vector and the helper differ only slightly, the purification procedure does not remove helper virus from the preparation. Such a physical separation was not intended to allow for a replacement of gradient based by chromatography based purification in large scale. DNA was extracted from purified virus and the content of helper virus relative to the amount of helper-dependent adenoviral vector was determined by Taqman™ quantitative PCR.

Figure 6:
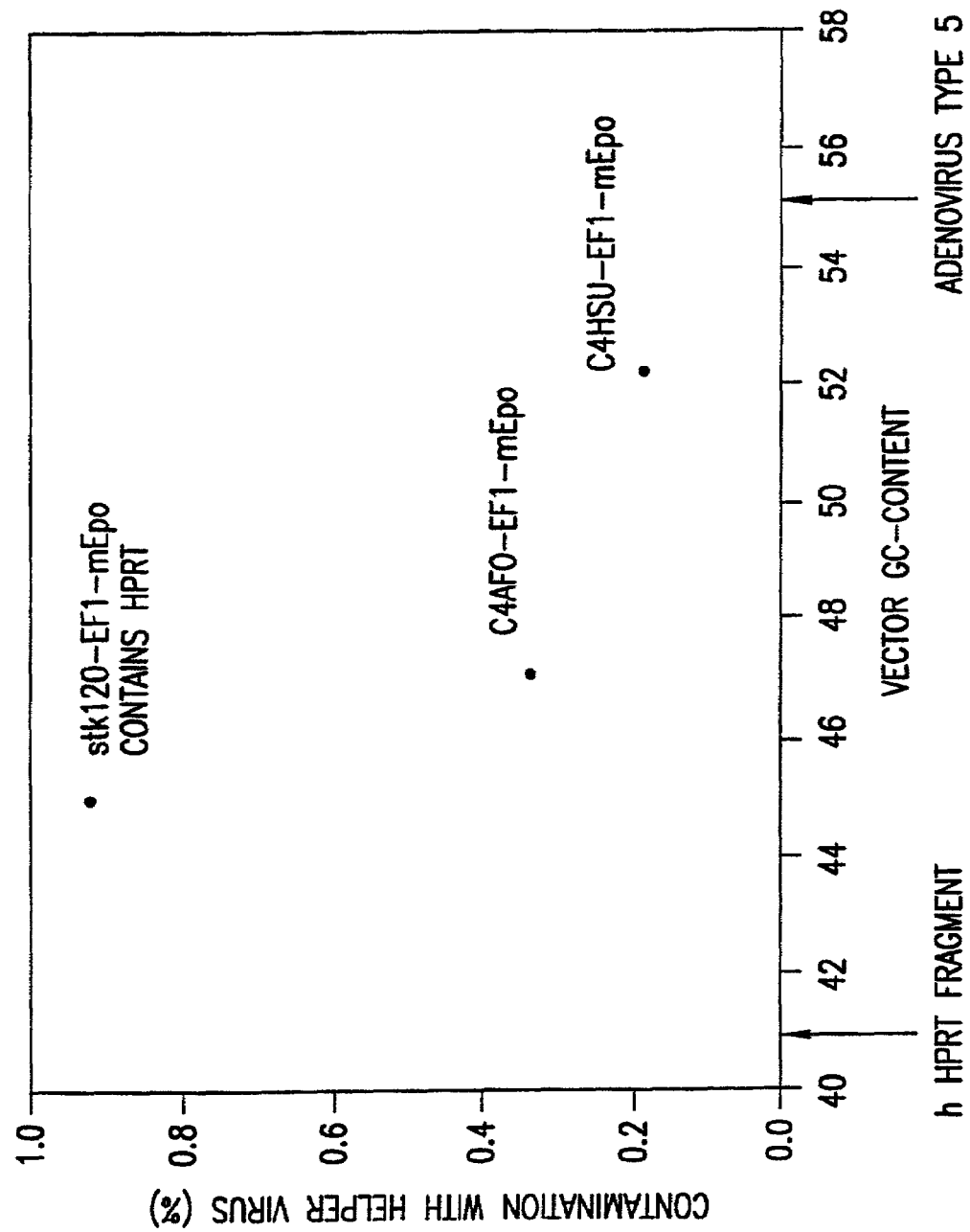
FIG. 6 is a graph showing the correlation between GC content and helper virus contamination.

We observed a correlation between the helper content and the GC content of the helper-dependent adenoviral vector (see FIG. 6). The experiment with Construct C4HSU has the lowest helper content (about 0.18%) compared to a helper content of about 1% for stk120.

Example 7

Analysis of the Replication Potential of Different Helper-Dependent Adenoviral Vectors Cells were infected with 100 part/cell of helper and 300 part/cell of the helper-dependent adenoviral vector. Three hours after infection ⅓ of the cells was harvested and washed with PBS. Another portion was harvested at 42 hours and a third fraction at 48 hours. Cellular DNA was extracted as described above and the relative amount of helper and helper-dependent adenoviral vector DNA was determined by Taqman™ PCR (FIG. 7).

Figure 7:
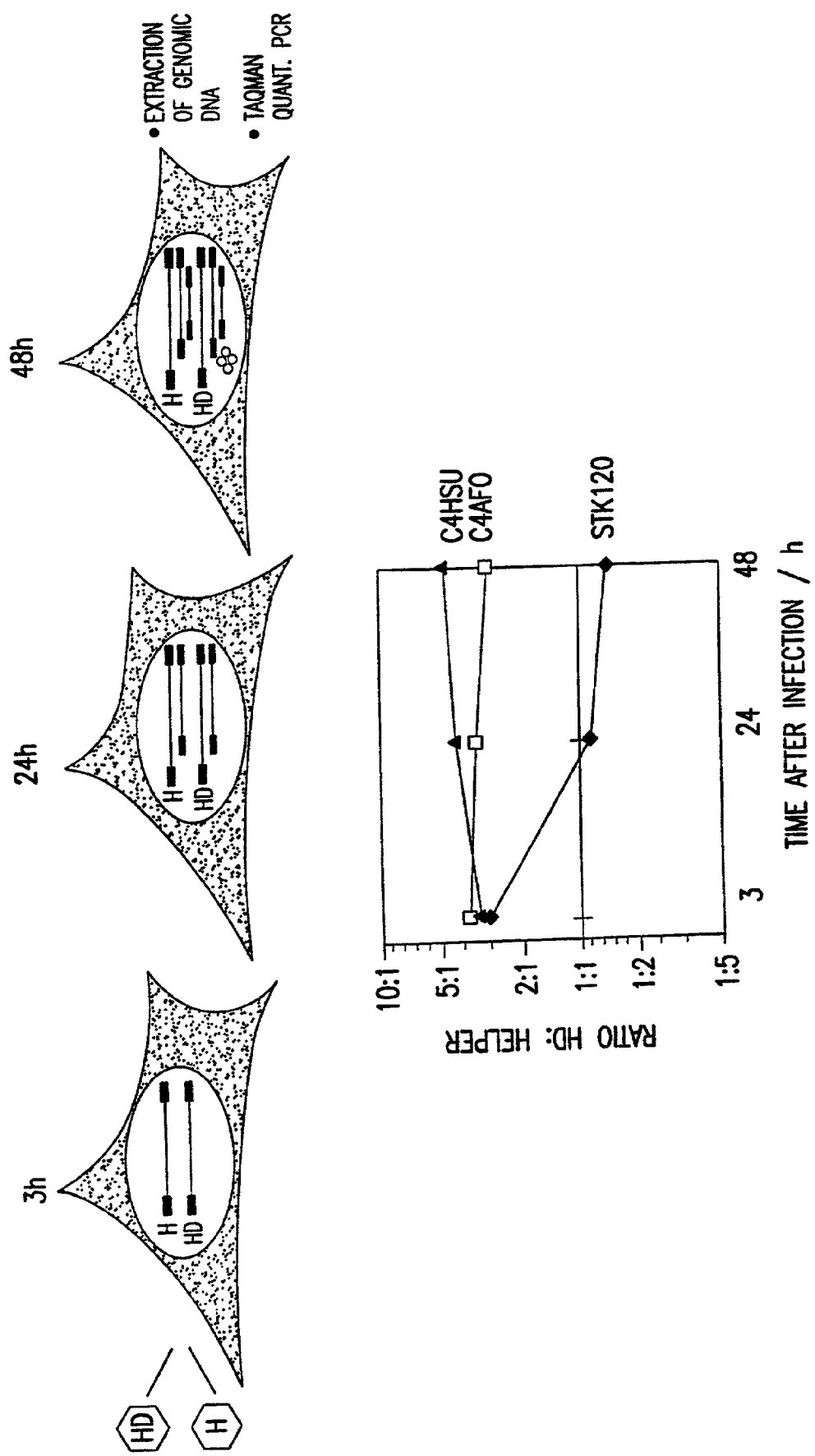
FIG. 7 is a graph showing the balance between helper and helper-dependent adenoviral vectors at different time points after infection. The figure demonstrates the replication potential of different helper-dependent adenoviral vectors with the mouse Erytropoetin gene relative to the helper virus.

FIG. 7 shows that if the rescue is started with an excess of helper-dependent adenoviral vector, the ratio of helper-dependent/helper is maintained and even slightly increased for C4HSU, whereas it is strongly decreasing for STK120 and slightly decreasing for C4AFO. This shows that the nature of the backbone has a strong impact on the speed of replication. Whereas the Adenovirus genome coevolved with the adenovirus polymerase, the helper-dependent adenoviral vector sequence was artificially selected. Therefore a less efficient replication is expected. However, the most important determinant seems to be the GC content of the helper-dependent adenoviral vector.

Example 8

Sequence Information

The different sequences for the SEQ. ID. NOs. referred to in the application are as follows:

SEQ. ID. NO. 1
ATTTGNgGC

SEQ. ID. NO. 2
ATTTTGTGTT

SEQ. ID. NO. 3
ATTTTGTTGT

SEQ. ID. NO. 4
GTACACAGGA AGTGACTTTT AACGCGCGGT TTGTTACGGA

TGTTGTAGTA AATTTGTCTA GGGCCGAGTA AGATTTGACC

GTTTACGCGG GGACTTTGAA TAAGAGCGAG TGAAATCTGA

ATAATTTTGT TGTACTCATA GCGCGTAATC TCTAGACG

SEQ. ID. NO. 5
GTACA CAGGAAGTGA CAATTTTCGC GCGGTTTTAG GCGGATGTTG

TAGTAAATTT GGGCGTAACC GAGTAAGATT TGGCCATTTT

CGCGGGAAAACTGAA TAAGA GGAAGTGAAA TCTGAATAAT

TTTGTGTTAC TCATAGCGCGTAATCTC TAGACG

SEQ. ID. NO. 6
AGCTCGGCCGATTATTGGCGCGCCAGATCTGCGGCCGCTTCTAGAAACGC

GTGAATTCGGCGCCA

SEQ. ID. NO. 7
AGCTTGGCGCCGAATTCACGCGTTTCTAGAAGCGGCCGCAGATCTGGCGC

GCCAATAATCGGCCG

SEQ. ID. NO. 8
ATTGGCGCGCCTTCTTTCTGGGATGATTCAGCATCAACTC

SEQ. ID. NO. 9
GATCGTCGGCCGCTTGGGTCATAGACTTCTTTGAGAACCAG

SEQ. ID. NO. 10
ATCAGTTAGCGGCCGCACAAGCTAAGATCACAAAGCTGTTT

SEQ. ID. NO. 11
TATGGCGCGCCGCTGACACCCAGCCTGGGTGCCGGTG

SEQ. ID. NO. 12
TCGACGCGTAGCGCTGTGTGGCCTTGGCAGTTTCCATAG

SEQ. ID. NO. 13
TCAGTAATGCGGCCGCGGGATCATTCCTGGACTCAGATTGTTCTG

SEQ. ID. NO. 14
TATTAAGGCGCCGGGCATGGGAGTGATCTCACCAACTCTGG

SEQ. ID. NO. 15
TCGACGCGTATTTAAATGTGCTGGAGTGTTGAGATACTGTAGTGGT

SEQ. ID. NO. 16
Helper Dependent vector C4HSU
The sequence is shown without transgenes.
AAACATCATCAATAATATACCTTATTTTGGATTGAAGCCAATATGATAA

TGAGGGGGTGGAGTTTGTGACGTGGCGCGGGGCGTGGGAACGGGCGGG

TGACGTAGTAGTGTGGCGGAAGTGTGATGTTGCAAGTGTGGCGGAACAC

ATGTAAGCGACGGATGTGGCAAAAGTGACGTTTTTGGTGTGCGCCGGTG

TACACAGGAAGTGACAATTTTCGCGCGGTTTTAGGCGGATGTTGTAGTA

AATTGGGCGTAACCGAGTAAGATTTGGCCATTTTCGCGGGAAAACTGAA

TAAGAGGAAGTGAAATCTGAATAATTTTGTGTTACTCATAGCGCGTAAT

ATTTGTCTAGGGCCGCGGGGACTTTGACCGTTTACGTGGAGACTCGCCC

-continued

```
AGGTGTTTTTCTCAGGTGTTTTCCGCGTTCCGGGTCAAAGTTGGCGTTT
TGATTCGGCCGCTTGGGTCATAGACTTCTTTGAGAACCAGTTATAAGCT
ATGGTTTCTCTCCACAGAAAAAGCACTTATGGTGTCTCCCCCTTTCCAG
CCCACCAACATTTTACATCTAATTTGGGGGGGTTTTCTGGACCACTTAA
TACCCATCCATGGATCTCATGTGAAGACTCCCCTGGCTTGAGAAATCAC
TGTCTTGTTGAAAATGGGAACAAAGCTAAGTCAGATAGCTGGTTCATCA
GCAATGACTTTGACCAAGCCTGATCCCACCCTACCCCACCCCACCCCAG
TGACCACCCCCCACAATGGAGCACACAACTCTAAACTGGTTTGTAGGTA
TGTGTGTGTGAACACGCTGAGGAATCTGCAAAACCAAATGGTGAGTGCA
AAACCAAACAGTCACGAGTAAATCTCACAACAACCACGTCCTGAGCTGC
AGCCCTTGTTGAACTATACCCCACTAGGGCCCCAAGATTTTAGGACTTG
TGTGTGGGTGGGACCTCCCCTTTCTATCATGCTTTAGAAGACAGGGATT
TCACCAGAATTGAACATATTGAACATATGACCCATTTTTTTCAGCCAAA
GGCAATTAAAATAACTTCATACTTGATATCCATGTCAGCAAAAGCTGCA
AAACGCAAATGGGTGGCTGCTAAGAGCCCTGGTACCCTGACGAGCACAC
CAAGTGCTTAGCAACAGTGGTGTCCAAAGGACCAGCTGGAAGCCTGCCT
TGATGAGAAGTTGCTCTTCTTTCTACATGAAGGAACACCTCTACTCTCC
TGCTTTTAATACCTGAGCTGTGAGTGATCATCTATGTCCATTAGCAAAC
ATCCCAGTGGAGAAGGAAACACTCATACCCGAAATCTAAGCTACATAGT
TGGAATCACTTCAACTTATTGCAATAAACACTTACTAAGCACCTATTGT
GGGCAAGTCTTTGCAATGGATAATAGTTCAGTAGATATTTTGATGTAAT
ATTTGAAATAACAATAAAAATTGCCACCACTGAATTTATTGAGCATTTG
CTGTGCTTTAGGCACTAACCCAGGTTCTTTAAATATTTGGTCTTATTCG
ATCTGTATAAATAGCCATCTATGAGAAAGGGACTATTATTGCCCTTATT
TTACAAATGAGGCCAATGAGGCCCAGAGAGGTTAACTAAGTTGCCCAAA
ATCATACAGCCCACTAGTGGCAGAGCAGGATGCAAACCCAGGCTTGCCT
CGTTCCCAAGCCCACATGTCGTTTGCATTGGTGTGGAGGTGTGCATGTG
TTTAGTCATTAGCATGTTATATGATAAGCAAGTTTTGAAACATAGAAAC
TTAAAATGTGCCATTAAGAAAAGTACAGGCAAGGTTTTCCAAGGGGAGG
TGTGGACCTCCGGACAAATTTTTAAGAACTAATTATAAATACTTAAAAA
TGGGAATAAGAAGACAACCTAACTACCTGAACAGTTTTAGAGATGACTC
ATGCCCACCCTCTAAAACCCAAACAAAAACAACAAAGTCAAGAAAACCC
ATGAAATCTTAGCAAGCGATTTCTATGTACTTGTGAAAAGGATTTCTTT
ACCATTCTAATGGGATTTATGCCAACCATAGAGGGCTCAGTGCCCCTCC
CATGGGGTGGTTAGTGAGTACAGAGCTGAGCTCACCGGCCATCTGCAGC
TTCATGTTATCAAGCTCCAGTTTGTCCTTGGAGCAAGGTTATCTGGGAC
ATGAGCAGAGGCATTGCTTTCTGCAATGGACAGTTCTTTCTGCCTGCAT
ACCTAGCTCCTTGATAACTTTAAATACCATTTTATAGCCACACTGGAGT
TTTGAAGACCTCAATATGCAAATATTACTCAGGTTCTGATTACTTGTCT
GCTCCATGATAACACACTCTAAAAGCAATGAATGGGCTTATTTGTAGA
GAACTGAAGCATTTTAAGCTTTTGCTCAGGAATCCCTGGTAGCTTCCTG
TGACTTGCAAGATATTAGTGATGGGTCAAGAAACAGGACCCCCCATCAG
CATAACATACGCAGTGCCTCAGTAGTCCATCAGGCAGAAAAAACTGCAG
ATGGCACATGGAAATGACCAGCGGCGGAAGATACCCCGACAGTGTGGGC
AGTTCTATTTCAGCAGCAATCAAGAGGGGGCCTGGAGCCACTCAATCAA
GTGGAGCAGGATGGGAGCAAGCACTGTGCAGACCAATGCAATCCCCAGT
TAACACAAAAAATAAATAAAAGAGATGAGATTCAGTCTCTTGACTGTGA
CTGACTGGGAGCTTTATAGCTGATGCTTGTGTCTTTTCTCCATTTTATT
TAATTAGGAAAAGAAATGCTTATCACACACTCTACGTGTGAGGTACAAC
CTCCACAGGAAAGGTTGTTAGGAACATTTCAACTTCTAGAAGTTTCTAA
ACATAAGGTAAATCCATCTTTGTCCTTGGGATCACTGCACATCTCAGAA
AGGCAAATAAATCAGTAATTGGTGGGCATAATTACTAGCTCATGGACTG
ACAAGGTCTACACTATTTCGAATCTCACAGAAGTAAGCCATGGGACAGA
TAGAGTCTGATAGTGGTGCCCCGTTTCCTGGAGGTCACACTTACTCATC
CCCCTGGACCCTGGGCTTCTCATGATTGTCAGAGAGTTTGCTGGAACCA
GGTCAGCCCAGTTTCCCTTCCCCTGAAAAATCCTCCAATGGCTCGCAC
CAAGACTAGAGATGCAAGTGCAAGCACATCCACCCTCTCAGCAGCCAGG
TTTTGCGTTCCATAATGTCACGTACCCCCAGTCATACCAATCTCCTTGG
AGCTCTCCAGACAGGCTGCCATGTGTGGTCGGCCCTCTGTGCTTGTGCT
CCTTGGTTTGCCAAGCCTGGAATGCCCTTTCTCCATGATTGTACTCTGG
GAATTCTGTGTGTCTTTCGAGATGAAGCTCCTCCACCCTGGAAATTCTG
CCTCTCTTTCCAGGTCCAGCTCCTGTGGCTGAATACCCTTGGCTGACTG
AACATTCTTGCTGGGCAAGTCTTAATCATCTCTAAATCCCTCTGGTGC
CCCGACAGTATCTAGCCCAGGCAAAGGGCTCAGCAAATACTTGCAAAAT
TCAATAAACTTTACTATGTTACTAGCTTGGCATGATGTTCTAGGCACTT
GGGAGATTATAATCTGGTGAGCATTGTGCTAGTCTTTTTTTTGGGATAA
ACACCAATGATAAACTGAGCCTTTACTCTCATTTTAGCACATCTACTCA
TGTCTTTTCAATGCTGGTGGGTTTATAAAACCCATCAGTAGAACAGAGA
GTGATCATAATCATATGGTGAAAATAACATCAGCTAACATATTTACTGA
ACATGCTTTAGTGTGCTGGGCACTGAACTCTGTGCACATGTGAATTTGA
GATAGATTGTTCCTAGCTAATAAGATGAGGAAGTGGAGATGGGCTTACT
CAAGTCACACAATAGCAAGATGGGGTACAGACAGAAACCAAGCTAGAAA
CCAAGCAACCCCTGGGTTTGGAAATGCATGGGCTCCTCCTCTGCACATG
GCGAGGAGCAGTCAGGTGCTCCTCCTTCTCTCATACTGAAATAACTCTG
CACTTTTGGCTATTCTGTGACACTCTGTGCTATTCTGTAGCTCAAATGG
CTCTGGTGCAAGGAGCTCAGATTATGACTAACCCCCATAGATATTCAGC
TGCTTTGCAAGAAGTGGATGAATGCTCTGGCTTTATAAATTATTGACTA
GATTGGATATTGGCCCAATCTCCACTCTGGTGATTCGGAAGGAGGCATA
TGCACATTTGCAAGGTTATAGTAGTGCACTCTAATTCCACTGGCTTCTG
AGAGCTTGTAGGTTTCTTGACTTAATCATTCTGGAATTAAGGTAATGGA
```

-continued

TCCTCAACACCTTTTCTTTTCCCTGGCCTTTACTAACCATGTAACAGAA
ATGAGCAGAGAAAACCCAAGAAAGCGAACTGGAGACTTGATGAGTGTGT
CAAAGATGCTCAGAGTCCAAGGTCCTCTGTGGCTCACTGACTTCAGAAG
CCAACCTCCGTTGTTCAAGTCACTTGTGAGGTTACTATGCTAGAGCACT
AAATATTATCCAGATAGCCCAAAGAGGTGAAGGCAGACATGTGGAAGAA
CCTGGATTTTTGGGCAAGTTGATGAATGCCTCCTGCCCCATATCAAAGA
GAGGTGATAGGAGACAACTTTGTGAATTTGAAATAATGCACCGGGGAAA
CAGGAAAACGTAATGTAAGTCACGCTTCTTGGCTTTTTTCTTGCCATTA
CCCTACTTGGCCAAGTGCAAATGGGATTTCAATATATCATAAGTATGCA
TCTATTAATAACAATGCAAGAAAGCTGTACAACTGAAGTCTGAGATTTT
GTAAGAAACAGAATCTCTGTAAGCATCACCATCCAACAGAACTTCCTGA
GTTGATGCTGAATCATCCCAGAAAGAAGGCGCGCCAGCTCTGCAGGATC
TTCAAGTCTGGGGTGCCACCAGCAAGCGACGGTCCTCCATGGGCTCTTC
ACCTTACGGCAGTGTCCAGAGGCACCGCCAGTCCTCTGCTCCTATGCTG
GTCCTGCTGTCCCTGGCAAAAGGAGCCAGAGCATTCTCTCCAGGCCTCC
CGAGGAGGCTGCTTCCTTTGTTTTGCAGATGGAGGCTCCCATCCTTTGT
TCTGAATCAATGTGCTCCAAAGATAAGCCCCAAGAAAACAGTTGTTGCC
TTTTGACACTGACAATTAGAATCGTTGGAAAATGGAGAAAACAGGAAAT
GGCAAATGGTTTCAGTGACCAGGAGGAAACCGTGCCTGAAAGTTGCTGC
TTAGTGACTGGGACACTCGCTTTCTGCTCTCTTATGAAGGACAGCCTAG
GCCGTGTGGCCTTTTATAAACAAAGCTATGAAGGGGTCGTCAAATTTTC
TAGGGCTGCAACTGTGGCACTACGTCCTGTTGTGCCAGGTGACACTGAC
AAGCAGCACTGAGTTCTATGCAAGCCCAGGTGTGCTTCTCTCATGGTGA
CCCCCAGAGAACTAAGGCCCAGCTCTTCCTCTGTCACACCCCTCCCAGC
CCCCACTGTCAGACAAGGGACCACATTCACAGACAGTCTCAGCCAAGAT
GGCAACCTTGGAAGTCCTGGGGATGCCTTTCTAGAAGCTTTAGGCTGAC
GCCAGGGAGCTGTAAAGCCCCCACCTGTCCCTGGGGGTTGTGTGCTGGG
CAGGAGAGAGGGGAAAGAGCCCAAACTCCACCACTGCCTGCTGGCACAA
CTGAGCCCACGCCAGGCACTGCACCAGCTTCACTCACCAGCTACCACAT
GCTAATGTCTCCTGTTTACCCAGGTGCAATCACCTGAGTGCTGCTTTCT
CACCACTGCATGGGAAGAACGATCTCATTACCAATTCAACCACTTAAGC
AGGCAAAAGGACTCCAACGGGGGAAAGGCAGAGGACAAACGATTCGGGG
ACTGAGACAGATGCCCACAAAATGTTCCTGGATTTTAGCCGGATTCGGG
CTGAAGTTCCTTGCCCTATGAGCCCTTGGAGGAGAGCATCCTGACTCAG
ACAAGAATTCAAATGACAAGACTTCTGGGGGATGGCAGTGAATGGATCC
AAAGCCTTGTTTTATAAAGAATGTGGAGGAAGGGAGGAAGGAAGGGAGG
GAAGGGGAGACTGAGAGGGAGAGAGAATAAAGAAGAGGAAGAGAAGGAA
GAGGAGGAGGAGGAAGGGGAGGGGAGAGGAAAAAGGGGAGGGTAGAGGA
GGAGGGAGAAGGGAAGGGAGGACAGAAGAGGGGAGGGAGCGGGGAGAT
TATCTACCCCTCCATGCTAGGGAACTCCTGTCTCCTTTTCCAGCAGACA

-continued

CTGCTCCATGAGTGCCCCCACAGAGAGCCAGCCTGCCACACAGCAGAAG
GTGCTCAGCTATCTGTCCCAAAGGTTGAGCACTAGTGTATACCACAAGG
AAAAAAACCTTCTTTTGTACTGTTTGGAAGCCAGAATTAGAAACAACTC
GTTCACCCTTCTGACTTTCCCTTTGCAATGACAGGAAGATAGTATACTG
CATGGGACCACCACACATTCAAGATCTGAGTTGTGGGGACCCCCACCCC
CACATGGGTGGAGCCCCCTGAGACCCGTGGGCTCTGACTGGCCATGGCC
CATAGATAGTGACAACATACACACTGCTATCTGAAGCCTAGTTGGAGGA
CGGATGGATGCTTTTAGGAAAAAATTCCCTTTAGTCGTCCCTCAGAAAC
TACAACGGCTTCCTAAAATGAATGGCAGGCAAGTTTTGATTGTTTCCTA
AGTTCCCCCTAACTCTCAGAGCCTGTGACTCAGCTTCTCCAGAATGCCT
GCAGGGAGGCAGGACCACTGGGAGTAATGAGCACGAATTGGGCCACTTC
TCCCAGTGGACTGTTAACGCCGAGATCTGGGGTGGAACCCACTGAACAC
CTGCCCTTTTGCGTTGCCCAGAATGCAGCCAGAGGGATACGGGCCACAG
TAACTCTGGGGCCCCTGAACCTACCTTCCCAAGACCCTGACGGGAAGGT
ATTGCTTACATGACAGTCCAGTCAGTCCCTCTGTCACTCAGTTAACAAA
CATGGTCATGGGTCTACTATGGGCCAGGCTCTGTTCCGGGCATGGGGAT
AACACCGTGTGTCTCTACTCTTATGGACACAAGTAAATCAATCAAAGCA
GATAATGTTCTAATGACCACCCAGTAGGGTGAAGGGATGGAGGGTGGGC
AGGTGCTGGCAGAAACCTAAGGTCAAGTCATGGGACCCCAATGGGGAAC
TGGAAACTGCCACACCATTTTCTATGTTAGGGGTCTTTCCTTGCCCTTC
TAGAGACCTCACCCATGGTAATGATGCTGCCCTCAGGTTTGAACTGGTC
TGAAGCTGTCACTGGGGGCTTCACAAAATGAATGCCACTGAAAGCAAAC
GGCAGAGATCTGTATATGAAATTCTTTTTACCCTTTGTTTTCTGTCTTC
CCACATGATCTATGACTGCTGCAAACTCTATTCTGACTCCTCCTCAGTC
TTGGCCGGTCTGGGAAGAACTTGGTTTAGATGCTGGGAATGATCCCGGG
CAAAGGAAACAAATATATTTCCAGCTTGCTTTTCTTCTTCCCCTGTGGT
GCCTGCATCCTCTGTCTCGCACTGACTCACAGGCTGGACTGACAAAGTG
GCTGTGTTGACAGGGAGGATTTAGTGGATGCCAGGCCTGACCCTCAAAG
GCCCTCAGGTGGGGCCAATTTCCAAGGTTCTTAGAGAAGATTTGGGGCC
ACAAATCTGCTCTGCCACTTCACTGCTGGGTGAAAGCTGTTGGCTTGAG
AAGAGAGAGAATAGGTGAGGGACAATAATTCTCAAGGCAAGCTAGCTGA
TATCCTTTCATTTGTGGCTTCCAAAGACAGGGAAAGGCAAGGCAGACCA
GGGTGGAAACAGCGACATCCTGAGGGGACGACGTCCGTTTTGCTAATTC
TGTTTCCCTGGCAGCTTTGTGCTGGACAAGATTTCTCTGGTTTCAGCTG
AAGAGTGAACAGCTGAGGAGCTCTGTGACTCTGAGAGAGAGAGAAATCA
ATAGCCCTTGAAAGGAAAGCACTGCTTGTTCTTCCAGGCCAGGGCAGGC
AGGATAAAGAGAACAAGGCTGTACATACCAAAGCCGAATTTCCATTAAA
GGCCAGAATCCTGGGAGGCCCTTTCAGCTTAATGACCATCTTCTGATCA
CTATCACTTAGAAAATGTTCATGTCTCCAGTTTTCTCTGCAGATAGTGC
AGACATCCTGTGCACATTGATATTTTATGCACCAGATGCAATTCTCTGC

-continued

```
AAAGGTCCCCTCTGGCTGGTGTCCATCCGCTTGCTCTCATGACCACTGA
TGCGACTCTGGGGGCAAGTCAAGCCATTCCTTCTAGACTCTAGAATCTA
GAGGATGATCCCAACTCACAGGCCTCTTGGACAAGCTTGCTTTGGATTC
CTTCTGCCTGTACTACCCAGACTGCCAGTCCTCCAGCAGGGCAATCCAA
CTTCCTGCCTCTAGGGTGTGGGAGTCCTGGGCGGGGTTTGGAATCCACA
GCAGATGGCTGGCAGGAGAGGCAGTTCCCGAGCACCCACTAGGTGCCAA
GCAGGCAGGTATCAGGTGCAGGGCTTCGGAGGTGCAGAAGCACAGCCCC
TGTCCCCCTCAGGTTCCCAGTCTGGCCTCAGGGACAGACAGGCAGGTAG
GTATGGAAACGGGGTACTGGAAGGCATACAGCTGAGGGAGAGAGCAGCT
GCACCCTGGTCAATCCCCCACTCATTTCCCTGGAGGTGGGGCTGAGGCA
CCTGGAGCACTCTGCTTGCTTGGGTTGTCCCTTTGCCAAAGAATGCCGG
GCAGAAAGTAGAGAACAAGCAGGCCCAGGAAGCACTAGAAGTCCCTCAT
GGGTGGACAGAGCTTTTACCTTCGGAGCTGTCACCTCCTGTGTLTCCTC
CCAACAACCCTGTGAGGCAGGCGGGCAGGCTGAGCAGGGGACTGTGCCC
CGTTGACAGATGAGGAAAGCGAGGCTCAGGGGGAAGTGACTTACCTGTG
GCGTCGCAGCTAGGCAGTAGTGGAGCGGGCACCTGCCTCCAGGCCTTCG
GATCCCAGCTGCCCCAGGGCGCTGCCTCTGAGGTGCTGTACGAGGAGGT
GACTCGGGCCAGCTCATGAGCAAAGGAGCTGCCGGGCAGGAAGGACTCA
CTCCCCAGGGCCTGGCAGGACGGGGGCTGTCGCCCGAGGCTGACCTGGG
GGTGCCTGGCTTCCCCAAGCTTGCAGGCTTTGTCTACATGAGTCTACAA
CAACCGATTGAACAATCCATCAGCTGCTTGGCCACAAAATGGTTCTGAC
TGATCTTGTCACTGCCCTGAGTGTCTAGCTGGGTCATCTGGGTGTTGTG
GTTATACCCACCAACTGCTTTGGTGGAACGAAACCGCGGCCGCGGGATC
ATTCCTGGACTCAGATTGTTCTGAAGAAGCCCAGTTCTGGGTGGCATCA
AGTGCTTGCTAGATGGGGGCTTGCCTTGATCCGGCTACACTTGGAGGT
GACTTGTTCTTGGACGGCTACATACAGAAAGAGAGAAGTGGGGATGAGT
TCCAAAGGCATCCTCGACTTCGGCTGTGGCCACCGGAGGGTAGCTCCTG
GCCCAACACGGACTTCTCACCTCCCGCCCTTGGCTCTCTACTGAGCTCC
CCCCTGCTCCCAATTCCTCGCCATTCCCCTCATTTCTCTGCCCTCAGC
CTGGACTGCAGTTCTTCTGGGAAGCTGCCCCAACTCCCTAGGTCTGTGC
TCACCAAGAGCAGATCACACTGGACTGAAATGCCAGCTGATTTGTCTCT
TCAAGAAAATTGGAAGCTCCTGGAGGTCAGGGTCCATGTCTGCTTTTAC
ACTCAGTGCTCTGTATGCAGGCCTGGCACTGCCCACCCTTTGACAGGTG
GTGCATATTTTGTAGAAGGAAGGAAGGGGCCAGGTGGGGTGGGCTGGGC
TGGTGGCGGGAGCTAGCTCAGCCTCTTAGATTCTCTACCCGATGGATGT
GACCTGGGACAGCAAGTGAGTGTGGTGAGTGAGTGCAGACGGTGCTTTG
TTCCCCTCTTGTCTCATAGCCTAGATGGCCTCTGAGCCCAGATCTGGGG
CTCAGACAACATTTGTTCAACTGAACGGTAATGGGTTTCCTTTCTGAAG
GCTGAAATCTGGGAGCTGACATTCTGGACTCCCTGAGTTCTGAAGAGCC
TGGGGATGGAGAGACACGGAGCAGAAGATGGAAGGTAGAGTCCCAGGTG
CCTAAGATGGGGAATACATCTCCCCTCATTGTCATGAGAGTCCACTCTA
GCTGATATCTACTGTGGCCAATATCTACCGGTACTTTTTTGGGGTGGAC
ACTGAGTCATGCAGCAGTCTTATGGTTTACCCAAGGTCAGGTAGGGGAG
ACAGTGCAGTCAGAGCACAAGCCCAGTGTGTCTGACCCACCCAAGAATC
CATGCTCGTATCTACAAAAATGATTTTTTCTCTTGTAATGGTGCCTAGG
TTCTTTTATTATCATGGCATGTGTATGTTTTCAACTAGGTTACAATCT
GGCCTTATAAGGTTAACCTCCTGGAGGCCACCAGCCTTCCTGAAACTTG
TCTGTGCTGTCCCTGCAACTGGAGTGTGCCTGATGTGGCACTCCAGCCT
GGACAAGTGGGACACAGACTCCGCTGTTATCAGGCCCAAAGATGTCTTC
CATAAGACCAGAAGAGCAATGGTGTAGAGGTGTCATGGGCTACAATAAA
GATGCTGACCTCCTGTCTGAGGGCAAGCAGCCTCTTCTGGCCCTCAGAC
AAATGCTGAGTGTTCCCAAGACTACCCTCGGCCTGGTCCAATCTCATCC
CACTGGTGCGTAAGGGTTGCTGAACTCATGACTTCTTGGCTAGCCTGCA
ACCTCCACGGAGTGGGAACTACATCAGGCATTTTGCTAACTGCTGTATC
CTAGGCCAATAAATGTTGATCACATTTATAGCTGCCATGGTAGGGTGGG
GACCCCTGCTATCTATCTGTGGAGGCTCTGGGAGCCCCTGACACAAACT
TTCTGAAGCAGAGCCTCCCCAACCCCTTTTCCATTCCCTATACCTGACA
GATGGCCCAGGAACCCATTAGAAATGGAAGGTCACTGCAGCAGTATGTG
AATGTGCGTGTGGGAGAAGGGCAGGATCAGAGCCCTGGGGGTGTGGCAG
CCCCCAAGTGATTCTAATCCAGATCCTAGGGTTGTTTCCCTGTCCCATT
GAAATAGCTGCTTTAAGGGGCCTGACTCAGGGAAATCAGTCTCTTGAAT
TAAGTGGTGATTTTGGAGTCATTTAGACCAGGCCTTCAATTGGGATCCT
GCTCTTAGAGTTGGATGAATTATTTAACTGATTTTCAGATCTCCTCTTT
CTCAATGCTTTCAGAAGCACAGTAACTGCTTACTCTGAAATGAATTCTC
ACCCCACTTCCACATATGCACCCCTTGCCCACCCCTTTGGGAACACTGG
CCTTAACTGCTTACCTTCAAATGGACTCATCTGTTGGGAGATATATGCA
TTCTGCCGTTCAGGGGTCATTGCCATAAGACCTGATCTCTGTTCCTCTT
GCTAAACAGAAGATGAAAAGACAAATTAGATTACAGCTACCAATTAAT
AATTAGCCTTAGGATCGCTGCGTGGGGACCTAGGACTTGGCTTTGGTGC
AGCAGAAAGCATGAATAAACACACCAGCATACACTCGCATGCATGCCCC
ACCCTCTCGAGCAAAATTCCACAGGTATAAATAAAGTAAGATTCTGCAC
CTGGGTTAAAAACACAACTGCAACAGCATAGAATGGGCAGGAGAGACA
GAACTTAATAGCAAGAGCACACAGAAAAAAGTTTTAGGCATTTTGGATG
TCCATCTGCTCAGGATGGGTCAGCAGTGAGATGCGGTCACCAAAAGAAC
AAATGTAACATTAGGCTGCATTAATAGAAGCAGAGTATGTAGAAGGAGG
GAGGTGACAGTCCTATGCTAACTCTGCCTTGGCCAGACTATACCCACAG
GAGTCTGGGCATGCCAGTCTCAGGGAGACCCAGACAGACTGGCTGCATT
CAGAGGATGGTAAGTAATGAGAGTGGGGATTGGACTTCAAACTACCCAG
ACAAAGAATGGCTGAGCAAGCCAAGGATGCTGTGGCTGGGGCAGAGCAG
ACTGTGGGCTATGTAGTGGTGGATACCTAGCCTCTGCAGGGCTGTCATA
```

-continued

GGGAAAGGACATTGAGAAGAGGACTGAGGCTTGTTCCTGGTGGTCCTGG
CATGAACGGCCAGATGATCACATGGTCAGGTGGACACAGTCTCCAACAC
TGGGAGTAGCCAAACACTTACTGCCAACCTCCCGCCCTTCTCCTGACTA
GTTGCAGCATAGGCAATTGGGAGGAGCTTCCTGTCTCCATCTGAAAGCT
GGCTGGGTGGGCAGGGGAGGAGCGAGCCAAGTTTCAAGGCCGCAGTTT
CAGCACTCAGTCTGGGATCGGCTCAAGGAGCAAAGGGGAAGAACATAGC
CAGGAGGGAATAACATGAAGGCCCCCAGACCCAGAAAAGGCATGACTTG
CTCTGAGACCCTCAGCCGGTTGGTGTCAGGTTGTGACTCGGATCCAGGT
CTGACTCCCAGTCCAGTGCTTGAAGCCTCACCCCACACAGTGAGGGGAG
CCCGGCCATCTCTGCTCAACTGCTGCCATCTCTCTCCCCTTCTCAACCA
CCAAGGCAGCTCTGTCTGGGAGCACAAGCTCCAAGTCCACTTTCTGGTC
TGTGTCCCCCCAAGATGCCAGAGGACTTGCCTCTACAACACGGGCTGC
CCGTGCAGTGCCTGCTTTTCCAGCAAAGGGCTTCTGGGAACCCTTCTCT
GCACTCAGTGGGCTGGTGGGAGTGGGCGGGGTAGCGACCCAGTGCTT
GGGACTGTGCCCAGCTCTCAGGCCTGGCAGCAGTTCCTGGCCTTGGTTC
CTGCCAAGGCAGAGAGGACAAACACATGGCACCGGGAAGACTACACCAG
AAGCGATTCCACCAGACTGGGGTTTGCTTTTCTATCCCGCCCTTAGCCT
GCTTCCTGTCCTGGTCCCTGCCTCCCCCTCCACTGGAGCTGCCGTGTGG
GCAGTGAGGGGCTGTTTCTCAGCTGCCCTATGGAGCTGCCCTCTCCCTG
CCAAAGCATTGGCAAGGCGGCAAGGGGTGGGGGTGGGGATGGGGGGTGG
GATCTGCCTTCTCAAGCTCTCATTATACTGAGCACGTCTCACCCATTAT
TTTATGTCATCTAGCAACACCCCATGTGGACACTGAGGAGCATGGGGGT
CACATGACCACTGCCCAAGGCCACACCATCCGGATCTGCCTGAGATGGT
CAGGGTTGGCAGCCATTTCTGAAGGCAGTCCTTTCGCTTTGGCTCTTCT
TGTACCAGTCTCAGGACATCAGGGCAGAAGATCTACAGTCCCCAGCTTA
CTGATGTGACAGCAGAGGCTCAGAGAGGTTAAATGACTTGCCCAAGGTG
ACACGGCTAAGAAGTACAGTATCTCCTAACTGCAGACCAGGTGCTTCTG
CTGCTTCTGGGACAGATTCCTGCGTGGCTGGCTAGGTCTAAACGGTCC
TTAACTCCATCCCCACCGGTTGCTGCATTAGTTTCATCAAATAACACAG
TTGTACAGAGGTAGGGGTTCAGGGCAGGGCAGATGGAGGCTGGAGAG
TGTGACTAAGGAAACAGCAGGGGAAGTGCGGTAAAGTCCGAAGGGAGGG
ACGGAAAGAGAAAGCCAAGCCCAGGGGCGTGCCAGACAAAAGGAAAGGC
CACGCCGGGCAGGGCAGGCTTCAGCGGGTGCTGGGGCGTCTTCATCCC
GGGAAGCACACATTCCAGAGGACCCCGGAGTCTAATGGAAAAGCTGGCC
AGCCTATCACTATGGAAACTGCCAAGGCCACACAGCGCTACGCGTATTT
AAATGTGCTGGAGTGTTGAGATACTGTAGTGGTGGGATGCTTAAGTGCT
GGGGTGCTGGGTGTTGGGATGCCTAGGTGCTGGGGTGCCGAGATGCTGG
AGTACTAGTGTGCTGGGATGCTGAAGTGCTGGGGTCCTGAGATGCTGCA
GTGCTAGGGTGCTGAGATTCTGGGCTGCTGGAGTGTTGGGGTGCTGGGA
TGCTGGAGTGCTGAGATGCTTGGACAATGGGGTGCTGGAATACTATGGT

-continued

GCTGGGGTGCTGGGGTATTGAGATGCTAGGGTACTGGGATGCTGAAGTG
CTGAGATCCTGGAGTGCTGGGCTGCTGGGCCACAGGCTCTTGAATCCAT
TCGTCTGCCCAGGGGAAGAAACCAGAAGATAAAGAGCTAATGAAGGAGC
TTTGGTTGAGAGGGAGGAAGTAATGGAAGGAGCAACATCTTGTGGAGGA
GCAGGAGAGAATGGACCTCAGGTTGGGAGAGAGGGCCAGGCTACAGGCC
AGAGAGGCAGAAGGATTCCAGCAGAGTGTGGGCTCCAGGAGCCAAGGGG
AAACAGGTTTCTGGGAGGAGAGAGTCCAGTACTGCTGAAGTGGCAAGTC
CGCTGAGGACCAGGAAGCTTCATTTGGCTTTATGACCAGGAGGAATTTG
GAACTGTGACTAGAGTACTTAGGGGGAAGGAGGCAAGACTGGAGCCAGA
TTGCTCTGGGTTGAGGGGTGAGTGGGAGGTGAAGCAGGGCACTGTCACT
CCTTTGAAGGGTGGCAGAGAGCTGGAATTGGTGCTGGATGGGCTGTGGG
GTGACAGGGTCATGTGGAAAGCCCCTGGGGGCACCTGGAAAAGGAGAA
GCTGACAGTACAGTGAGAGGACAGCTAAGGGAAAGCGGAATGGCAGAAC
ACGCACTGCCAGGAGGAATGAGGATAGGGTCAGGAGTGCCAGGGGCAGT
GAGGCCAGCCTGGGGTCAGGTGGCAGGACGTGTCCAGGAAGCTGGTCTG
CACTGCAGCCCACACTGGCTCAGCCTTGAGGTTCCCTGTGTGGTTGGGG
TAGGAAGTTGAACCCTCTGGGAATGGAAGATGGAACCAGCTCTGCGAGC
CAAGCTCAGCTTTTATCTATGGGTCTCTGAGGGCTGGCAGAGCTGAGTG
GGGACAACTGTGATCCGTGAGGCTCTCAGGTTGAGGTGGCCCCTCCGGG
AGGGCTTCATTTTCCCAGCGGGTAGGTTCTAAGCAGCAGTGGCTGGGCA
GGTGGGTCCAACACAGAGCCAGAGAAGGGTGAATGGGCCTCCTGGCACC
CCACCCCTGCTGCCCCTGAGCTCAGTGATGGAGGGGGACAGCACAGCTG
AGCCCAAGTGCTTTGGTGTGGCCCTGAGGGAAAGCTGCAGCCTGCCTGG
GGCCTGGCATGGATGGGACACTTGAGGCAGAGGGACAATAGTGGGCGCT
GCAGTGAGGCTGGCTCTTGGAGAGGTTTCCTGAGGAGTGCTGCCTGAGA
CGGGCAGGGAGAACAGAGACAAAGTTGGTGACAGGGAATGAAAGCTGAC
TGAAGGACTTTACCCAGACCTATGAGGATATCTCTCTCAGCAGGAAGCA
GGAGGGACTGTGTGAGGACTGGCCAAGAGCTGGAGTGTTGGGAAAATG
ACTCTTTCTCCGACCCCTCTGTCCTAGCTCTGGCCCCTGGACTGCGGAG
GTCTGCTTCCACCCCCATTGGTCGATCGTTGTCCCTTGTCACAGCCATT
GAGAATTTTGGCAGGGAGCATGTTCTTAGAGCATTTTTAGGCTCTGCGG
GACATAACAGCTCTGCCTCAGAGCACATGCCTTTCTCAGCTCCTGAAAG
CCACTGATCAAATTGGAACATTTTGTACCTTAGGGATGAGGATATCAAC
TCTCCCAGCCACTTAGAGGGATAAATGTGATGATGCATTCAATTGTGAC
TACATCTGATCCCAACTGTTGCTTCAGCTGCTCTCCTATAGCACATGGC
GGGAGGCGTGCATCCCAGTAGCTACCTCCCCACTTTTGGGGAGATGTGG
TTCCATCCATGAAACCTGGGTACCCGCCTACCAGGTCCTGGCCTATCAG
GTGGCAGGGTCTGGTCAAAGAAGGGCATGTGTGGTCTTCAGCAAGGGAG
ACAGGACGGTGGTGCAGAGCGGGAGCCTTTCAAGAGAGCTTCAATGAAA
TCTACCTCATTGCAGTCAGGTGACGAAATCAGATCATTTAGTGGGGGTT

-continued

```
GGGGCTGGCGCAAAAAGTCGGCAGGTGGCAGCTCAGGGGGAATATCCGT
TCTGTCGAACGGACCTGGGAACTGGCTGGCAGCAACGGCAGAAGCAGCA
GCAGCGGTGGCAGCAGCAGCCACATAGCTTGGTGGCTCGATGCCCTGTA
TGGGGCTCAGGGGACTAAAGCTGGCCATACCCTGCTGGAGGAACTTGGT
GGTGTTTGCTACAGGCACCGGGCCCTGTACCGGGCTCTGCCTGAGGCTC
TGGCTGCCCAGCAGGCTGAAGCTGGGGTTGTTGGCCAGGGGCACTTGTG
TTCCCATCGCAGCGGGCACTTGTGCCTCCCAATCAGATGGCCTCTGAAG
GCAGGCCTGGCCAGAAGGTGAGTGCTGCTGAACGCTATTATCCACTTGG
CTGAGGGGTGTTTTCCCCGAAACTGCTGTGGTCACAGCTGCTGCCGCTG
TGACCCATGCAGCATTGTTGAACGCAGTGGGCATTCTTGGCACACTAGG
CCGTCTGAGCTGGTGGGGACTCAAGGACTGGGTGCCCAGGGAGCTGGGA
CAGAACCCAGGCAGGGGCACTTCTGGTGGGGTGGCCTTGGGGCTCTGCA
TATGCTGGCAGACAGAGTCAAGTCTGCCCAGGGGAGTCTGGCCTGAGTG
TGAGAGGATGGGACACTGGGGCTGGAGGTGAAAATTCCTTGCCGCTTC
CCCAGAGTTGGTGAGATCACTCCCATGCCCGGCGCGCGTCGACACGA
CAGGGACATACTGGGAATGCGCCCTTGCCGTGGAGGCGGGGACCCGGCA
GCGCTACGTATCCAGCATCAACCTGTATCCAGCATCAACCCGCCAAGTT
CACTAACTTGGTAGGGGTGAGGTTAGGGATCCTTAGGAGCCCAGGCAGC
CAGACTTTCTGGGGAGCCCATTCCCATTTGTGTTGCCAAAGTACCCCCA
GCAGGTTGTGGGAATGTTGCCTGTGAAGAGAGTCTGTTGGGGTGAGATC
TTGTGTGTGTGCACAGGGTGACAGTTGTGTCCCATTTCCCGGGAAGCTG
TGATGGCAGCAGAACCTAGAGGAGCCTGAGAGAGTGTGGGAGAGTGGGC
CTCTGGAAGAGTAGAGGCTGCGGACCAGGTGCAGGGCTGTCTGTCACC
CAAAGGAAGAGGGACTGATGACTCACTGAGCGTGTGTGTCCCCTGGTGG
CAGCAGGCCCCATAGTGAACATACCATACCTTTTCTGTCCTGAGCGATG
CTCCCAGCAGTCCTGGGAGATGGAACGGTCCTTATTCGGCTCACAGGAA
GGACCGCCTTAACTGGACAGACACAGCAAGGTGCTAAAGATGCCTTCCA
TCAGAGGCCAGGTTGGAAGCTCTAAAGAGACTTCTCTTGCTGTTCTCTC
ACCCACCCCCAGGTTGTGTGTGTCCCGCTGTGGATTCTCATGTCCTTTC
TGTGCCTGGTGGTCCTCTACTACATTGTGTGGTCCGTCTTGTTCTTGCG
CTCTATGGATGTGATTGCGGACAGCGCAGGACACACATAACCATGGCCC
TGAGCTGGATGACCATCGTCGTGCCCCTTCTTACATTTGAGGTAAGCGT
TCCACGGGAAGCCTCTTCAGCCCCTGAAGCTTGCGCTTCCCCTGACAGG
ATTCTGCACCCCTAGAAAGGCAGCCTCTGTCCCTCGAGCTCACAGTGAG
CCCACTCCAGGAGAGGGGAGAGAACACAGCCATCTCCGAGAGGGAGCTT
CGGTGAAAGGAGAGCATCCTTCCTTTCTCTTGGGGGCAGCACGTGGGC
TGGCAGGAGAAGAGTGCACCTTTTTAGCCATGGTGCCTCTGTATGGCT
CCAGTTTCCACTCTGGGGAAAGCAGAGTGGGATGTCAGATTTGTGTATT
GGAGTCACGTGGAGAATTCTAGAATGGGAGCTGTTGACTCCTTAGAACA
AACACCCGGAGGAGTTTGCCATAAAACTGCTGGCACTGGGAACTTTTCA
AGTGGATAGGCTATTGCCGAGCTCTGAAGAGGGACATAAAAGCTCATTT
CGAGCTTTCCCCAGGGATAGGTGGTTTCCTGCCTTTTTCTGGCGGTGCT
GATGTTCCCTCTTGTGGGAGCTCACGCGGGGGTGGGGTGGTGGGGAGGA
ACTGCCTAATGAAGTCTGGCTTCCGCCTCTGCCCATTTTCGGTGCTGGC
ATCAACCGGGACTATGTCTCTTTCTTTAGATTCTGCTGGTTCACAAACT
GGATGGCCACAACGCCTTCTCCTGCATCCCGATCTTTGTCCCCCTTTGG
CTCTCGTTGATCACGCTGATGGCAACCACATTTGGACAGAAGGGAGGAA
ACCACTGTATGTACTCAGCATTTCAGAAGTCCTTGGTGTGTGTCTGGGG
GGGGACCAGGGGGTGGGGGGTGGCGGATAGAAGTCTAGGAAGGGATGAG
TCCCCGAGGGCCCCAATTTAGAAGCTTGTGTGGGAAAGTGAGGGCTGAG
GAAATTCTGGGACCTTCTAAGGGAAGGGCATGCCGTAACTCTGGTGTTC
TGCTGGCCTGCACCGGGACTTTTCTCGCAGTGCACGCTGCCATTTGAGG
TAGAACCAGACACGGCAGGCAACCTCTCAGAGATCCCGTTCCCTCCTCT
GCAAAATGGGGATCAAGACAGATTCTTCCCAGGCCCGGGAGGGTTTGAT
GGAAAATCCACATCTCCCACCCAAACCTGGGATTCATCCTAGGTCCCTG
TTGGCCGCTCTGCCTCCCCCATATCCTTGCTGCCATCACCCGAGTCTTG
CCTGTCTTGCCTTGCTAACACTCTATTCCCCTCCACCTGCTTGCTGAGG
CAGACACTTCCAAAACGATCTCTGCAGAGGGTGCCTTCCTGGCAAGGCT
GTGGGCTCCATGGCACGGAAGCCCAGAGCATTGCCCTTCGGAAAGCCAG
TGGGTTTGGGGGCAGGGCCTCACTGCAGCCCAGCAGCCCGGGCTGTGCT
TGCTGTTTGTGCCTCTGCCCCCTACCCCGCACCCGGGAGCAGGGAGGGC
TTGCACCGAGCTGACACTCCAGTAGCCTACAGAGAGGAGTAGTGGGACT
GGGAAAGTGGCTTTAAGGTGGCTCCATGAGTTCAGGCCCCCTCCTGGCC
AACCCGTGCATGACTACCGCCCTCACGGATTCCAGAGGGTGACAGAAAT
CTTGTTCTTGGGTGGCACTGTCATCCATGAGTTTATCCTGGCTGGAGAA
GATTAGCGGAAGACACCGTAGTCTGCGCACCACAGATATTTTGAGACTC
ACTGGAGCAGTAGTTCTCAAATTTGGGCATCCAGCAGAATCCCAAAAGG
GCCAGGAAAAGGGGACCGCTGGAGCCCACCCTAGCCCGACTCAGTTTCT
GGAGGTCTGGGCTGGGGCCCGAGAATGGCATCCCTAACTAGGCCCCGTG
GACGCTGTCCCTGCCGGTCCGGGAACCCCACTCCAAGCACCACAGAGCT
AGCATTTGCACTTCTTCCCCATTTTGGGTACTCAAGCCCTGTTCAGGCT
TTGTGACTCAGGAGTCTGGATAAAGTATGTTATGACATTGTAGGAGTGA
AACTTCTTGTTACGGAAAGAAAGTTAACAGGAAGGTCAGTTGAGCCTCG
TGTGTGAAATAAAAAATTCTTATTTTTCAGGGTGGTTTGGTATCCGCAA
AGATTTCTGTCAGTTTCTGCTTGAAATCTTCCCATTTCTACGAGAATAT
GGAAACATTTCCTATGATCTCCATCACGAAGATAATGAAGAAACCGAAG
AGACCCAGTTCCGGAGCCCCTAAAATCGCACCCATGTTTCGAAAGAA
GGCCAGGGTGGTCATTACCCAGAGCCCTGGGAAGTATGTGCTCCCACCT
CCCAAATTAAATATCGAAATGCCAGATTAGATGCCACTTCCGGGGACAG
AGCTTAAGTGGACTGGGACGCACTCTCTCCGCCTTCCTCTGCCCCCTCG
```

-continued

TTCACCCCGCAGACCAGAACCAGTACTGGAGCTGGGTCTCCAGGTACGT
CCATCTCATGCCTTGTTTGCATCCAGCGCCTATCAGCCACTCACCACGA
CGGGACGCGGAAGTGGCAGGTGACGGGGGTGTGTGCCAGCAGATGCGGA
TGCCAGGAAGAGTGTGAGAACAGGGGTGGGATTACCGTCTGTCTGGGAG
GGGCTCCAGGTACCCCTCTTCCCCGTCAGACCCACTGGGAGATGGCTGC
TTGCCAGGCCCCCAGAAGGAACATCTGTCTATACGGTGCTGAAATCCCA
ATCAAAAGTATTGTTTAGAAATGTATTTCTCCACAGGGCTGACCTCCTG
CAGCTCGCTGAGCACTCCCAGGTCCTCAGCACTCCCAGGTCGTGGCTGG
GGCAGTCAGTAGGAACTGTAACTATGTCTCTGATGCACCACGTGTTTAG
ACACAGCACAGTCCTTTTTTCTGTTCCTACTGTGAAGTAGTTTCTCTT
TGGGCATGCTGACAGCAGTTTTTCATAGCCTCACGGATGAGCCCTTTCT
ACGGGAGTGACTCCATGCTTGTATACAGAGTATTTATACAAATGTTTTA
GCATCTTCATATGCGGTGTTAACCCCTAGTTCTGTACAGCATATTCTGT
TCAAGTATTTTTTTACAAGCTTGTGCTGTAGGCACATGCCTTCTGCTGC
AGAAGTGGACGCCCGTGGCACACTCCCCCCCCCCCCGTGGGGTGCCA
CGCCTTCATGGGACATTGCCACTTCTGCCCTGGAACTCGTGCAGGTACG
TAGTAGCTGCTACTGCCACAACGGCAACACCAAGCAAGAGATGGTCCAT
GCTTTTCTGACGTTCTCAGAATAGTGGCTAGCTTCAAACCTGACAAGCG
CTGCTTGAAGCCGGAACACTAGAGAATGTTGCTGAGAGCAGAAACGGCC
ACGCGGGTCACGACTATGCGTGGGAAAGTCTCAAGCTTCCCTCCTGCCA
GCAACAAGAAGGCTTTGGAGTAGGCATGATGTTTTCACGTGTGCGTGCC
GTTTCTCCAAGCACTGCAGGTTCCACCGTGTGTCAGAGGCTGCAAGTTT
AACATCCTCCTGCCTGAAAACAAATAGGTCCTTTGCTGAAAAGAGGGTA
AAAAAAGAGCTTTGATCTTCTCAGCCAGGAGAAGAGGGTGGTGTTTTCA
CGCGGGCAACTGCTCGCCGGCCTACATGGGGTTAATTCAAGTCTGCTGC
GAGCACGACTCCGCCCTTGGCACTGGCCTCCAGCAAGCCCTGTTCTCTT
TGGGGTACAGGGGAACGGGATGGTTTAGACTTTCCTGCTCAGTGTGTAA
AAAATGTAGCTAAAGCCACTATTTTTGCTCTCCTTAAGCTGTTCAATAA
ACCGGTTCCTCATTTTACACGTGCATGATGTGTATCTTCTTTGCTGGAT
GGGCCAGGAAACTGGAGTGGTCCTCTCAGCCAGCCTCAGAGGAAAGAAA
TCTCTAGCTGGCACAGGCAGCCAGTGAGTGAGGCTGGCGGCTGCAGGGG
CACAGCCTTTAGAATGAGTCCTTCAGTGCACAGGTCCCAGGGTATACGG
GGTAGTGGGAGGAAGGAGGGGACGCCTCGCAGATGCCACTGTTGGCTGG
GCTACACCTTGCCACACTTGTTACTGCTTAGGAGGCTTTCTGGAGTGTT
CCTTGGGTGCTACGACAATCTGCAGCAGACACTGTCCTTTCACCGCTCC
TGGTCCTCGTTTGCTCCCCAGTGATGTCAACAGCTGAGGACTGCTCACG
CTGCAACAAAAGGCTCTGCAGTCGCTGTCTAGCTTGCCCTAGTCGTCTC
TAGAGTTCTGCCTGAACTGAAACTCAAGTGGGGTTCAGCTCATGACTTG
TGGCAATTGACCAGGAAATTCACCAGTTGCTGTGGCTGGAAGGATTTTC
AGTCCTGTGGGTTGTAACCAGAGGCCACAGGTGGATTCTGCCTTAGGCT

-continued

CATGAGATTTCCGACTTGCTGTTGAAGAAAATGCCTTGTGAAGTGACAA
CAGTAGCTCTGACCCAACTGCCGGTGCCTCGCTAGTTCCTATACGTCCC
ACTGGATCCTCACAGCCCCGGGAAGCAGGTGCTACTACTCTTATCCCCG
GGAGGAGACAGAGGCCGAGAGAGGTTAAGTGACGTGCCCAAGTCACACA
GCTCGGCAGCGGCCGGGTTGAGCATCAGCAGTCTGTTTGCAGACCCCTC
ACTGTCACCCCCTGAGCCAGTGCGCCTTGGGCCCTGCGGTCAGGATGTC
TCAAGCGTGGAGGCATCACCGGTTCGTGGCAGTCTCTGGAAGGTCACTG
AGCTCTGTGCCCAGAATCGAGTCGGGGGAGTCTGTGCAGAGGTGGCCCT
GTGTGTGGGGACAGTGTGTGACACAGACACTGCTTTGGATGGACACCTC
TCCCGTGACCTCCTAGCATCCAATCCCAAAGGAACAACTGTTGCAGAGA
TGGACCGCTGGACACAAACCCACGTGCGTTTCTCTGGAGACACTGGCCA
AGGAAAACAAAACATGCTCGAAGGCCAACAGCTGCATGCCCCACCGCGA
TGTGACCGCAGACACCCGGGGTGTAGAAGGGTCTCTGCCTGGTGGGGGG
ACACGTGCAGGCCGAGGAGAGGCAGGAAGGAGGCTGCCTCCGACTCCCC
ACTGGACTGCATGGCGACGGCGTGTGGTGGGGCAGTCAGCTAAGCCATT
TGCCTAAGGGGCTGTCGGGCATCTGCGTGCTGGGGACCGACAGTGTGGG
TGTGTTAGGAGGATCTGTATGGAGCACATTGCTGCCTCTGGCTAGGACA
GGGTGGAAAGGGTGGCGTGGCTACAGCCTGACCCATGGGCACCGTCCTA
CCCTTTGTTCTGTGCTTCCGAGTGTCAGTCATGTGCTGGGGTCTGTGGG
CCCATGACTCAGACGGTGAGCTCTGACCTTCCTGAGCCAGGGCTTTGCT
GTAGTTGTGCCTGGCTCAGGAGCTCTAGGACAAGGGGACCGCTCCAGGT
CTGCATCTACGGTGTGGCAGGGCCCCTCGGCACTCTTGTGCACTAGTGT
CATCTTTCCCATTGAAATGACTGTGAGGACCAGAATGTGCACATGCAGA
TGGGCAGCTACTTGTCTGCCTTGGCCCTTTATTACACAACTTGCTGGGG
GTGGAGATGCCACCCCCCGGCAGTCAGAGCCCCTTTATGATGTCATGGG
GCTGGTTACATGACTGCCAAGGGGTGCTGCTGGCCACACTGCACTAGCA
AGTTTGCCAGATGGAGGACAAGCGATCATTGAGTATGGCTCGCTGTGAA
GAAAGAAATTCGAGAGGACAGGATCATGGCTTGGAAAGGGTGCCTTTCC
CTCCCCAGTTGCAGTCAGAGACCTACCTTCACCCAGCAGATCCTTCCCC
TGCCTGGGACGACCCGGGGTCCACTGGGAGCCCTAACTTGAGGCTGCTG
ACAGAAGAAATCGCTTTCCAACCTCTGGCCGAGGAAGCTTCGTTCAGAA
GGCCGCACCCTGACGGTGACGTCCCGCCCCAGGGAGAAGATAATCTCCT
CTCCCTCCCCTTTCCACAGAAACTGTGGAGACTGGTCAGCAGCAACCAG
TTTTCGTCCATCTGGTGGGATGACAGTGGGGCTTGTAGAGTGATCAATC
AAAAACTCTTTGAAAAGGAGATTCTCAAAAGGGACGTCGCACACAAAGT
GTTTGCCACAACTTCGATAAAGAGCTTCTTCCGCCAGCTAAACTTGTAT
GGCTTCCGAAAACGGCGTCAATGCACTTCAGGACCTTCACCCGCATTTT
CTCCGCAAAAGGCTGGTCTCCATCTTGAATAAGGTAATGAACGACAAG
CCTCTGGAGGGGTTAAGTCGGTGGGCTCTGGGGCCTGGTCGGGTGGAAG
TCCCAGGACTGCCTCCTGGGAAGTGGGCGACCTCAGGCAGGGTGTGGGG

-continued

```
CCATCGCTGTGGGCCTGTGTCCCCCTCTGGGTGGAGGTGACATGAACTA
AGAGTGAATGTGGGGAGAGGGCTGAGGATGGTGCGGGCCCCTCTCGAGT
GTGTAAAATATCACAGGTGCCAAGTAGCCGTATCTGCGTGTCGTCCTCC
CCGGGGCCAGCCATGTCATCTGGTGGTTGCTGTGTCCCCCTGACTCCAC
AGCACATTACCCTGTGAGGTGAGCAGGCCAGGGGAGTCTGGTATTTGTA
CCACTGTCACCCTAGCTGGTGTCTGGAGAGGTGCTCAAGTGGAAGCACT
GAAGGGCGCCTGGCGCAGGAGGTGCAGATGCTCCTGCTGCCCTTGGTAG
GTGGGCCCCTGGTGTGGAAGAGCCAGTACCCAGGGCCTCCAACCCAGCC
GGGGTGCATTCTGTTGCCAGCTGACACTGCATGGGGAGGCCCAGAATC
TTCTTCCCTCCTGGTCTGCAACTTCAAAGACCCTTTCCGCCGGCCATGG
ACACCCTAATCTGCCATTTTGAGGCTTTTTCCAAGACGGAAAGGCCCGC
CACAACTTGGTAAACCTTGACGATGTGAACGCGAGTCCCCAGCTTCCTT
TGGGGACTGGGACCTTTTCCAGAAAGGCCTCCTGGGCCAGTAGAGTTCT
CTTGCACAGGGGCGTAGATGGTTGGTAGTTGTAGTCCATCCTTGTGACT
TGCAGTTTCCTTTTGTTTATTTAAACTTTGACTTATAGTTAGAGTTCTA
CTGCCATCCTTACTTTCAAAGAGACTCCCCTCACCTCCTCGTGAGGATG
AAGAGAAGAGTGGGTGTCAAGTCTGCACCAAGACATCAGGAGGAGGACA
AGCCAGAAGCTGCTGGATCCTGTCTGGCACCAGCAGACACTGAGCAACA
AGATCACACGTCTCCGAATGAGAATGACCAGGTCACACCGCAACACCGG
GAACCGGCCGGTCCCAACACCCAAATCAGGAGTGGCTCTGCTCCACCAG
CAACTCCTGTGATGGTGCCTGATTCCGCCGTGGCGAGTGACAACAGTCC
AGTGACCCAGCCGGCCGGCGAGTGGTCAGAGGGCAGCCAGGCTCACGTC
ACTCCGGTGGCCGCTGTCCCTGGGCCTGCAGCGCTGCCCTTCCTCTATG
TCCCTGGATCTCCCACTCAGATGAATTCTTACGGGCCTGTGGTGGCCCT
TCCCACAGCGTCCCGTAGTACCCTTGCCATGGACACCACAGGACTTCCT
GCACCTGGCATGCTGCCCTTTTGCCATCTCTGGGTACCGGTGACCCTAG
TGGCTGCTGGGGCTGCACAGCCTGCTGCCTCCATGGTCATGTTCCCCCA
TCTCCCAGCTCTGCACCACCATTGCCCCCACAGCCACCGCACGTCACAG
TACATGCCAGCTAGCGATGGGCCCCAGGCGTACCCAGACTACGCAGACC
AGAGCACATAGAGGGCAGCATTTGGGCAGAATATGTGCTGGTCAATAAA
TGTGTCAGAAAATGAGTAATTTCTGACTGCACAAAAAAGTCTTCATGGT
CTCCATCCTTTTTCTTTCTTTGCAGTCCAGTACCCCCCTCCGACATCTT
TGGCTTGCATGATAGAGACTTCAGCCTAACACGCCTCCCTGGAAAAGTG
CCCAGGAGATACTCGAGCAGGTGCTGGGTTTTAGGAAGCCCCTCAGACA
TCCCGCCTCTACTCATTAAAAATTACCTGGAGCTGGCCGGGCGCAGTGG
CTCATGCCTGTAATCCCAGCACTTTGGGAGGCCGAGGCGGGTGGATCAC
GAGCTCGGCAGATCGAGACTGTCCTGGCTAACACGGTGAAACCCCGTCT
GTACTAAAAATACAAAAAATTAGCCGGGCGTGGTGGCGGGCACCTGTAG
TCCCAGCTACTCGGGAGGCTGAGGCAGGAGAATGGCATGAACCCGGGAG
GCGGACGTGCAGCAAGCCGAGATCGCGCCACTGCACTCCAGCCTGGGCG
```

-continued

```
ACAGAGCAGGACTCCGTCTAAAAAAAAAAAAAAAAAAAAAAAATTACCT
GGAGTTGCTCGCTGAGTGCTAATTGTGCTGCTAGCATTGCCGGCCTAGG
GTTCACAATGACTCTGTGTTACTGGCCATTCCTTGTCATGGCGGTGCCT
TTATATAACAGGATCTTCACTTTACATACAGATGAGATCACGTCTGGCT
TTGTCATTGGGTTAAAAAGTGCCCTTGATAGTTGTGGAGGTGACACATA
CTACCGTCGACTCGAATAGATCTGCTAGGCGCCAAGCTTGTCAGCCTTA
CCAGTAAAAAGAAAACCTATTAAAAAAACACCACTCGACACGGCACCA
GCTCAATCAGTCACAGTGTAAAAAAGGGCCAAGTGCAGAGCGAGTATAT
ATAGGACTAAAAAATGACGTAACGGTTAAAGTCCACAAAAAACACCCAG
AAAACCGCACGCGAACCTACGCCCAGAAACGAAAGCCAAAAAACCCACA
ACTTCCTCAAATCGTCACTTCCGTTTTCCCACGTTACGTAACTTCCCAT
TTTAAGAAAACTACAATTCCCAACACATACAAGTTACTCCGCCCTAAAA
CCTACGTCACCCGCCCCGTTCCCACGCCCCGCGCCACGTCACAAACTCC
ACCCCCTCATTATCATATTGGCTTCAATCCAAAATAAGGTATATTATTG
ATGATGTTT

SEQ. ID. NO. 17
Helper dependent vector C4AFO
The sequence is shown without transgenes.
AAACATCATCAATAATATACCTTATTTTGGATTGAAGCCAATATGATAA
TGAGGGGTGGAGTTTGTGACGTGGCGCGGGGCGTGGGAACGGGGCGGG
TGACGTAGTAGTGTGGCGGAAGTGTGATGTTGCAAGTGTGGCGGAACAC
ATGTAAGCGACGGATGTGGCAAAAGTGACGTTTTTGGTGTGCGCCGGTG
TACACAGGAAGTGACAATTTTCGCGCGGTTTTAGGCGGATGTTGTAGTA
AATTTGGGCGTAACCGAGTAAGATTTGGCCATTTTCGCGGGAAAACTGA
ATAAGAGGAAGTGAAATCTGAATAATTTTGTGTTACTCATAGCGCGTAA
TATTTGTCTAGGGCCGCGGGGACTTTGACCGTTTACGTGGAGACTCGCC
CAGGTGTTTTTCTCAGGTGTTTTCCGCGTTCCGGGTCAAAGTTGGCGTT
TTGATTCGGCCGCTTGGGTCATAGACTTCTTGAGAACCAGTTATAAGCT
ATGGTTTCTCTCCACAGAAAAAGCACTTATGGTGTCTCCCCCTTTCCAG
CCCACCAACATTTTACATCTAATTTGGGGGGTTTTCTGGACCACTTAA
TACCCATCCATGGATCTCATGTGAAGACTCCCCTGGCTTGAGAAATCAC
TGTCTTGTTGAAAATGGGAACAAAGCTAAGTCAGATAGCTGGTTCATCA
GCAATGACTTTGACCAAGCCTGATCCCACCCTACCCCACCCCACCCCAG
TGACCACCCCCACAATGGAGCACACAACTCTAAACTGGTTTGTAGGTA
TGTGTGTGTGAACACGCTGAGGAATCTGCAAAACCAAATGGTGAGTGCA
AAACCAAACAGTCACGAGTAAATCTCACAACAACCACGTCCTGAGCTGC
AGCCCTTGTTGAACTATACCCCACTAGGGCCCCAAGATTTTAGGACTTG
TGTGTGGGTGGGACCTCCCCTTTCTATCATGCTTTAGAAGACAGGGATT
TCACCAGAATTGAACATATTGAACATATGACCCATTTTTTTCAGCCAAA
GGCAATTAAAATAACTTCATACTTGATATCCATGTCAGCAAAAGCTGCA
AAACGCAAATGGGTGGCTGCTAAGAGCCCTGGTACCCTGACGAGCACAC
CAAGTGCTTAGCAACAGTGGTGTCCAAAGGACCAGCTGGAAGCCTGCCT
```

```
TGATGAGAAGTTGCTCTTCTTTCTACATGAAGGAACACCTCTACTCTCC
TGCTTTAATACCTGAGCTGTGAGTGATCATCTATGTCCATTAGCAAACA
TCCCAGTGGAGAAGGAAACACTCATACCCGAAATCTAAGCTACATAGTT
GGAATCACTTCAACTTATTGCAATAAACACTTACTAAGCACCTATTGTG
GGCAAGTCTTTGCAATGGATAATAGTTCAGTAGATATTTTGATGTAATA
TTTGAAATAACAATAAAAATTGCCACCACTGAATTTATTGAGCATTTGC
TGTGCTTTAGGCACTAACCCAGGTTCTTTAAATATTTGGTCTTATTCGA
TCTGTATAAATAGCCATCTATGAGAAAGGGACTATTATTGCCCTTATTT
TACAAATGAGGCCAATGAGGCCCAGAGAGGTTAACTAAGTTGCCCAAAA
TCATACAGCCCACTAGTGGCAGAGCAGGATGCAAACCCAGGCTTGCCTC
GTTCCCAAGCCCACATGTCGTTTGCATTGGTGTGGAGGTGTGCATGTGT
TTAGTCATTAGCATGTTATATGATAAGCAAGTTTTGAAACATAGAAACT
TAAAATGTGCCATTAAGAAAAGTACAGGCAAGGTTTTCCAAGGGGAGGT
GTGGACCTCCGGACAAATTTTTAAGAACTAATTATAAATACTTAAAAAT
GGGAATAAGAAGACAACCTAACTACCTGAACAGTTTTAGAGATGACTCA
TGCCCACCCTCTAAAACCCAAACAAAAACAACAAAGTCAAGAAAACCCA
TGAAATCTTAGCAAGCGATTTCTATGTACTTGTGAAAAGGATTTCTTTA
CCATTCTAATGGGATTTATGCCAACCATAGAGGGCTCAGTGCCCCTCCC
ATGGGGTGGTTAGTGAGTACAGAGCTGAGCTCACCGGCCATCTGCAGCT
TCATGTTATCAAGCTCCAGTTTGTCCTTGGAGCAAGGTTATCTGGGACA
TGAGCAGAGGCATTGCTTTCTGCAATGGACAGTTCTTTCTGCCTGCATA
CCTAGCTCCTTGATAACTTTAAATACCATTTTATAGCCACACTGGAGTT
TTGAAGACCTCAATATGCAAATATTACTCAGGTTCTGATTACTTGTCTG
CTCCATGATAACACACTCTAAAAGCAATGAATGGGGCTTATTTGTAGAG
AACTGAAGCATTTTAAGCTTTTGCTCAGGAATCCCTGGTAGCTTCCTGT
GACTTGCAAGATATTAGTGATGGGTCAAGAAACAGGACCCCCCATCAGC
ATAACATACGCAGTGCCTCAGTAGTCCATCAGGCAGAAAAAACTGCAGA
TGGCACATGGAAATGACCAGCGGCGGAAGATACCCCGACAGTGTGGGCA
GTTCTATTTCAGCAGCAATCAAGAGGGGGCCTGGAGCCACTCAATCAAG
TGGAGCAGGATGGGAGCAAGCACTGTGCAGACCAATGCAATCCCCAGTT
AACACAAAAAATAAATAAAAGAGATGAGATTCAGTCTCTTGACTGTGAC
TGACTGGGAGCTTTATAGCTGATGCTTGTGTCTTTTCTCCATTTTATTT
AATTAGGAAAAGAAATGCTTATCACACACTCTACGTGTGAGGTACAACC
TCCACAGGAAAGGTTGTTAGGAACATTTCAACTTCTAGAAGTTTCTAAA
CATAAGGTAAATCCATCTTTGTCCTTGGGATCACTGCACATCTCAGAAA
GGCAAATAAATCAGTAATTGGTGGGCATAATTACTAGCTCATGGACTGA
CAAGGTCTACACTATTTCGAATCTCACAGAAGTAAGCCATGGGACAGAT
AGAGTCTGATAGTGGTGCCCCGTTTCCTGGAGGTCACACTTACTCATCC
CCCTGGACCCTGGGCTTCTCATGATTGTCAGAGAGTTTGCTGGAACCAG
GTCAGCCCAGTTTCCCTTCCCCTGAAAAATCCTCCAATGGCTCGCACCA

AGACTAGAGATGCAAGTGCAAGCACATCCACCCTCTCAGCAGCCAGGTT
TTGCGTTCCATAATGTCACGTACCCCCAGTCATACCAATCTCCTTGGAG
CTCTCCAGACAGGCTGCCATGTGTGGTCGGCCCTCTGTGCTTGTGCTCC
TTGGTTTGCCAAGCCTGGAATGCCCTTTCTCCATGATTGTACTCTGGGA
ATTCTGTGTGTCTTTCGAGATGAAGCTCCTCCACCCTGGAAATTCTGCC
TCTCTTTCCAGGTCCAGCTCCTGTGGCTAATACCCTTGGCTGACTGAA
CATTCTTGCTGGGCCAAGTCTTAATCATCTCTAAATCCCTCTGGTGCCC
CGACAGTATCTAGCCCAGGCAAAGGGCTCAGCAAATACTTGCAAAATTC
AATAAACTTTACTATGTTACTAGCTTGGCATGATGTTCTAGGCACTTGG
GAGATTATAATCTGGTGAGCATTGTGCTAGTCTTTTTTTTGGGATAAAC
ACCAATGATAAACTGAGCCTTTACTCTCATTTTAGCACATCTACTCATC
TCTTTTCAATGCTGGTGGGTTTATAAAACCCATCAGTAGAACAGAGAGT
GATCATAATCATATGGTGAAAATAACATCAGCTAACATATTTACTGAAC
ATGCTTTAGTGTGCTGGGCACTGAACTCTGTGCACATGTGAATTTGAGA
TAGATTGTTCCTAGCTAATAAGATGAGGAAGTGGAGATGGGCTTACTCA
AGTCACACAATAGCAAGATGGGGTACAGACAGAAACCAAGCTAGAAACC
AAGCAACCCCTGGGTTTGGAAATGCATGGGCTCCTCCTCTGCACATGGC
GAGGAGCAGTCAGGTGCTCCTCCTTCTCTCATACTGAAATAACTCTGCA
CTTTTGGCTATTCTGTGACACTCTGTGCTATTCTGTAGCTCAAATGGCT
CTGGTGCAAGGAGCTCAGATTATGACTAACCCCCATAGATATTCAGCTG
CTTTGCAAGAAGTGGATGAATGCTCTGGCTTTATAAATTATTGACTAGA
TTGGATATTGGCCCAATCTCCACTCTGGTGATTCGGAAGGAGGCATATG
CACTTTGCAAGGTTATAGTAGTGCACTCTAATTCCACTGGCTTCTGAGA
GCTTGTAGGTTTCTTGACTTAATCATTCTGGAATTAAGGTAATGGATCC
TCAACACCTTTTCTTTCCCTGGCCTTTACTAACCATGTAACAGAAATGA
GCAGAGAAACCCAAGAAAGCGAACTGGAGACTTGATGAGTGTGTCAAA
GATGCTCAGAGTCCAAGGTCCTCTGTGGCTCACTGACTTCAGAAGCCAA
CCTCCGTTGTTCAAGTCACTTGTGAGGTTACTATGCTAGAGCACTAAAT
ATTATCCAGATAGCCCAAAGAGGTGAAGGCAGACATGTGGAAGAACCTG
GATTTTTGGGCAAGTTGATGAATGCCTCCTGCCCCATATCAAAGAGAGG
TGATAGGAGACAACTTTGTGAATTTGAAATAATGCACCGGGGAAACAGG
AAAACGTAATGTAAGTCACGCTTCTTGGCTTTTTTCTTGCCATTACCCT
ACTTGGCCAAGTGCAAATGGGATTTCAATATATCATAAGTATGCATCTA
TTAATAACAATGCAAGAAAGCTGTACAACTGAAGTCTGAGATTTTGTAA
GAAACAGAATCTCTGTAAGCATCACCATCCAACAGAACTTCCTGAGTTG
ATGCTGAATCATCCCAGAAAGAAGGCGCGCCAGCTCTGCAGGATCTTCA
AGTCTGGGGTGCCACCAGCAAGCGACGGTCCTCCATGGGCTCTTCACCT
TACGGCAGTGTCCAGAGGCACCGCCAGTCCTCTGCTCCTATGCTGGTCC
TGCTGTCCCTGGCAAAAGGAGCCAGAGCATTCTCTCCAGGCCTCCCGAG
GAGGCTGCTTCCTTTGTTTTGCAGATGGAGGCTCCCATCCTTTGTTCTG
```

```
AATCAATGTGCTCCAAAGATAAGCCCCAAGAAAACAGTTGTTGCCTTTT
GACACTGACAATTAGAATCGTTGGAAAATGGAGAAAACAGGAAATGGCA
AATGGTTTCAGTGACCAGGAGGAAACCGTGCCTGAAAGTTGCTGCTTAG
TGACTGGGACACTCGCTTTCTGCTCTCTTATGAAGGACAGCCTAGGCCG
TGTGGCCTTTTATAAACAAAGCTATGAAGGGGTCGTCAAATTTTCTAGG
GCTGCAACTGTGGCACTACGTCCTGTTGTGCCAGGTGACACTGACAAGC
AGCACTGAGTTCTATGCAAGCCCAGGTGTGCTTCTCTCATGGTGACCCC
CAGAGAACTAAGGCCCAGCTCTTCCTCTGTCACACCCCTCCCAGCCCCC
ACTGTCAGACAAGGGACCACATTCACAGACAGTCTCAGCCAAGATGGCA
ACCTTGGAAGTCCTGGGGATGCCTTTCTAGAAGCTTTAGGCTGACGCCA
GGGAGCTGTAAAGCCCCCACCTGTCCCTGGGGGTTGTGTGCTGGGCAGG
AGAGAGGGGAAAGAGCCCAAACTCCACCACTGCCTGCTGGCACAACTGA
GCCCACGCCAGGCACTGCACCAGCTTCACTCACCAGCTACCACATGCTA
ATGTCTCCTGTTTACCCAGGTGCAATCACCTGAGTGCTGCTTTCTCACC
ACTGCATGGGAAGAACGATCTCATTACCAATTCAACCACTTAAGCAGGC
AAAAGGACTCCAACGGGGGAAAGGCAGAGGACAAACGATTCGGGGACTG
AGACAGATGCCCACAAAATGTTCCTGGATTTTAGCCGGATTCGGGCTGA
AGTTCCTTGCCCTATGAGCCCTTGGAGGAGAGCATCCTGACTCAGACAA
GAATTCAAATGACAAGACTTCTGGGGGATGGCAGTGAATGGATCCAAAG
CCTTGTTTTATAAAGAATGTGGAGGAAGGGAGGAAGGAAGGGAGGGAAG
GGGAGACTGAGAGGGAGAGAGAATAAAGAAGAGGAAGAGAAGGAAGAGG
AGGAGGAGGAAGGGGAGGGGAGAGGAAAAAGGGGAGGGTAGAGGAGGAG
GGAGAAGGGGAAGGGAGGACAGAAGAGGGGAGGGAGCGGGGAGATTATC
TACCCCTCCATGCTAGGGAACTCCTGTCTCCTTTTCCAGCAGACACTGC
TCCATGAGTGCCCCCACAGAGAGCCAGCCTGCCACACAGCAGAAGGTGC
TCAGCTATCTGTCCCAAAGGTTGAGCACTAGTGTATACCACAAGGAAAA
AAACCTTCTTTTGTACTGTTTGGAAGCCAGAATTAGAAACAACTCGTTC
ACCCTTCTGACTTTCCCTTTGCAATGACAGGAAGATAGTATACTGCATG
GGACCACCACACATTCAAGATCTGAGTTGTGGGGACCCCCACCCCCACA
TGGGTGGAGCCCCCTGAGACCCGTGGGCTCTGACTGGCCATGGCCCATA
GATAGTGACAACATACACACTGCTATCTGAAGCCTAGTTGGAGGACGGA
TGGATGCTTTTAGGAAAAAATTCCCTTTAGTCGTCCCTCAGAAACTACA
ACGGCTTCCTAAAATGAATGGCAGGCAAGTTTTGATTGTTTCCTAAGTT
CCCCCTAACTCTCAGAGCCTGTGACTCAGCTTCTCCAGAATGCCTGCAG
GGAGGCAGGACCACTGGGAGTAATGAGCACGAATTGGGCCACTTCTCCC
AGTGGACTGTTAACGCCGAGATCTGGGTGGAACCCACTGAACACCTGC
CCTTTTGCGTTGCCCAGAATGCAGCCAGAGGGATACGGGCCACAGTAAC
TCTGGGCCCCTGAACCTACCTTCCCAAGACCCTGACGGGAAGGTATTG
CTTACATGACAGTCCAGTCAGTCCCTCTGTCACTCAGTTAACAAACATG
GTCATGGGTCTACTATGGGCCAGGCTCTGTTCCGGGCATGGGGATAACA
CCGTGTGTCTCTACTCTTATGGACACAAGTAAATCAATCAAAGCAGATA
ATGTTCTAATGACCACCCAGTAGGGTGAAGGGATGGAGGGTGGGCAGGT
GCTGGCAGAAACCTAAGGTCAAGTCATGGGACCCCAATGGGGAACTGGA
AACTGCCACACCATTTTCTATGTTAGGGGTCTTTCCTTGCCCTTCTAGA
GACCTCACCCATGGTAATGATGCTGCCCTCAGGTTTGAACTGGTCTGAA
GCTGTCACTGGGGCTTCACAAAATGAATGCCACTGAAAGCAAACGGCA
GAGATCTGTATATGAAATTCTTTTTACCCTTTGTTTTCTGTCTTCCCAC
ATGATCTATGACTGCTGCAAACTCTATTCTGACTCCTCCTCAGTCTTGG
CCGGTCTGGGAAGAACTTGGTTTAGATGCTGGGAATGATCCCGGGCAAA
GGAAACAAATATATTTCCAGCTTGCTTTTCTTCTTCCCCTGTGGTGCCT
GCATCCTCTGTCTCGCACTGACTCACAGGCTGGACTGACAAAGTGGCTG
TGTTGACAGGGAGGATTTAGTGGATGCCAGGCCTGACCCTCAAAGGCCC
TCAGGTGGGGCCAATTTCCAAGGTTCTTAGAGAAGATTTGGGGCCACAA
ATCTGCTCTGCCACTTCACTGCTGGGTGAAAGCTGTTGGCTTGAGAAGA
GAGAGAATAGGTGAGGGACAATAATTCTCAAGGCAAGCTAGCTGATATC
CTTTTCATTTGTGGCTTCCAAAGACAGGGAAAGGCAAGGCAGACCAGGGT
GGAAACAGCGACATCCTGAGGGGACGACGTCCGTTTTGCTAATTCTGTT
TCCCTGGCAGCTTTGTGCTGGACAAGATTTCTCTGGTTTCAGCTGAAGA
GTGAACAGCTGAGGAGCTCTGTGACTCTGAGAGAGAGAGAAATCAATAG
CCCTTGAAAGGAAAGCACTGCTTGTTCTTCCAGGCCAGGGCAGGCAGGA
TAAAGAGAACAAGGCTGTACATACCAAAGCCGAATTTCCATTAAAGGCC
AGAATCCTGGGAGGCCCTTTCAGCTTAATGACCATCTTCTGATCACTAT
CACTTAGAAAATGTTCATGTCTCCAGTTTTCTCTGCAGATAGTGCAGAC
ATCCTGTGCACATTGATATTTTATGCACCAGATGCAATTCTCTGCAAAG
GTCCCCTCTGGCTGGTGTCCATCCGCTTGCTCTCATGACCACTGATGCG
ACTCTGGGGCAAGTCAAGCCATTCCTTCTAGACTCTAGAATCTAGAGG
ATGATCCCAACTCACAGGCCTCTTGGACAAGCTTGCTTTGGATTCCTTC
TGCCTGTACTACCCAGACTGCCAGTCCTCCAGCAGGGCAATCCAACTTC
CTGCCTCTAGGGTGTGGGAGTCCTGGGCGGGGTTTGGAATCCACAGCAG
ATGGCTGGCAGGAGAGGCAGTTCCCGAGCACCCACTAGGTGCCAAGCAG
GCAGGTATCAGGTGCAGGGCTTCGGAGGTGCAGAAGCACAGCCCCTGTC
CCCCTCAGGTTCCCAGTCTGGCCTCAGGGACAGACAGGCAGGTAGGTAT
GGAAACGGGTACTGGAAGGCATACAGCTGAGGGAGAGAGCAGCTGCAC
CCTGGTCAATCCCCCACTCATTTCCCTGGAGGTGGGGCTGAGGCACCTG
GAGCACTCTGCTTGCTTGGGTTGTCCCTTTGCCAAAGAATGCCGGGCAG
AAAGTAGAGAACAAGCAGGCCCAGGAAGCACTAGAAGTCCCTCATGGGT
GGACAGAGCTTTACCTTCGGAGCTGTCACCTCCTGTGTTCCTCCCAACA
ACCCTGTGAGGCAGGCGGGCAGGCTGAGCAGGGGACTGTGCCCCGTTGA
CAGATGAGGAAAGCGAGGCTCAGGGGAAGTGACTTACCTGTGGCGTCG
CAGCTACGCAGTAGTGGAGCGGGCACCTGCCTCCAGGCCTTCGGATCCC
```

-continued

AGCTGCCCCAGGGCGCTGCCTCTGAGGTGCTGTACGAGGAGGTGACTCG
GGCCAGCTCATGAGCAAAGGAGCTGCCGGGCAGGAAGGACTCACTCCCC
AGGGCCTGGCAGGACGGGGGCTGTCGCCCGAGGCTGACCTGGGGGTGCC
TGGCTTCCCCAAGCTTGCAGGCTTTGTCTACATGAGTCTACAACAACCG
ATTGAACAATCCATCAGCTGCTTGGCCACAAAATGGTTCTGACTGATCT
TGTCACTGCCCTGAGTGTCTAGCTGGGTCATCTGGGTGTTGTGGTTATA
CCCACCAACTGCTTTGGTGGAACGAAACCGCGGCCGATCTGAATTCAGA
TCGGCCGCGGGATCATTCCTGGACTCAGATTGTTCTGAAGAAGCCCAGT
TCTGGGTGGCATCAAGTGCTTGCTAGATGGGGGGCTTGCCTTGATCCGG
CTACACTTGGAGGTGACTTGTTCTTGGACGGCTACATACAGAAAGAGAG
AAGTGGGGATGAGTTCCAAAGGCATCCTCGACTTCGGCTGTGGCCACCG
GAGGGTAGCTCCTGGCCCAACACGGACTTCTCACCTCCCGCCCTTGGCT
CTCTACTGAGCTCCCCCCTGCTCCCCAATTCCTCGCCATTCCCCTCATT
TCTCTGCCCTCAGCCTGGACTGCAGTTCTTCTGGGAAGCTGCCCCAACT
CCCTAGGTCTGTGCTCACCAAGAGCAGATCACACTGGACTGAAATGCCA
GCTGATTTGTCTCTTCAAGAAAATTGGAAGCTCCTGGAGGTCAGGGTCC
ATGTCTGCTTTTACACTCAGTGCTCTGTATGCAGGCCTGGCACTGCCCA
CCCTTTGACAGGTGGTGCATATTTTGTAGAAGGAAGGAAGGGGCCAGGT
GGGGTGGGCTGGGCTGGTGGCGGGAGCTAGCTCAGCCTCTTAGATTCTC
TACCCGATGGATGTGACCTGGGACAGCAAGTGAGTGTGGTGAGTGAGTG
CAGACGGTGCTTTGTTCCCTCTTGTCTCATAGCCTAGATGGCCTCTGA
GCCCAGATCTGGGGCTCAGACAACATTTGTTCAACTGAACGGTAATGGG
TTTCCTTTCTGAAGGCTGAAATCTGGGAGCTGACATTCTGGACTCCCTG
AGTTCTGAAGAGCCTGGGGATGGAGAGACACGGAGCAGAAGATGGAAGG
TAGAGTCCCAGGTGCCTAAGATGGGGAATACATCTCCCCTCATTGTCAT
GAGAGTCCACTCTAGCTGATATCTACTGTGGCCAATATCTACCGGTACT
TTTTTGGGGTGGACACTGAGTCATGCAGCAGTCTTATGGTTTACCCAAG
GTCAGGTAGGGGAGACAGTGCAGTCAGAGCACAAGCCCAGTGTGTCTGA
CCCACCCAAGAATCCATGCTCGTATCTACAAAAATGATTTTTTCTCTTG
TAATGGTGCCTAGGTTCTTTTATTATCATGGCATGTGTATGTTTTTCAA
CTAGGTTACAATCTGGCCTTATAAGGTTAACCTCCTGGAGGCCACCAGC
CTTCCTGAAACTTGTCTGTGCTGTCCCTGCAACTGGAGTGTGCCTGATG
TGGCACTCCAGCCTGGACAAGTGGGACACAGACTCCGCTGTTATCAGGC
CCAAAGATGTCTTCCATAAGACCAGAAGAGCAATGGTGTAGAGGTGTCA
TGGGCTACAATAAAGATGCTGACCTCCTGTCTGAGGGCAAGCAGCCTCT
TCTGGCCCTCAGACAAATGCTGAGTGTTCCCAAGACTACCCTCGGCCTG
GTCCAATCTCATCCCACTGGTGCGTAAGGGTTGCTGAACTCATGACTTC
TTGGCTAGCCTGCAACCTCCACGGAGTGGGAACTACATCAGGCATTTTG
CTAACTGCTGTATCCTAGGCCAATAAATGTTGATCACATTTATAGCTGC
CATGGTAGGGTGGGACCCCTGCTATCTATCTGTGGAGGCTCTGGGAGC

CCCTGACACAAACTTTCTGAAGCAGAGCCTCCCCAACCCCTTTTCCATT
CCCTATACCTGACAGATGGCCCAGGAACCCATTAGAAATGGAAGGTCAC
TGCAGCAGTATGTGAATGTGCGTGTGGGAGAAGGGCAGGATCAGAGCCC
TGGGGGTGTGGCAGCCCCCAAGTGATTCTAATCCAGATCCTAGGGTTGT
TTCCCTGTCCCATTGAAATAGCTGCTTTAAGGGGCCTGACTCAGGGAAA
TCAGTCTCTTGAATTAAGTGGTGATTTTGGAGTCATTTAGACCAGGCCT
TCAATTGGGATCCTGCTCTTAGAGTTGGATGAATTATTTAACTGATTTT
CAGATCTCCTCTTTCTCAATGCTTTCAGAAGCACAGTAACTGCTTACTC
TGAAATGAATTCTCACCCCACTTCCACATATGCACCCCTTGCCCACCCC
TTTGGGAACACTGGCCTTAACTGCTTACCTTCAAATGGACTCATCTGTT
GGGAGATATATGCATTCTGCCGTTCAGGGGTCATTGCCATAAGACCTGA
TCTCTGTTCCTCTTGCTAAACAGAAGATGAAAAAGACAAATTAGATTAC
AGCTACCAATTAATAATTAGCCTTAGGATCGCTGCGTGGGGACCTAGGA
CTTGGCTTTGGTGCAGCAGAAAGCATGAATAAACACACCAGCATACACT
CGCATGCATGCCCCACCCTCTCGAGCAAAATTCCACAGGTATAAATAAA
GTAAGATTCTGCACCTGGGTTAAAAACACAACTGCAACAGCATAGAATG
GGGCAGGAGAGACAGAACTTAATAGCAAGAGCACACAGAAAAAAGTTTT
AGGCATTTTGGATGTCCATCTGCTCAGGATGGGTCAGCAGTGAGATGCG
GTCACCAAAAGAACAAATGTAACATTAGGCTGCATTAATAGAAGCAGAG
TATGTAGAAGGAGGGAGGTGACAGTCCTATGCTAACTCTGCCTTGGCCA
GACTATACCCACAGGAGTCTGGGCATGCCAGTCTCAGGGAGACCCAGAC
AGACTGGCTGCATTCAGAGGATGGTAAGTAATGAGAGTGGGGATTGGAC
TTCAAACTACCCAGACAAAGAATGGCTGAGCAAGCCAAGGATGCTGTGG
CTGGGGCAGAGCAGACTGTGGGCTATGTAGTGGTGGATACCTAGCCTCT
GCAGGGCTGTCATAGGGAAAGGACATTGAGAAGAGGACTGAGGCTTGTT
CCTGGTGGTCCTGGCATGAACGGCCAGATGATCACATGGTCAGGTGGAC
ACAGTCTCCAACACTGGGAGTAGCCAAACACTTACTGCCAACCTCCCGC
CCTTCTCCTGACTAGTTGCAGCATAGGCAATTGGGAGGAGCTTCCTGTC
TCCATCTGAAAGCTGGCTGGGTGGCAGGGGGAGGAGCGAGCCAAGTTT
CAAGGCCGCAGTTTCAGCACTCAGTCTGGGATCGGCTCAAGGAGCAAAG
GGGAAGAACATAGCCAGGAGGGAATAACATGAAGGCCCCCAGACCCAGA
AAAGGCATGACTTGCTCTGAGACCCTCAGCCGGTTGGTGTCAGGTTGTG
ACTCGGATCCAGGTCTGACTCCCAGTCCAGTGCTTGAAGCCTCACCCCA
CACAGTGAGGGAGCCCGGCCATCTCTGCTCAACTGCTGCCATCTCTCT
CCCCTTCTCAACCACCAAGGCAGCTCTGTCTGGGAGCACAAGCTCCAAG
TCCACTTTCTGGTCTGTGTCCCCCCAAGATGCCAGAGGACTTGCCTCT
ACAACACGGGCTGCCCGTGCAGTGCCTGCTTTTCCAGCAAAGGGCTTCT
GGGAACCCTTCTCTGCACTCAGTGGGGCTGGTGGGAGTGGGGCGGGGTA
GCGACCCAGTGCTTGGGACTGTGCCCAGCTCTCAGGCCTGGCAGCAGTT
CCTGGCCTTGGTTCCTGCCAAGGCAGAGAGGACAAACACATGGCACCGG

-continued

GAAGACTACACCAGAAGCGATTCCACCAGACTGGGGTTTGCTTTTCTAT
CCCGCCCTTAGCCTGCTTCCTGTCCTGGTCCCTGCCTCCCCCTCCACTG
GAGCTGCCGTGTGGGCAGTGAGGGGCTGTTTTCTCAGCTGCCCTATGGA
GCTGCCCTCTCCCTGCCAAAGCATTGGCAAGGCGGCAAGGGGTGGGGGT
GGGGATGGGGGGTGGGATCTGCCTTCTCAAGCTCTCATTATACTGAGCA
CGTCTCACCCATTATTTTATGTCATCTAGCAACACCCCATGTGGACACT
GAGGAGCATGGGGGTCACATGACCACTGCCCAAGGCCACACCATCCGGA
TCTGCCTGAGATGGTCAGGGTTGGCAGCCATTTCTGAAGGCAGTCCTTT
CGCTTTGGCTCTTCTTGTACCAGTCTCAGGACATCAGGGCAGAAGATCT
ACAGTCCCCAGCTTACTGATGTGACAGCAGAGGCTCAGAGAGGTTAAAT
GACTTGCCCAAGGTGACACGGCTAAGAAGTACAGTATCTCCTAACTGCA
GACCAGGTGCTTCTGCTGCTTCTGGGGACAGATTCCTGCGTGGCTGGCT
AGGTCTAAACGGTCCTTAACTCCATCCCCACCGGTTGCTGCATTAGTTT
CATCAAATAACACAGTTGTACAGAGGTAGGGGTTCAGGGGCAGGGCAG
ATGGAGGCTGGAGAGTGTGACTAAGGAAACAGCAGGGGAAGTGCGGTAA
AGTCCGAAGGGAGGGACGGAAAGAGAAAGCCAAGCCCAGGGGCGTGCCA
GACAAAAGGAAAGGCCACGCCGGGGCAGGGCAGGCTTCAGCGGGTGCTG
GGGCGTCTTCATCCGGGGAAGCACACATTCCAGAGGACCCCGGAGTCTA
ATGGAAAAGCTGGCCAGCCTATCACTATGGAAACTGCCAAGGCCACACA
GCGCTACGCGTATTTAAATGTGCTGGAGTGTTGAGATACTGTAGTGGTG
GGATGCTTAAGTGCTGGGGTGCTGGGTGTTGGGATGCCTAGGTGCTGGG
GTGCCGAGATGCTGGAGTACTAGTGTGCTGGGATGCTGAAGTGCTGGGG
TCCTGAGATGCTGCAGTGCTAGGGTGCTGAGATTCTGGGCTGCTGGAGT
GTTGGGGTGCTGGGATGCTGGAGTGCTGAGATGCTTGGACAATGGGGTG
CTGGAATACTATGGTGCTGGGGTGCTGGGGTATTGAGATGCTAGGGTAC
TGGGATGCTGAAGTGCTGAGATCCTGGAGTGCTGGGCTGCTGGGCCACA
GGCTCTTGAATCCATTCGTCTGCCCAGGGGAAGAAACCAGAAGATAAAG
AGCTAATGAAGGAGCTTTGGTTGAGAGGGAGGAAGTAATGGAAGGAGCA
ACATCTTGTGGAGGAGCAGGAGAGAATGGACCTCAGGTTGGGAGAGAGG
GCCAGGCTACAGGCCAGAGAGGCAGAAGGATTCCAGCAGAGTGTGGGCT
CCAGGAGCCAAGGGGAAACAGGTTTCTGGGAGGAGAGAGTCCAGTACTG
CTGAAGTGGCAAGTCCGCTGAGGACCAGGAAGCTTCATTTGGCTTTATG
ACCAGGAGGAATTTGGAACTGTGACTAGAGTACTTAGGGGGAAGGAGGC
AAGACTGGAGCCAGATTGCTCTGGGTTGAGGGGTGAGTGGGAGGTGAAG
CAGGGCACTGTCACTCCTTTGAAGGGTGGCAGAGAGCTGGAATTGGTGC
TGGATGGGCTGTGGGGTGACAGGGTCATGTGGAAAGCCCCTGGGGGGCA
CCTGGAAAAGGAGAAGCTGACAGTACAGTGAGAGGACAGCTAAGGGAAA
GCGGAATGGCAGAACACGCACTGCCAGGAGGAATGAGGATAGGGTCAGG
AGTGCCAGGGGCAGTGAGGCCAGCCTGGGGTCAGGTGGCAGGACGTGTC
CAGGAAGCTGGTCTGCACTGCAGCCCACACTGGCTCAGCCTTGAGGTTC

-continued

CCTGTGTGGTTGGGGTAGGAAGTTGAACCCTCTGGGAATGGAAGATGGA
ACCAGCTCTGCGAGCCAAGCTCAGCTTTTATCTATGGGTCTCTGAGGGC
TGGCAGAGCTGAGTGGGGACAACTGTGATCCGTGAGGCTCTCAGGTTGA
GGTGGCCCCTCCGGGAGGGCTTCATTTCCCAGCGGGTAGGTTCTAAGCA
GCAGTGGCTGGGCAGGTGGGTCCAACACAGAGCCAGAGAAGGGTGAATG
GGCCTCCTGGCACCCCACCCCTGCTGCCCCTGAGCTCAGTGATGGAGGG
GGACAGCACAGCTGAGCCCAAGTGCTTTGGTGTGGCCCTGAGGGAAAGC
TGCAGCCTGCCTGGGGCCTGGCATGGATGGGACACTTGAGGCAGAGGGA
CAATAGTGGGCGCTGCAGTGAGGCTGGCTCTTGGAGAGGTTTCCTGAGG
AGTGCTGCCTGAGACGGGCAGGGAGAACAGAGACAAAGTTGGTGACAGG
GAATGAAAGCTGACTGAAGGACTTTACCCAGACCTATGAGGATATCTCT
CTCAGCAGGAAGCAGGAGGGGACTGTGTGAGGACTGGCCAAGAGCTGGA
GTGTTGGGAAAATGACTCTTTCTCCGACCCCTCTGTCCTAGCTCTGGCC
CCTGGACTGCGGAGGTCTGCTTCCACCCCATTGGTCGATCGTTGTCCC
TTGTCACAGCCATTGAGAATTTTGGCAGGGAGCATGTTCTTAGAGCATT
TTTAGGCTCTGCGGGACATAACAGCTCTGCCTCAGAGCACATGCCTTTC
TCAGCTCCTGAAAGCCACTGATCAAATTGGAACATTTTGTACCTTAGGG
ATGAGGATATCAACTCTCCCAGCCACTTAGAGGGATAAATGTGATGATG
CATTCAATTGTGACTACATCTGATCCCAACTGTTGCTTCAGCTGCTCTC
CTATAGCACATGGCGGAGGCGTGCATCCCAGTAGCTACCTCCCCACTT
TTGGGGAGATGTGGTTCCATCCATGAAACCTGGGTACCCGCCTACCAGG
TCCTGGCCTATCAGGTGGCAGGGTCTGGTCAAAGAAGGGCATGTGTGGT
CTTCAGCAAGGGAGACAGGACGGTGGTGCAGAGCGTCTAGACCCTCAGG
GCAAGTCTCCCCCACACCTGCTCCCGGGGCAGTTGTCTTTGTGACCTCC
CATCCCCCTCTGTTTCATCCTCTATAAAATGAGGGGCTGAGCCCCAAAA
TAACAGGCTTCTTTGCCATGATGCAAAACTGCTGAATCTTTCTTTCTGA
CACACAAGGCATCGAGCAGCCTCTGAAAGAACCAAAGCCACTAGCAGGC
TTCCTGACTTGGGTTTGTAGGTACTGAATACTCCCTTGAAAAATAAAAA
CATAGAGGCACTTTTCTCCTGGCTGTTTATTACAGAACGAAGAAAAAAC
ACACTGGCTTGAAACAGACGCCAGATTTCAAATGTAGAGGTGAAATACG
AGGTGGCAATTAAAATGTGATTACAGAAAGTCTGGACACTGAGAAAAGT
TTACAGGACAGTGGGTGTGGGTTTTCTATAACAGACACTTAAATATACA
TGACGATAATTGCAGATAGAAACCATCAAAGACAAACCCCAAATCAACT
AATAATGTTTACAGATGTTCCCCCCCAAACCACAGAGCCTTACATCAAA
ACAAATACTGAAAGGCTTTAAACCAGGAACAGCTCGCCTTAACCCCACG
AGGGTGCACACAAGCTGGGCTTTTTCTCGGTCTGAATGGTAAAGGGA
GGAGGATACTCTAGCTCCTCCAGGTGGATTGCTGAGACAGGGCTCGGCT
CACACACTGTCTCTGCGCCTCTCCCAAATCTGGAGAACTCTCCCAGCCT
CCTGGTAAAGTGTCTCTGTGGGGCACTTAACGATAAAACAGCTTCTGCT
GTAAAGCTCATTAGGAAAGAGCTAGCGGAGACTGAAAGGTTCGCAAAAG

```
AGATTAAGAATCACACAAGGCAATAGGATTTTTAGTGAACATAGAAATA
AATGGCCAAGTGGTTTTCTATTTGGCATTTGTCAACTTGCACAACAACT
CTTGGTCATATCCACATTGCTCATTGCATTAAAACCATAAGCGACTCAG
CCACCTAGCTTAACAAGGTATCACTGGAGCAAACAACACGGTCTGCATA
TTTGTAACATTGTATAATAAACACAAAACAATGCATAGTAAACACAACT
CTACTGAAACAAAAGCCGTCGCTTTATTTACAAAGTCACAAAATGAAGT
ATAAATACTTCTGTCATTAATGTTTAGGAAAACCATTTACAAAATTTTC
AAATATGTACACGTAGCTTGAAAAATCACCAGCTTTCCATTTTGTCACA
GGTAGAGAGAGGGATAAGCATGGGCTGACAACACCACTCAAATTGTAAC
GGGAGACAACTGCGGGTATGGATCGACACCACTTCCTAGAGTGATGTCA
CCATGGGGGTTTCTATGGGCATCCTGCTCAGATTTAAAGTGCCCCAGCA
TCCTGGGTGACTTGCCCAGAATTCTGGGCTGTGGCATTTTGAGCAGCAG
CATGCTGTTCCAAAATGTCGTCGATCAGCCTCAAGTTGCACACCCAGTC
TTCATCTGGGCTCACACAGGAGCCTTTCAAGAGAGCTTCAATGAAATCT
ACCTCATTGCAGTCAGGTGACGAAATCAGATCATTTAGTGGGGGTTGGG
GCTGGCGCAAAAAGTCGGCAGGTGGCAGCTCAGGGGAATATCCGTTCT
GTCGAACGGACCTGGGAACTGGCTGGCAGCAACGGCAGAAGCAGCAGCA
GCGGTGGCAGCAGCAGCCACATAGCTTGGTGGCTCGATGCCCTGTATGG
GGCTCAGGGGACTAAAGCTGGCCATACCCTGCTGGAGGAACTTGGTGGT
GTTTGCTACAGGCACCGGGCCCTGTACCGGGCTCTGCCTGAGGCTCTGG
CTGCCCAGCAGGCTGAAGCTGGGGTTGTTGGCCAGGGGCACTTGTGTTC
CCATCGCAGCGGGCACTTGTGCCTCCCAATCAGATGGCCTCTGAAGGCA
GGCCTGGCCAGAAGGTGAGTGCTGCTGAACGCTATTATCCACTTGGCTG
AGGGGTGTTTTCCCCGAAACTGCTGTGGTCACAGCTGCTGCCGCTGTGA
CCCATGCAGCATTGTTGAACGCAGTGGGCATTCTTGGCACACTAGGCCG
TCTGAGCTGGTGGGGACTCAAGGACTGGGTGCCCAGGGAGCTGGGACAG
AACCCAGGCAGGGGCACTTCTGGTGGGGTGGCCTTGGGGCTCTGCATAT
GCTGGCAGACAGAGTCAAGTCTGCCCAGGGGAGTCTGGCCTGAGTGTGA
GAGGATGGGACACTGGGGGCTGGAGGTGAAAATTCCTTGCCGCTTCCCC
AGAGTTGGTGAGATCACTCCCATGCCCGGCGCGCGCGTCGACGTGAGCA
AGTGGAATGGAGTGGCAGGGAATGAGTGAGGGAGACAACAGCTCAGTAG
GACCTTGTGGGCTACTGGAAAGACTTTGGCTTTGACTCTCAGTGAGATA
AGGAGGTATTTGAAGGAGTTTTAGCAGAGAAGGAACAATTCTGTTTATT
TTTAGGAGCTCTTTATATATTTAGGAAATTACTTCTTTGTTAGTCATAT
ATTTTGGAATTTGTTGTTCCCCGTTTGTCATTTCTGTTTCTACATTTTG
CTTATAATATTTGTCTATGTAAACCTTAATATGTACTTGGTTAAATTGA
TAAATTCTTTGCATAATTAATAGCTAGCTATTGTTGGCCTACCTATAAT
TAATTTTTGCTTTATCTAGTAATAGGCCTGAATTTTCATTTGGGATCCA
GCCCTCTCCCTGACACTATGCAGGGCCTGGGAGACTAAAGCCTGCTGGA
AATAACTCCAGCTTGGCCCTGCCAAACATTACAACACCTAGCACCTGCT
CTCCCCACCATAGTGACTGATTTGGGCAGGAATGAGACCACAGCCACTC
CAAGAGCCCAGCTGTTGGCTACCAGTAACATCTTCTCCTCTAAACAGGA
GATCCAGCTATATTGAAGGCTTCCAAAATTACCCTATGTCTACCTGTCA
CAGGAATGTTCAGAGGACTAAGCCTCTGCCTTTCTCCACCCCATACTTA
CTTCATATGGAACTATGAATGGGCAACTTCACAATTTATTATTTACGTC
ACCTAGATGCAAGTCAGAGGGAGAAGCAACAAATCAGCAGTACCTAAGA
AGTTCTCAAGTCCTCAAGGTGAACTTTACCTATATATACAAAATATATT
TGCCTCTTTCCTTTAACCCTTTTTCTTACTCCCACCACTTTCCACCCAA
TGTGTAATAATATTAGTCACTTCATAGAGTTCTTATGAGAAGTTAAATG
AGGAAATCATGTAAACCACTGAGGGCTGGCAACAAGTTCTTAATAAGTG
CTATTGAGTTATGAGTATTATTATCTCCCTTGGGCTGGATTCACAGTGT
CACCTCTTCTGGGACCATAGTAAGCCAATGGTTCCAGCTCCTTCTATTA
TGTCATTTTAATTTGGGGAATAGCTTAACATATTAGATGATCCTTTACA
TGCCTGAGCGGTCTTTCTTTGATGGTATTTCTATGATCTTATGAAGAGC
TAGATGTTGCCGCTCCATTTTATCTTGCTGGTGGCAGCTGGTGTTTAGC
CAACTTGTCTTTTTTTTCTGTCTTTATATTTTTGGTTTTGTTTTTTGG
CAGAAGCCTGTGTTTTTCAGATTACTTTTTGCTTGTGTCTACTTTTTCC
CAAAACAATATTACATATTTAAACTTATTGTATATTTAAGTTTATTTTAT
GCATCAAAAGTCGCATTGAATTTCTGTGCTATTGTGGGCAAATTGACA
TCAATGTAATTTAACTCATTTTATCCCAAATTAGGCTATCTCTTTCCAT
ATACTCAAATCTTCTTTTATGTCCCTCAACAGTTTCCTTCATATAAATA
TTGCATATTTCTAATTAAGTTTATTTTTCTAATCTCCATTTTGGATGTC
TTAAATATAGTCTTTTCTCCCTTTGCTCTTTATCAAAGATCTGCAAACT
ATGGCCTGTTTTTGTAAATAAAGTTTTGTAATAAAGTTTAAATGGCCAC
TCCCATTTGTTTACATGTTGAGTATGGCTGCTTTCAGACTGAAATGGCG
AATGAAGTGGTCATAACAAGACCATATGGCCTGGAAAGCAAATATATTT
ATTATCTGGCAATTTACAAAAAAAGTTTGCCAACCTCTGCTTTATATTT
TTGATCTAGTTGTTATTTGAAAATAAAGCTATTGATATTTGTATATTAA
TTTTTTACCCAGCTACCTTATTGTTTTTATTACTTAATAGTTTACAGTA
TTTCTTTTAGTTTTTCCAGGTGTAACATCTGTAAATATTAATAAATCTA
TTAGCTAATATTTCATTTAGCATTTTTATATCTATACTCACATGAGAAG
TTTTCTTTAATTTTCTTTTGTGTTTATCAACCTGTGTTCACTCAGGAAA
ATGAAGCCACTTAAGTATACCAGGAGTGGAGGGTTTCATATAGAAATGA
GGGCTTATTTGAATTTTGGGAAAGCTGATGAAACAGGTCAGCAGAGTTA
CTGCAGAAGACCAGGAAAGTTACATCTGGAAGGTTAGGGAAGCAGACAC
TAAAGACTTAAGCCTGAAGCATAGAAGTAAGGATCCGTCAATACTTATT
GAGAAACTTCTGGAATTCTCAAGAACCTCTGAGAAATCTCCCATTCTGT
GGCAATAAAGTGGTGGTACTCAAGCCATCACCAACATGGCTCATATGTC
TCATTGCACTATGTCCAAAGACAAATGGCCTCTGCTTCTCTTCTGTCTC
CTAAATCTCTTAAGATTTCCTCTTATTTGTTTAAGTCTAACCCAGAAGA
```

-continued

```
CTTACATGGCAGGTAATTTTGGTTCAACTTTATCTTCTAGTAGTGTCTT
CAAAAAAGTGTTCTTGGAAACTACAGCCCATGAAACATTATTGCATATT
TGAAAATATTTATCTGTCACCATTACACCTGAATGACAATTTAGCTAGC
TCAAATTTACTGGCTCACATCATCTTTTTTTTGGTAATTTTTTAAGTAC
TTCTCTACTGTCATGTAATGTTGTATGTAGGATAGCCTAAAGCCAACTT
GTGTTTTTTATTTTGCTGTTATAGTAGTTTGATCATTTTTGCCTAGAT
GCCCCATAGGATTATTTTTCTTTGTCTTTATTTCAGGAAACCTTACTAG
ACTATGGTTCAGTGCTGACTAGACATTTTTTTCCTTAAGAAACACCATG
CCCTTTAGATCCTTAGATTCAAATCTTTTTTAATATCAGTAAAGTTTTT
AAATTTACATATTGGATATTTTATACTTCTCTAGTTTTTCTTCTTAAAG
AAGAAAACATTAATTCTGTCTTTGCCTGTCTTCCATATCTACAATTTTC
TTCTAATCACTTTTTATAATTTCCATTTCATTTTGCTCAATTGCCTCAA
AGCTGCTATCTATTTTTCTGTTGTCAACAATCTGTACTCTTACATCAGC
TACTATGATAATATTGTGTCACCATTTACTACTATTTACAAGCTAACCA
TAATTTCTCTGATGATTTTAGTTTTCTCTTCTACTTTGTGTCCTAGATA
CAGGCAGCTCAATTTTAATTTTTGTTGCTTTTCTTGATTCCTTATACCT
CGCATTAAGCTCTTAATTCACAAATTACTTCCATTGTTAAGTTATTGAG
TTCTTAAACAAATATTTGGTCATGATTTTCATCTACTCCACATCAAAAT
GTTCATACTGTGTAGGCTGTTTGCCTTTTTTGTCCTGCTATTTTCCACC
ATTTTGTGACATTTTTGTATGGATCTCCTTGTTCGTTTTTTATTATTAG
TCATCCTTGAGTGAGCAGAAATCTTCCTAGAGCAGGTATTTGAAAGAAG
TAGTGTGGAAGAGGGGCTGGGGCTGTGTTCTGCGTTAGTAGAAAATCCC
CTAATTCTTAGAAAAATCCTTTATGATTCATGGTCTTGTGGGAGAAGGT
TGTGAAGCGGGTTTTGTGAATGTGCTTCATGTGCAATAGAGAGTGACTG
AGAGGTGGTTTAACCTTTCTTCTTAGCTCACAAAGAATGGCTGCTACAG
AGCTGCTTAACACCCACAGTTTTTCTTCTACATGCTGCACATTTACAAA
GATGGAGTATCCGTGAGTTTTCTCACTCATTCCTACCTCCCCTGCCATT
TTAAAGTATCCAAGGAAGTTGGGGAGATTCCCTCAGCTAAACAGCCACC
CAGATCTTATTGTTCCAAACAAAAAATTATTAGATTTGCCCTCTGAGCA
GGTCACCTACTTTGGAGAATTTTGTGCTCTGCCAGCTCTCCTCAAGATT
TGGAAAAGCAGTTATTTTCTATTGGAGCCCCCATCACTCCAGTCCAAAG
TTCACTGCATGTGACATCCCATCTTATTTGTCTGGTTCCTGATTATAGG
AGTTTCCCAGTTTCAACAAAAATACTGTCTTTGTTTTTGTTTCTCATTC
ATTTTTCCCCAATTTTGTTTCAAAGCGAAAAGTAAAAACATTCTTACTC
TAACATCTTAAAATTAATGTCTGGGAGGAACCTAAACTGCTCATTAATA
TATGCCATGCTATATGTGATATGGCAGAGACTGCTACCTGTCCACCAGA
ATCTATTTATTTTTCTTGGATGCACAATAAGACTACATTTCCTAGTCTC
CCTTGCAATTACATGTGACCATGTCATTAAGATTTAGTGGATGAAATTT
AAGCAGAAGCAAGGTGTGTAAATTCTAGGGCTGGCCCATTACAAACTTT
AACATGGGCACCTGTGTGTTTTTCCTTTTCTGCTTAATTGGGTTGGAGA
TAATCACAGTGATGCTGAAAGCCATGTGCTAAAGAAGGCAGAGCCTCCT
TCTGCTTGGGCTCCTGAATGACTGTGTGGAACAGAGGCCCTTGCCACTC
TTGGGCCATTCTGGATTATTACATGCACAAAGAGTAAAGTTCTTTTCTG
TTAAGCCATTAGATGTATGGGTTTATTTGCTGTTACAGCCTAGTCGAAC
CCAAATGATGTAGTGAGGGAGGCAGGACAAGGAAGAAACCTATTCAGTA
TGGAGTTATCCTTAGGGACAAGTTACAAAAATTATAAGGATCAGACACC
ACTGCTGGTTGATCCATTATAGACCAGAATAAGCAGGTGGTATGATTCC
AGAAGGAGATGCCATGGTTGTGTGAGAGAGAGATTAACCATTCCTATAA
ACAGAAGGGTCAAAGAAAGTAGCCAGTCACCAGAATGCTTATATTAAGG
AGGATTGTGACTACCTGTATATAAAGTATAGGAAGAAAATGGGGCAGGG
CAATTAAGATGAATTGCAGACACAACTATTTGTGCATATTAATTTGAAT
TTAAATTTAAACTTAATTTAAGGATAATTAAAGGAAAATCTTCCCTTAC
CTATTTCATGCTGAAGGGGTCTTTCAAGTTGTCAAACTCTCTCTATATA
AATAAGACTGCATAATCCAGACCCTCCGGAATCCAGAGATGAATTGCAT
GTGGTAGCTGATGTGTGGGAAGCCCACAGAGCAGCACTTCTGGTCATTG
CCATCCAGCTAGCTGGTGCTCTCAGAAGAATGAGATGAAGAGGCATGAC
TTTCAAGCTTCCTCTGCCATACAAGGTGAGTTGGGTTCCAGGCTTCTTC
CTAGCCCCTGTTTCTGCTTCCTCTGATTTAATACCCAGTCACTGAGTAC
CTACTAAACACTCGGCATTAAACTGAAAAGAACAGGGAAGTCAAAAACC
TTTTACCAATGCCTGATGGGATAAAGACATGACCCATCCCTCAAAGAGC
TTGTGGTCTTCCCATGGCAATGCCCTTCCTCCCTAGGCCAGATGGACTG
TGAAGAACAGCAGTCTCAAGTGGATTTATTGGGAAGCTCATGAAGACTC
AGCTCAATGGGCCATGTTTGCAGGGGCCCCTTACAAGGCTCTGCACTTG
ATTTTGTAATTTTGAATTATTTTTCTCAAAAAGGCCTCCCAAATTATGT
AAGCTTCAGGCCTTTAAAACTTGGATCTGTTCCCTTGAAGCCACATAAT
CTGATCAGAAATAATTTTCAGGGCTCATTGGGTGCTGGAGAATTCATGG
TTAGATATTTAAATAAAAATGCAGAGAATCTATAGGACTTTCCAACTGA
GACCAAGGCTTTTTTTTTCTGGTAGCTTGACTGCCAGGAAACAGAAAGC
GGGGCATCTCCACCTGCTGGCAGAAGACCAAAACTACACCATATTGCAT
TGACCGCAGACATCAGGCTTTGTTTCCTTTTAAGTGAATAGGTGAAATC
AATCAAGCAAACTGGAATTAGGAAACAGAAGGACCACTCACAACCGTAC
CTCCACAGCAAAGCTAACACTTTCATTTTGAATAACCCCTTCCAGCCC
CTGTTTACATCAGTCACATTTTTTGCATGGACATAATAGTGTTTCAGGC
AGTCCTGCTCTACAGAAGGCATTTGTTTCGCTGACCATAAGCATCTTAT
GTGCTTCTACATTGTCTTTATAGCCAGCTGTCTGAAGTTCTACATCATC
CGTCAGTGATGGGTCCTGAGTAAACTCAGCAGTCTCCTCTAAGTAACTT
GTATATATCCCTTTTATAAAGAATGCTGCAGTGGCCACCCTTAAGTATA
GAACTTTGTCTTTCCCAGGCATTACTTACAGGAAACTGGGGACCAAATG
CCACTCCATAGCATAGCTTAGGAGAAGTGAGATTCCAAAGGACAGAGTG
GGCTGGCACATATGTAGTAGAAGACTGGACAAATGAGAGTGAATGAGCG
```

-continued

AGTCTGTTGTGAGTGGATGACACGCAATGCAACCCCAAGGGCCGGCTCC

AATTTGCACAGTCCCTAAAACATCCCAGGGATCCAGTCTTATCGCAGTC

TCATCAACATTGACAATAATCATTTAGAGAATTTTCACCATGAGACTTT

TGACACTCTGCTCTGGGATTTTGGAGTTCCAACTGCTTTAACAATTTAT

ACAGTCACTCAAATGTAGAATCCAGTGAATTATTAATGACAATTTTGCT

CCGCATATTGAAAGGGCATTCTATATTAATCAATTATAAATCATGATAA

ATTGCTTTCTAAAAATTATACACTTGAAACCCAGAAATGTTCAAGCCCC

TCACCAGTTTACATACATCCTTAACCGTGTCTTGTTAACTGGGTGACCA

GGAAACAGAGAAAGGAGGATGTACTTAATGAATAACTGGCCAGAAGTCG

GAAGACCTAGATTTTCTTCCCATCCCTTCCATAGATTTGCTCTGTGACC

CTAGACAATTCATATGCCCCCTCTGTTACCATACTTTTAAGCTGAAGGG

GTTATAGTGCATACTTTCTGAGGTCCTTCTAACACTGGAGATCTATGAG

TTCATAAGATCACATAGAGTCTTGGACTTTTCAGAGATCACTAGGCATA

AGAAAGCCCTCGAGGACATCCTCTTCCTAGATCAACCACTCCAAGCTAA

GACCTTAATGGGTCTACACTGTCATCCATTTATATAGGAGAGAGGATGG

TACAAGCTAAGTGAAAGTCTGTTGTCAACTCAGGAACTAGGGTACAGTT

CCAGCAATCAATCTCCATGGAGGGTTAGCAGAGGTCTGGCCTAGCCAAT

TAGGGTTTGGCACTGCCATATGCTACTAGAAAACACATGCTTTCATGCC

AGGCAACAGGGTGGGAAGTGCAATGCCATTAAGGACCATACCTTAGCCT

ACTTAAACTAGCCTGGGATTGAGTTACTGAGCTCAAAATACAATTCAGC

ACACTTTCCTGCCCACTGCAAGTCAGGCCAGCCCTGGAGAACTCCAGG

GACAAGGCAAGTCTGGAGTTTGTCCCCAAGGAACTCCCAGTCTAGTGGA

GGAGATGGGCCCATAGCAGAGTTACAAATGTCCAAAATAAGAGCACAAA

TTCCTGGGTTCTTAAAGAGAGTTCAAGCACACACACACAGAGAGAGAGA

GAGAGAGAGAGAGAGAGAGAAATTAATTTAGATAAGGAAGGGAGGTAGG

GAGAGATGGTGCCAGCAATGGCTTCCTGAGGAAATGTCACTTGTGATGG

GTCTTTTAGGTGAGTTGGACATTGAGAGAAAGTAATCAAAAGGGCACAA

GATAGGGTAGCTGTCAGGTAAACAAAACAAAACTGTATGCACAAAGGTC

TAGAGGCAAGAAAGCATGGGTGTGCTTGCATAGCAATGAAGAATGTGGT

TTGGCCAAAGCATAGGATTTCACAGAAGGACCTCCCCAGGCCATCAGTA

GTCTCTCCTTCGCAGGAGTCCACTGTGGCTGGACGAGGAACAGATCAAA

ACAGGTCTTGTTTGAGGCTTGGCCCAACAACAGGGCCAGCTGTTGACCA

GGGCTTCCTTCACCCTTAGCTTTCTCTCCCCCTAGTGTAGTCAGAGACT

CCAAAGGCAGTCCCAGAGTGTTGTGCCAAAACAAATGCACATCAGGCTA

TGTCATCAGGAGCCCTTGTCTTGTTCTGTTTGTTTTAAGAAGACATAAG

TGAAATAACCAGGTTTCCGAAGAGAGGGCAGAATTGGGTTTGTCCCCAG

GGAAAATGAGGTTTCTCCACCATGGCTGTTCTCCCCATGCAGCAGCGGC

CAGGGGTCCCCAGCAGCTCTTTGCTCAGTGCCCCTGATGCTAGGCCTGA

TGCTTCCTATGTGGTCAGCTCAGATGTGCAACCCTTCTCCATTTTTATT

-continued

ATTTGAGCAATATAATCATTATTGCTTTTGTTACCCAAAATCTTATAAT

CACCCATTAAGAGTAATGTAGGAATCATTTTTCTCTTTTATTTGATGAA

CTAATCTTTCTGGTTGGCTCTTGAGGTGGGAGGGGTGGGCAATGGGGAC

CAGCCTGCTTCATCTCACTCTTTCCTAGGCCTGCTCCTTAGGCACGTGC

CCCACAAATCCCACCTCCGCAGGTTGGAAAAGGGGCCCACAGAGGATCT

CAGGTATCTGAGGAAGGGCCAGAGGCTATTTGGCCTGACATCCTGGAAC

ATCACCAGCCAGGAGCCATAACTCCTTTAGGCTAGCCTGCCTGCAACTG

GATCAGGTATAGCAAAAACGATTGATCTCACCTTCTAATTTTCAATGAG

TGGGAGTGGCTGCCTTGAGTGCTGTGTTGGGAAGGAGTCTGAGGCAGCA

TCTGGACCCTGTGTAAATATGCGTTTCCTGTTATTGATGAAGCTTTCAA

GACAAGATTTTAGAAAGCTTTGGCTCAAGTTGTAGGTTGTGGGAGGAAG

GAATTAGTAAGAGCCATCATAAACTCAACATCTATTGTTCCAGGAGCTG

TGACCACTCCCTTCTTTTTAGTCGGGAAGGTCAGGATCTCACTATGTCA

CCTAGGCTAGAGTGCAATGGTGTGATTATTGCTCATTGTAGTCTTGAAT

TTGAATTCCTGGGCTCAAGTAATCCTCCTGCCTCAGCCTTCTGAGTAGG

TGGGACTACTGGTGTGTGCCACCACACTCGGCTTACTCCTCCCTTTGTA

TCCTGCTGCATCGTTAGTGCATGATACCCACCACCCCCTCAGAGGCCCA

GCCTAGTGCTGTCTCTCAGAAAAACACCCTTTGAGTCAACAGAGACAAA

CTTAGGGGGTGCCTGACTCCAAAGTCCAGGCCTTCCTCCTTTGAGGAAC

AGCATGGCTTCCCCAGGGAATATCATTCCATGGAGACAAGGCCTGCAGA

CAGATCTCATTTTCATCTGTTCTTTTACTAGCCCTTGGAGGATTTGCTC

CAAAAACCTGAGGCACTGATGTTTACTCCAGCTTTACTTCCCCCATACC

TGGTGAACAACTCTGGCCCAGCTTCCACACACCAAGGCCCATGGCTCTA

ATAGAGCCAGAGAGGCAGTCTCAGCTAAGAAGAGCTGTATCCTCCAGGG

ACCAGCAGGAACTTCCAGAGATATCCTACAAGCTCCAACTGCTGGGAAA

AGCAGACTGGGGTCTTCCTCAGGCTCCACCAAAGATAGCCAAGTGGCAG

CAATGACATGAGCACCTCATTCCTGTCCTAGACCCTGGCAATTCCATGA

GAGGGAGGCTCTGAATTCACCTCTGTTCCCAGGATGTGTGACATCAATG

CACATTGTCATACCAGATACACCTGCCAAACTTCAGAACCCCTGGGAAG

TGACCAGAATGCCACTGAATTCAACACCTTAGACCAATGAACATGACCT

GGGTCCTGTAGGATAGGAGGCAGCAGCAGTGTATACCCAGACCTGGTCG

ACTCGAATAGATCTGCTAGGCGCCAAGCTTGTCAGCCTTACCAGTAAAA

AAGAAAACCTATTAAAAAAACACCACTCGACACGGCACCAGCTCAATCA

GTCACAGTGTAAAAAAGGGCCAAGTGCAGAGCGAGTATATATAGGACTA

AAAAATGACGTAACGGTTAAAGTCCACAAAAAACACCCAGAAACCGCA

CGCGAACCTACGCCCAGAAACGAAAGCCAAAAAACCCACAACTTCCTCA

AATCGTCACTTCCGTTTTCCCACGTTACGTAACTTCCCATTTTAAGAAA

ACTACAATTCCCAACACATACAAGTTACTCCGCCCTAAAACCTACGTCA

CCCGCCCCGTTCCCACGCCCCGCGCCACGTCACAAACTCCACCCCCTCA

TTATCATATTGGCTTCAATCCAAAATAAGGTATATTATTGATGATGTTT

Other embodiments are within the following claims. While several embodiments have been shown and described, various modifications may be made without departing from the spirit and scope of the present invention.

What is claimed:

1. A nucleic acid molecule comprising a packaging signal cassette flanked by a recombinase recognition sequence,
   wherein said packaging signal cassette comprises a modified adenovirus packaging signal having two to six A elements having a consensus sequence of ATTTGN$_8$CG (SEQ ID NO:1),
   wherein N$_8$ of each A element is replaced by the N$_8$ sequence of a different A element, and
   wherein the resulting A element is different from both the wild-type packaging signal A element and from each other.

2. The nucleic acid of claim 1, wherein said modified adenovirus packaging signal contains from three to five A elements.

3. The nucleic acid of claim 1, wherein said recombinase recognition sequence is loxP.

4. The nucleic acid of claim 1, wherein said recombinase recognition sequence is frt.

5. The nucleic acid of claim 1, wherein said wild-type packaging signal is human adenovirus serotype 5 packaging signal.

6. The nucleic acid of claim 1, wherein the modified packaging signal comprises at a maximum 23 bp of contiguous sequence homology relative to a wild-type packaging signal.

7. The nucleic acid of claim 1, wherein said modified adenovirus packaging signal further comprises SEQ ID NO:3.

8. The nucleic acid of claim 1, wherein said modified packaging signal comprises an A element 21 bp after AII.

9. The nucleic acid of claim 1, wherein said nucleic acid is a plasmid.

10. The nucleic acid of claim 1 further comprising elements for use as an adenoviral helper virus vector.

11. The nucleic acid of claim 10, wherein said helper virus vector does not contain an E1 gene.

12. The nucleic acid of claim 11, wherein said helper virus vector comprises an E3 region with an insert of about 2.9 kb.

13. The nucleic acid of claim 12, wherein said insert does not contain a promoter sequence.

14. The nucleic acid of claim 13 wherein the E3 region has an insert of at least about 2.7 kb, provided that said insertion does not contain a promoter sequence.

15. The nucleic acid of claim 14, wherein said insert is a human intron sequence.

* * * * *